US006967212B2

(12) United States Patent
Cheng et al.

(10) Patent No.: US 6,967,212 B2
(45) Date of Patent: Nov. 22, 2005

(54) SUBSTITUTED AZOLE ACID DERIVATIVES USEFUL AS ANTIDIABETIC AND ANTIOBESITY AGENTS AND METHOD

(75) Inventors: Peter T. Cheng, Princeton, NJ (US); Hao Zhang, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 195 days.

(21) Appl. No.: 10/294,525

(22) Filed: Nov. 14, 2002

(65) Prior Publication Data

US 2003/0158232 A1 Aug. 21, 2003

Related U.S. Application Data

(63) Continuation-in-part of application No. 10/153,454, filed on May 22, 2002, now abandoned.
(60) Provisional application No. 60/294,380, filed on May 30, 2001.

(51) Int. Cl.[7] .................... A61K 31/421; C07D 263/32; C07D 413/10; C07D 417/14
(52) U.S. Cl. .................. 514/365; 514/374; 548/194; 548/236
(58) Field of Search ................. 548/194, 236; 514/365, 374

(56) References Cited

U.S. PATENT DOCUMENTS 6,506,781 B1 * 1/2003 Cobb et al. ................ 514/363
6,653,314 B2 * 11/2003 Cheng et al. .............. 514/256

* cited by examiner

Primary Examiner—Fiona T. Powers
(74) Attorney, Agent, or Firm—Burton Rodney

(57) ABSTRACT

Compounds are provided which have the structure

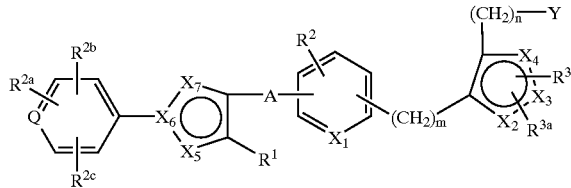

wherein Q is C or N; $R^{2a}$, $R^{2b}$, $R^{2c}$, $X_1$ to $X_7$, $R^1$, $R^2$, $R^3$, $R^{3a}$, $R^4$, A, Y, m, and n are as defined herein, which compounds are useful as antidiabetic, hypolipidemic, and antiobesity agents. The present invention further provides a method for treating obesity and dyslipidemia in mammals including humans through simultaneous inhibition of peroxisome proliferator activated receptor-γ (PPARγ) and stimulation of peroxisome proliferator activated receptor-α (PPARα).

19 Claims, 3 Drawing Sheets

SUBSTITUTED AZOLE ACID DERIVATIVES USEFUL AS ANTIDIABETIC AND ANTIOBESITY AGENTS AND METHOD

This application is a continuation-in-part of application Ser. No. 10/153,454 filed May 22, 2002, now abandoned, which is incorporated herein by reference, which application claims priority from U.S. provisional application No. 60/294,380 filed May 30, 2001 which is incorporated herein by reference.

FIELD OF THE INVENTION

The present invention relates to novel substituted azole acid derivatives which modulate blood glucose levels, triglyceride levels, insulin levels and non-esterified fatty acid (NEFA) levels, and thus are particularly useful in the treatment of diabetes and obesity, and to a method for treating diabetes, especially Type 2 diabetes, as well as hyperglycemia, hyperinsulinemia, hyperlipidemia, obesity, atherosclerosis and related diseases employing such substituted acid derivatives alone or in combination with another antidiabetic agent and/or a hypolipidemic agent and/or other therapeutic agents. The present invention also relates to a method for treating obesity and dyslipidemia in mammals including humans through simultaneous inhibition of peroxisome proliferator activated receptor-γ (PPARγ) and stimulation of peroxisome proliferator activated receptor-α (PPARα). The invention further provides a list of target genes wherein their expression is altered in adipose (fat) tissue through PPARγ antagonist activity to achieve antiobesity, insulin sensitivity and cardiovascular disease benefits.

BACKGROUND OF THE INVENTION

In mammals, including humans, adipocytes (fat cells) store excess energy in the form of triglycerides at times of nutritional excess (see Lowell, Cell, 99: 239–242, 1999). During starvation, stored triglycerides are degraded to fatty acids in adipocytes in order to supplement nutritional and energy requirements. Conditions in which excess adipose tissue accumulation, achieved either through recruitment of progenitor cells (pre-adipocytes) to become adipocytes (differentiation) and/or through expansion of the pre-existing adipocytes (hyperplasia and hypertrophy), leads to obesity and insulin resistance (see Lowell, Cell, 99: 239–242, 1999). Because, hypertrophied adipocytes (which are considered relatively less metabolically active) produce excessive amounts of fatty acids and cytokines which in turn act to reduce insulin signaling and glucose uptake in skeletal muscle and adipocytes, two major glucose utilizing tissues (see Hotamisligil, et al., Science, 259: 87–90, 1993; Lowell, Cell, 99: 239–242, 1999). Obese individuals frequently suffer from inadequate energy expenditure, high fat content in skeletal muscle, liver and plasma, insulin resistance, hypertension, atherosclerosis and cardiovascular diseases (see Rosenbaum et al., New. Eng. J. Med. 337: 396–407, 1997, see Friedman, Nature, 404: 632–634, 2000). Conditions such as seen in lipodystrophic syndrome patients with severely depleted fat depot leads to reduced body weight, increased lipid content in plasma, liver and skeletal muscle which in turn pre-dispose the patients to insulin resistance and Type 2 diabetes (see Arioglu et. al., Annals of Int. Med, 2000,133:263–274). The primary cause of these abnormalities appears to be due to relatively small amounts of adipose tissue available for safe storage of lipids.

Obesity is a common clinical problem in most developed nations and is also rapidly becoming a major health concern in developing nations. Overweight individuals frequently suffer from several metabolic disorders such as dyslipidemia, insulin resistance and Type 2 diabetes. These individuals also frequently suffer from hypertension, atherosclerosis and increased risk for cardiovascular diseases (see Friedman, Nature, 404: 632–634, 2000).

Peroxisome Proliferator Activated Receptors (PPARs) are members of the nuclear hormone receptor family of ligand regulated transcription factors (see Willson, et al., J. Med. Chem., 43: 527–550, 2000, Kersten et al., Nature, 405: 421424, 2000). Three PPAR isoforms, PPARγ, PPARα, and PPARδ have been isolated from various mammalian species including humans. These receptors, as a class, form obligate heterodimers with their binding partner RXRα, and are activated by diet derived long chain fatty acids, fatty acid metabolites and by synthetic agents (see Willson, et al., J. Med. Chem., 43: 527–550, 2000). It is now well documented that PPARs, through regulation of genes in glucose and lipid metabolism pathways, play a major role in maintaining glucose and lipid homeostasis in mammals including human.

PPARγ is a principal regulator of pre-adipocyte recruitment and differentiation into mature adipocytes and lipid accumulation in mature adipocytes (see Tontonoz et al., Current Biology, 571–576, 1995). Activators of PPARγ promote pre-adipocyte differentiation, lipid storage in mature adipocytes and act as insulin sensitizing anti-diabetic agents (see Tontonoz et al., Current Biology, 571–576, 1995; Lehmann et al., J. Biol. Chem., 270: 12953–12956, 1995; Nolan et al. New. Eng. J. Med., 331: 1188–1193; Inzucchi et al., New Eng. J. Med., 338: 867–872, 1998, Willson, et al., J. Med. Chem.: 43: 527–550, 2000, Kersten et al., Nature, 405: 421–424, 2000). The PPARγ induced anti-diabetic activity is however, frequently accompanied by some body weight gain in animal models and in humans. PPARγ expression is significantly elevated in the adipose tissue of obese individuals (see Vidal-Puig et al., J. Clinical Investigation, 99: 2416–2422, 1997), and a mutation which generated constitutively active PPARγ is associated with severe obesity (see Ristow et al., New England J. Med., 339:953–959, 1998). Partial loss of PPARγ expression leads to resistance to diet induced obesity in heterozygous PPARγ knock-out mice (see Kubota et al. Mol. Cell; 4:597–609, 1999) and lower body mass index in human with a proline to alanine change at amino acid position 12 (see Deeb et al Nature Genetics, 20:284–287, 1998). Relatively more severe loss of human PPARγ activity through dominant negative mutations, which abolish ligand binding to the receptor, leads to hyperlipidemia, fatty and liver insulin resistance, (see Barroso et al. Nature, 402, 860–861, 1999). The major cause of the abnormalities appears to be due to relatively small amounts of adipose tissue available for safe storage of lipids. These mouse and human findings show therefore, a role for PPARγ in the induction and or progression of obesity and suggest that inhibition of PPARγ will lead to a reduction in adiposity and obesity. These findings also suggest that such a reduction is likely to lead to higher plasma free fatty acids and hyperlipidemia and development fatty liver and insulin resistance The PPARα isoform regulates genes in the fatty acid synthesis, fatty acid oxidation and lipid metabolism pathways (see Isseman and Green, Nature, 347: 645–649, 1990; Torra et al., Current Opinion in Lipidology, 10: 151–159, 1999; Kersten et al., Nature, 405: 421424, 2000). PPARα agonist (such as fenofibrate, gemfibrozil) treatment enhance fatty acid oxidation in the liver and muscle, reduce fatty acid and triglyceride synthesis in the liver and reduce plasma triglyceride levels (see Kersten et al., Nature, 405: 421424, 2000). In patients with high triglycerides and low HDL-cholesterol treatment with PPARα agonists lead to an increase in plasma HDL-cholesterol, decrease in plasma triglycerides and reduction in both primary and secondary cardiac events (see Balfour et al., Drugs. 40: 260–290, 1990; Rubins et al., *New Eng. J. Med.,* 341: 410–418, 1999).

Therefore, by combining PPARγ antagonist activity and PPARα agonist activity in a single dual acting compound or in a formulation, it is possible to inhibit PPARγ and treat obesity without causing hyperlipidemia, fatty liver and insulin resistance. The present invention shows a novel method of treatment of obesity by combining two different activities, the PPARγ antagonist activity and PPARα agonist activity, to reduce adiposity and body weight without causing hyperlipidemia and insulin resistance. The invention proposes that the obese, hyperlipidemic and insulin resistant Type 2 diabetic patients can be treated with a dual PPARγ antagonist/PPARα agonist or a PPARγ antagonist and a PPARα agonist in combination with a lipid lowering agent and an anti-diabetic agent. The invention also provides a list of target genes wherein their expression is altered in adipose (fat) tissue through PPARγ antagonist activity to achieve anti-obesity, insulin sensitivity and cardiovascular disease benefits.

In accordance with the present invention, substituted acid derivatives are provided which have the structure I wherein
m is 0, 1 or 2; n is 0, 1 or 2;
Q is C or N
A is $(CH_2)_x$ where x is 1 to 5; or A is $(CH_2)_x^1$, where $x^1$ is 2 to 5, with an alkenyl bond or an alkynyl bond embedded anywhere in the chain; or A is $-(CH_2)_x^2-O-(CH_2)_x^3-$ where $x^2$ is 0 to 5 and $x^3$ is 0 to 5, provided that at least one of $x^2$ and $x^3$ is other than 0,
$X_1$ is CH or N
$X_2$ is C, N, O or S;
$X_3$ is C, N, O or S;
$X_4$ is C, N, O or S, provided that at least one of $X_2$, $X_3$ and $X_4$ is N;
$X_5$ is C, N, O or S;
$X_6$ is C or N;
$X_7$ is C, N, O or S, provided that at least one of $X_5$, $X_6$ or $X_7$ is N.

In each of $X_1$ through $X_7$, as defined above, C may include CH.

$R^1$ is H or alkyl;

$R^2$ is H, alkyl, alkoxy, halogen, amino or substituted amino;

$R^{2a}$, $R^{2b}$ and $R^{2c}$ may be the same or different and are selected from H, alkyl, alkoxy, halogen, amino or substituted amino;

$R^3$ and $R^{3a}$ are the same or different and are independently selected from H, alkyl, arylalkyl, aryloxycarbonyl, alkyloxycarbonyl, alkynyloxycarbonyl, alkenyloxycarbonyl, arylcarbonyl, alkylcarbonyl, aryl, heteroaryl, cycloheteroalkyl, heteroarylcarbonyl, heteroarylheteroarylalkyl, alkylcarbonylamino, arylcarbonylamino, heteroarylcarbonylamino, alkoxycarbonylamino, aryloxycarbonylamino, heteroaryloxycarbonylamino, heteroaryl-heteroarylcarbonyl, alkylsulfonyl, alkenylsulfonyl, heteroaryloxycarbonyl, cycloheteroalkyloxycarbonyl, heteroarylalkyl, aminocarbonyl, substituted aminocarbonyl, alkylaminocarbonyl, arylaminocarbonyl, heteroarylalkenyl, cycloheteroalkyl-heteroarylalkyl; hydroxyalkyl, alkoxy, alkoxyaryloxycarbonyl, arylalkyloxycarbonyl, alkylaryloxycarbonyl, arylheteroarylalkyl, arylalkylarylalkyl, aryloxyarylalkyl, haloalkoxyaryloxycarbonyl, alkoxycarbonylaryloxycarbonyl, aryloxyaryloxycarbonyl, arylsulfinylarylcarbonyl, arylthioarylcarbonyl, alkoxycarbonylaryloxycarbonyl, arylalkenyloxycarbonyl, heteroaryloxyarylalkyl, aryloxyarylcarbonyl, aryloxyarylalkyloxycarbonyl, arylalkenyloxycarbonyl, arylalkylcarbonyl, aryloxyalkyloxycarbonyl, arylalkylsulfonyl, arylthiocarbonyl, arylalkenylsulfonyl, heteroarylsulfonyl, arylsulfonyl, alkoxyarylalkyl, heteroarylalkoxycarbonyl, arylheteroarylalkyl, alkoxyarylcarbonyl, aryloxyheteroarylalkyl, heteroarylalkyloxyarylalkyl, arylarylalkyl, arylalkenylarylalkyl, arylalkoxyarylalkyl, arylcarbonylarylalkyl, alkylaryloxyarylalkyl, arylalkoxycarbonylheteroarylalkyl, heteroarylarylalkyl, arylcarbonylheteroarylalkyl, heteroaryloxyarylalkyl, arylalkenylheteroarylalkyl, arylaminoarylalkyl, aminocarbonylarylarylalkyl;

Y is $CO_2R^4$ (where $R^4$ is H or alkyl, or a prodrug ester) or Y is a C-linked 1-tetrazole, a phosphinic acid of the structure $P(O)(OR^{4a})R^5$, (where $R^{4a}$ is H or a prodrug ester, $R^5$ is alkyl or aryl) or a phosphonic acid of the structure $P(O)(OR^{4a})_2$;

$(CH_2)_x$, $(CH_2)_x^1$, $(CH_2)_x^1$, $(CH_2)_x^3$, $(CH_2)_m$, and $(CH_2)_n$ may be optionally substituted with 1, 2 or 3 substituents;

including all stereoisomers thereof, prodrug esters thereof, and pharmaceutically acceptable salts thereof.

Preferred are compounds of formula I of the invention having the structure IA

More preferred are compounds of formula I of the invention having the structures IB

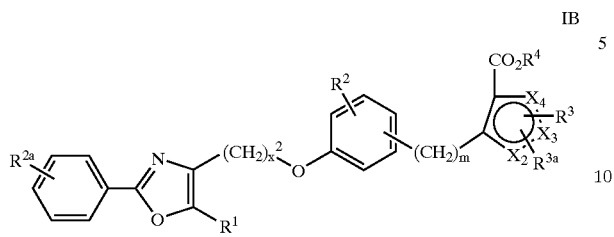

IB

In the above compounds, it is most preferred that $R^{2a}$, $R^{2b}$ and $R^{2c}$ are each H; $R^1$ is alkyl, preferably $CH_3$; $x^2$ is 1 to 3 and $x^3$ is 0; $R^2$ is H; m is 0 or $(CH_2)_m$ is $CH_2$ or CHOH or CH-alkyl, $X_2$, $X_3$, and $X_4$ represent a total of 1, 2 or 3 nitrogens; $(CH_2)_n$ is a bond or $CH_2$; $R^3$ is aryl, arylalkyl or heteroaryl such as thiophene or thiazole, most preferably phenyl or phenyl substituted with alkyl, polyhaloalkyl, halo, alkoxy, preferably $CF_3$ and $CH_3$, $R^{3a}$ is preferably H or alkyl.

Preferred compounds of the invention include the following:

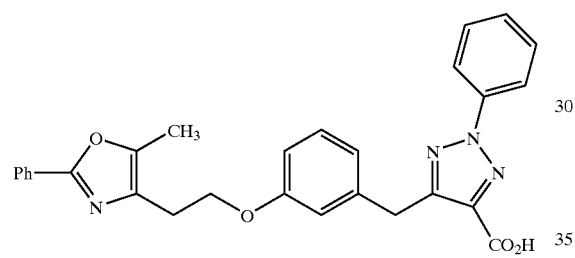

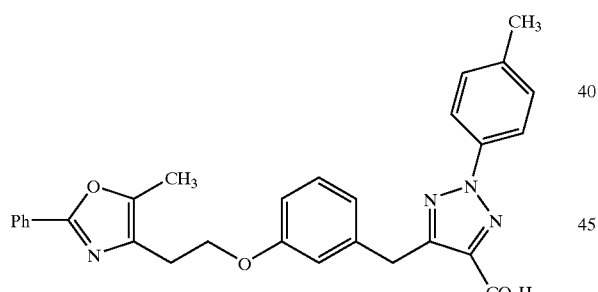

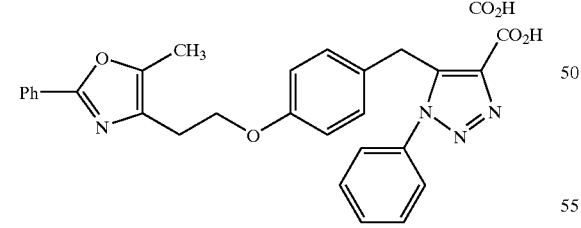

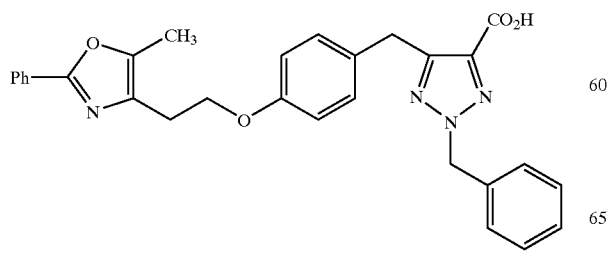

-continued

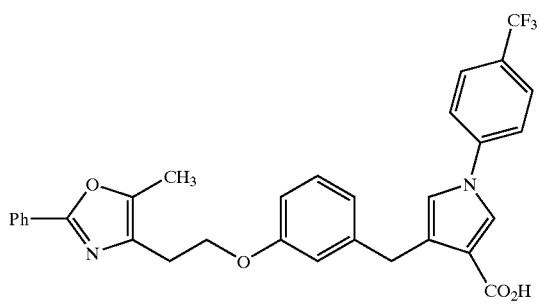

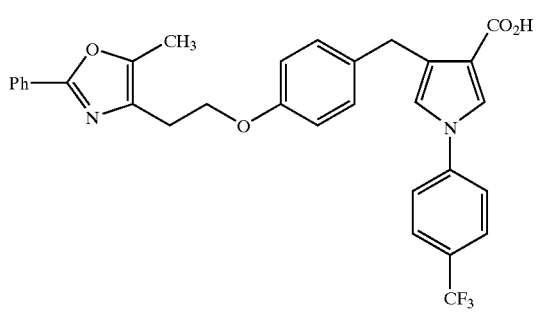

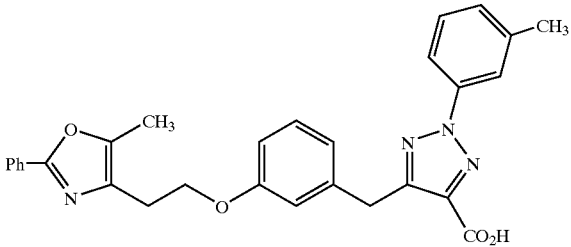

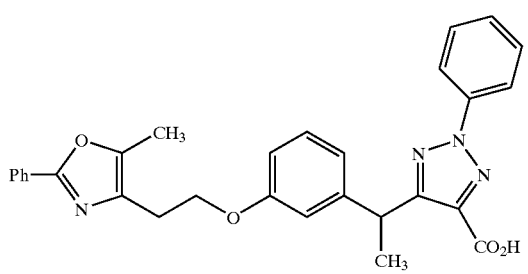

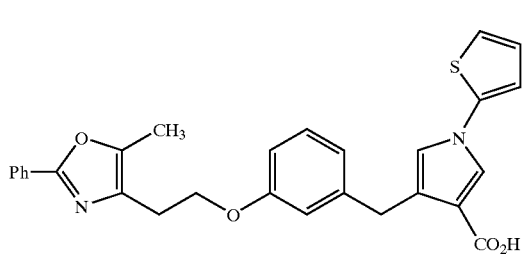

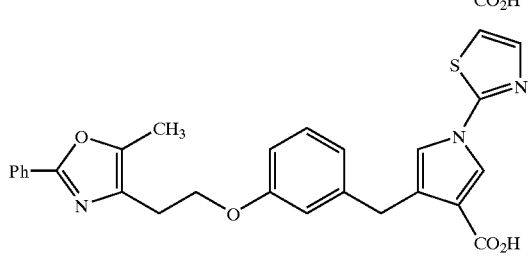

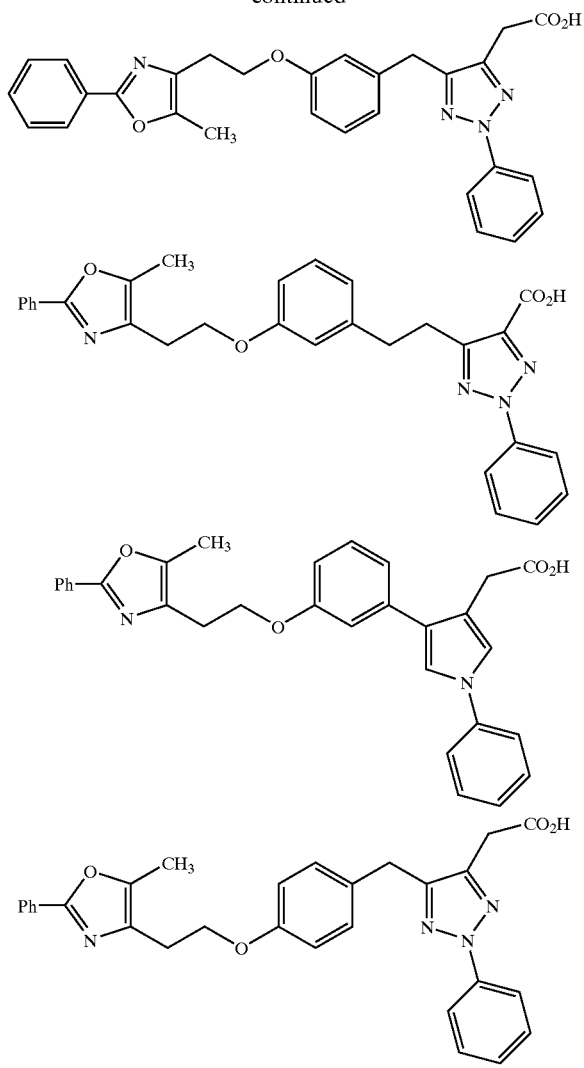

The present invention describes the discovery of dual PPARγ antagonist/PPARα agonist activity in a single molecule. The invention shows that administration of a dual PPARγ antagonist/PPARα agonist to severely diabetic, hyperlipidemic and obese db/db mice leads to a reduction in plasma triglycerides and free fatty acid levels, without a change in glucose levels. The present invention shows that administration of a dual PPARγ antagonist/PPARα agonist to a diet-induced obese mice leads to reduced body fat content and reduced fat in liver without inducing hyperlipidemia and or insulin resistance. The invention provides a list of target genes wherein their expression is altered in adipose (fat) tissue through PPARγ antagonist activity to achieve anti-obesity, insulin sensitivity and cardiovascular disease benefits.

Accordingly, one object of the present invention is to provide a novel method for treating obesity in a mammal, including human, comprising administering to the mammal in need of such treatment a therapeutically effective amount of a single compound or combination of compounds that simultaneously inhibits PPARγ and activates PPARα.

Another object of the present invention provides a method for treating metabolic syndrome (obesity, insulin resistance and dyslipidemia) in a mammal, including a human, comprising administering to the mammal in need of such treatment, a therapeutically effective amount of any combination of two or more of the following compounds: a compound or combination of compounds that antagonize PPARγ, activates PPARα activity, an anti-diabetic compound such as but not limited to insulin, metformin, insulin sensitizers, sulfonylureas, aP2 inhibitor, SGLT-2 inhibitor, a lipid-lowering agent such as but not limited to statins, fibrates, niacin ACAT inhibitors, LCAT activators, bile acid sequestering agents and a weight reduction agent such as but not limited to orlistat, sibutramine, aP2 inhibitor, adiponectin.

Another object of the present invention is to provide a list of target genes (such as HMGic, glycerol-3-PO$_4$-dehydrogenase, G-protein coupled receptor 26, fatty acid transport protein, adipophilin and keratinocyte fatty acid binding protein) whose expression can be altered to obtain anti-obesity effects through administration of a PPARγ antagonist and dual PPARγ antagonist/PPARα agonist or through other methods.

Another object of the present invention is to provide a list of target genes (such as PAI-1, Renin, angiotensinogen precursor) whose expression can be altered to obtain beneficial effects against cardiovascular diseases through administration of a PPARγ antagonist and dual PPARγ antagonist/PPARα agonist or through other methods.

Another object of the present invention provides a pharmaceutical composition for the treatment of obesity comprising: a pharmaceutically acceptable carrier and a therapeutically effective amount of a compound or combination of compounds that simultaneously inhibits PPARγ and activates PPARα.

Another object of the present invention provides a pharmaceutical composition for the treatment of obesity, insulin resistance and/or dyslipidemia, comprising: a pharmaceutically acceptable carrier and a therapeutically effective amount of a compound or combination of compounds that simultaneously inhibits PPARγ and activates PPARα and an anti-diabetic compound, a lipid-lowering agent and a weight reduction agent.

In addition, in accordance with the present invention, a method is provided for treating diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, atherosclerosis, and related diseases wherein a therapeutically effective amount of a compound of structure I is administered to a patient in need of treatment.

In addition, in accordance with the present invention, a method is provided for treating early malignant lesions (such as ductal carcinoma in situ of the breast and lobular carcinoma in situ of the breast), premalignant lesions (such as fibroadenoma of the breast and prostatic intraepithelial neoplasia (PIN), liposarcomas and various other epithelial tumors (including breast, prostate, colon, ovarian, gastric and lung), irritable bowel syndrome, Crohn's disease, gastric ulceritis, and osteoporosis and proliferative diseases such as psoriasis, wherein a therapeutically effective amount of a compound of structure I is administered to a patient in need of treatment.

In addition, in accordance with the present invention, a method is provided for treating diabetes and related diseases as defined above and hereinafter, wherein a therapeutically effective amount of a combination of a compound of structure I and another type antidiabetic agent and/or a hypolipidemic agent, and/or lipid modulating agent and/or other type of therapeutic agent, is administered to a human patient in need of treatment.

In the above method of the invention, the compound of structure I will be employed in a weight ratio to the antidiabetic agent (depending upon its mode of operation) within the range from about 0.01:1 to about 100:1, preferably from about 0.5:1 to about 10:1.

The conditions, diseases, and maladies collectively referenced to as "Syndrome X" or Dysmetabolic Syndrome (as detailed in Johanson, *J. Clin. Endocrinol. Metab.*, 1997, 82, 727–734, and other publications) include hyperglycemia and/or prediabetic insulin resistance syndrome, and is characterized by an initial insulin resistant state generating hyperinsulinemia, dyslipidemia, and impaired glucose tolerance, which can progress to Type II diabetes, characterized by hyperglycemia, which can progress to diabetic complications.

The term "diabetes and related diseases" refers to Type II diabetes, Type I diabetes, impaired glucose tolerance, obesity, hyperglycemia, Syndrome X, dysmetabolic syndrome, diabetic complications and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than compounds of formula I), one or more anti-obesity agents, and/or one or more lipid-lowering agents, one or more lipid modulating agents (including anti-atherosclerosis agents), and/or one or more antiplatelet agents, one or more agents for treating hypertension, one or more anti-cancer drugs, one or more agents for treating arthritis, one or more anti-osteoporosis agents, one or more anti-obesity agents, one or more agents for treating immunomodulatory diseases, and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

DETAILED DESCRIPTION OF THE INVENTION

PPARγ is a principal regulator of pre-adipocyte recruitment and differentiation into mature adipocytes (see Tontonoz et al., Current Biology, 571–576, 1995). Activators of PPARγ promote pre-adipocyte differentiation, lipid storage in mature adipocytes and act as insulin sensitizing anti-diabetic agents (see Tontonoz et al., Current Biology, 571–576, 1995; Lehmann et al., *J. Biol. Chem.*, 270: 12953–12956, 1995; Nolan et al. *New. Eng. J. Med.*, 331: 1188–1193; Inzucchi et al., *New Eng. J. Med.*, 338: 867–872, 1998, Willson, et al., *J. Med. Chem.*: 43: 527–550, 2000, Kersten et al., Nature, 405: 421424, 2000). The PPARγ induced anti-diabetic activity is however, frequently accompanied by some body weight gain in animal models and in humans. Recent findings suggest that that inhibition of PPARγ will lead to a reduction in adiposity and obesity (see Vidal-Puig et al., J. Clinical Investigation, 99: 2416–2422, 1997; Deeb et al Nature Genetics, 20:284–287, 1998; Kubota et al. Mol. Cell; 4:597–609, 1999; Barroso et al. Nature; 402, 860–861, 1999). However, such a reduction is likely to lead to higher plasma free fatty acids and hyperlipidemia and development fatty liver and insulin resistance. The PPARα isoform regulates genes in the fatty acid synthesis, fatty acid oxidation and lipid metabolism pathways (see Issenman and Green, *Nature,* 347: 645–649, 1990; Torra et al., *Current Opinion in Lipidology,* 10: 151–159, 1999; Kersten et al., Nature, 405: 421424, 2000). PPARα agonist (such as fenofibrate, gemfibrozil) treatment enhances fatty acid oxidation in the liver and muscle, reduces fatty acid and triglyceride synthesis in the liver, reduces plasma triglycerides (see Kersten et al., Nature, 405: 421424, 2000). In patients with high triglycerides and low HDL-cholesterol treatment with PPARα agonists leads to an increase in plasma HDL-cholesterol, decrease in plasma triglycerides and reduction of both 1° and 2° cardiac events (see Balfour et al., Drugs. 40: 260–290, 1990; Frick et al., *New Eng. J. Med.,* 317: 1237–1245; Rubins et al., *New Eng. J. Med.,* 341: 410–418, 1999). Therefore, by combining PPARγ antagonist activity and PPARα agonist activity in a single dual acting compound or a combination of a PPARγ antagonist and a PPARα agonist it is possible to safely inhibit PPARγ and treat obesity without causing hyperlipidemia, fatty liver and insulin resistance.

Figure 1A:
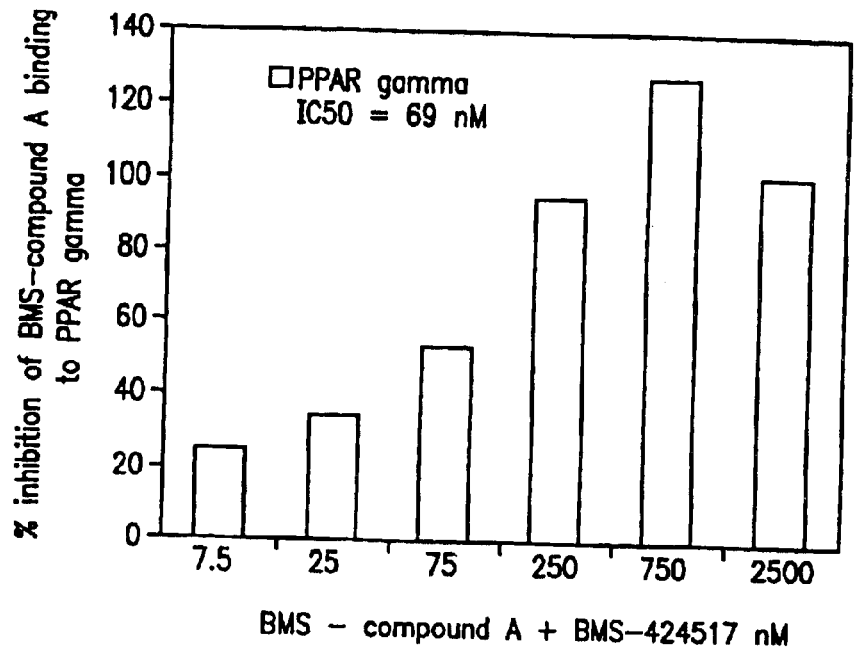
FIG. 1A: Illustrates the ability of Compound Y to competitively inhibit the binding of a labeled authentic PPARγ ligand (BMS-compound A) to human PPARγ ligand binding domain.
Figure 1B:
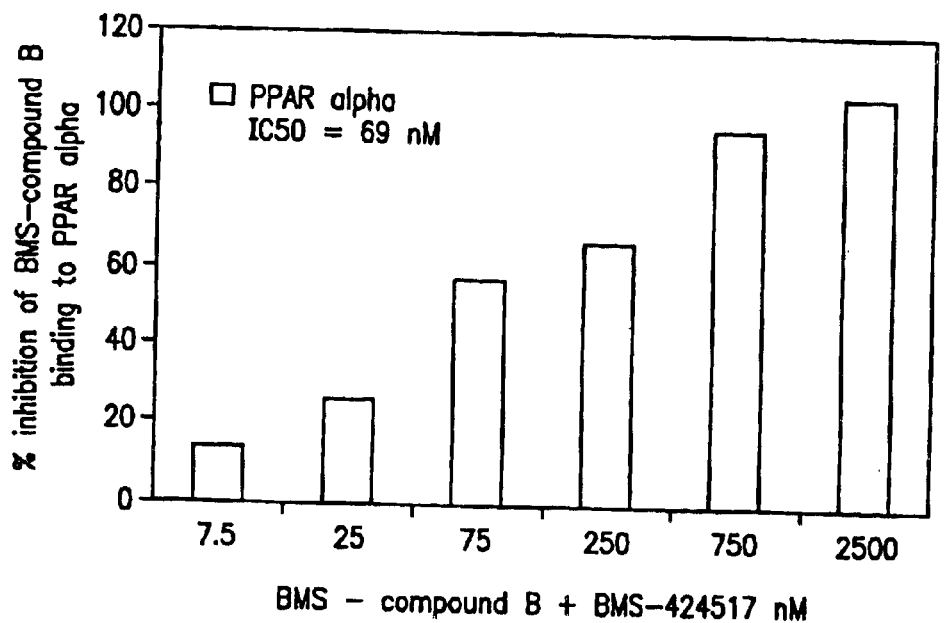
FIG. 1B: Illustrates the binding of a labeled authentic PPARα ligand (BMS-compound B) to human PPARα binding domain.

Compound Y is a compound synthesized by the scheme outlined in Example 1 herein. As illustrated in FIGS. 1-A, 1-B, Compound Y potently bound to human PPARγ ligand binding domain with high affinity ($IC_{50}$=69 nM). Similarly, Compound Y also potently bound to purified human PPARα ligand binding domain ($IC_{50}$=69 nM). In related PPARγ ligand binding studies, the $IC_{50}$=250 nM for rosiglitazone (an authentic PPARγ agonist) and the $IC_{50}$=280 nM for GW0072 (an authentic PPARγ antagonist) were obtained. In PPARα ligand binding studies, the $IC_{50}$=410 nM for GW-2331 (a PPARα selective agonist) was obtained. The in vitro ligand binding studies with purified ligand binding domain thus show the ability of Compound Y to bind potently to both PPARγ and PPARα. It is however, well known for the nuclear hormone receptor family of transcription factors that (PPARs are members of this family) that a compound which potently binds to (i.e. a ligand) can act as an agonist (ligand which activates) and an antagonist (ligand which inactivates the receptor).

Figure 2:
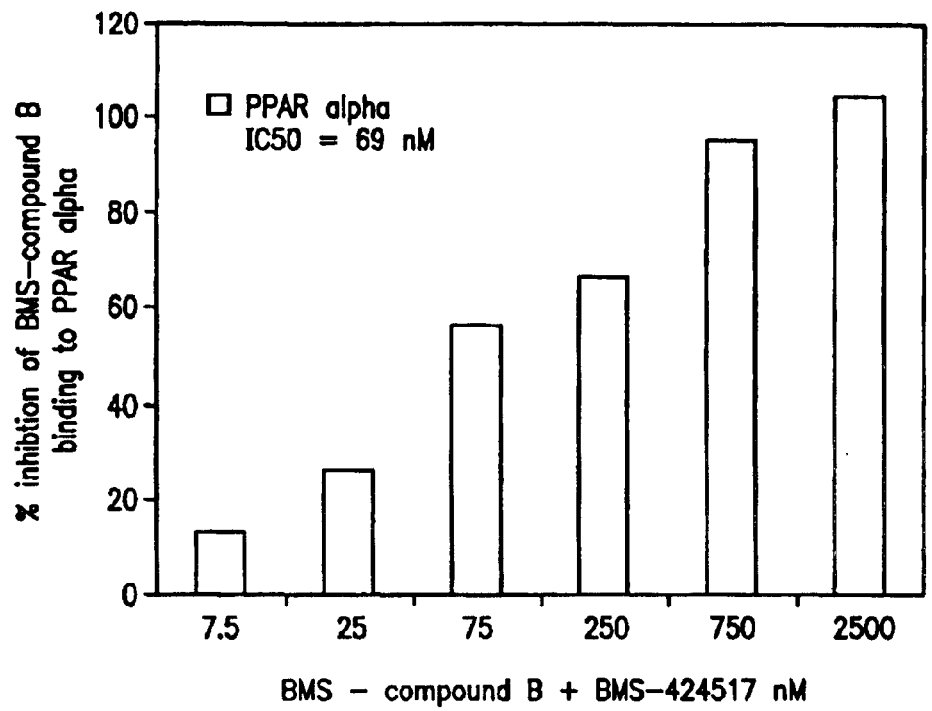
FIG. 2: Illustrates the ability of Compound Y to competitively inhibit authentic PPARγ agonist (e.g. rosiglitazone) dependent differentiation of mouse 3T3L-1 pre-adipocytes (immature fat cells) into lipid loaded mature adipocytes (mature fat cells).

As illustrated in FIG. 2, Compound Y when added to mouse pre-adipocyte cells 3T3L-1 shows competitive inhibition of rosiglitazone (a PPARγ agonist) induced differentiation into mature lipid loaded adipocytes (as measured by glycerol release from the cells). Mouse 3T3-L-pre-adipocytes have been known to respond to hormonal signals (such as insulin, dexamethazone) and PPARγ agonists (such as rosiglitazone) and differentiate into mature adipocytes and accumulate lipids. PPARγ has been considered a major trigger for the adipocyte differentiation process (see Tontonoz et al., Current Biology, 571–576, 1995). Although, Compound Y is a potent ligand for PPARγ, it shows competitive inhibition of rosiglitazone induced differentiation, suggesting therefore that it is an antagonist of PPARγ. The $ED_{50}$ for inhibition of differentiation=9.9 μM shows Compound Y is a moderate inhibitor of pre-adipocyte differentiation. In comparison the $ED_{50}$=0.585 μM was obtained for GWO072, an PPARγ antagonist ((see Oberfield et al, Proc. Nat. Acad. Sci., 96: 6102–6106, 1999).

Figure 3:
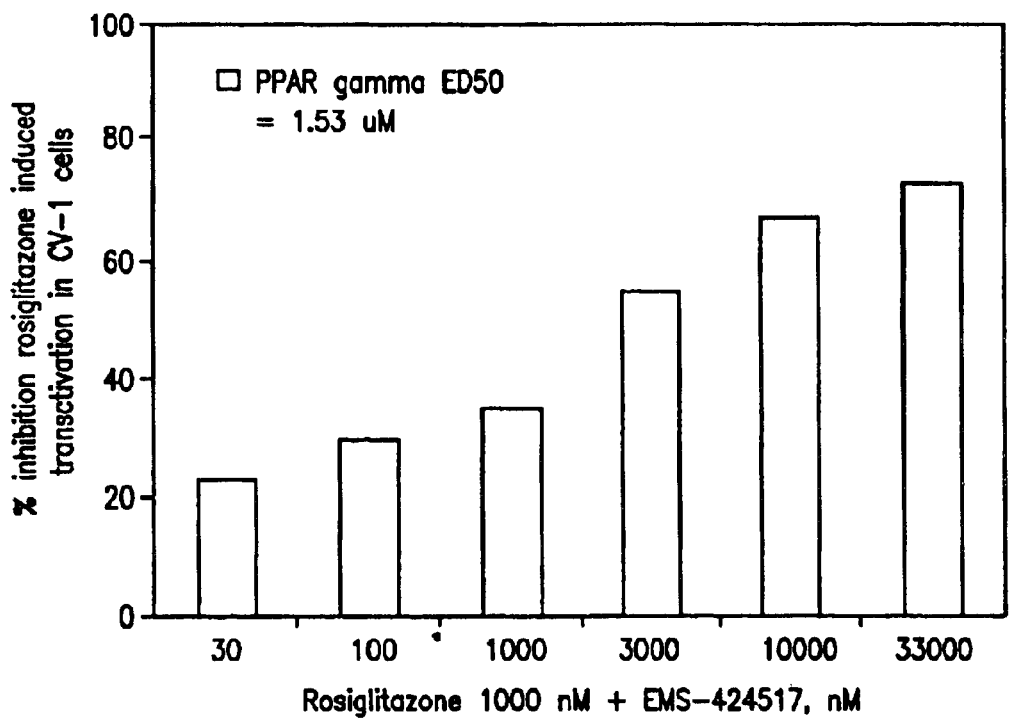
FIG. 3: Illustrates the ability of Compound Y to competitively inhibit authentic PPARγ agonist (e.g. rosiglitazone) dependent activation of secreted alkaline phosphatase (SEAP) reporter gene expression in primate kidney cells CV-1.

As illustrated in FIG. 3 the PPARγ antagonist activity of Compound Y was verified in a second cell line. The established CV-1 cells (primate kidney origin), that show expression of endogenous PPARγ, were stably transfected with a PPAR responsive secreted alkaline phosphatase (SEAP) reporter gene. As with previous study, Compound Y was competitively inhibited rosiglitazone (a PPARγ agonist) dependent activation, namely induction of SEAP reporter gene expression in CV-1 cells. The $ED_{50}$=1.5 μM for specific inhibition of rosiglitazone induced transactivation of SEAP gene shows once again, Compound Y is an antagonist of PPARγ. In the study GW0072, a PPARγ antagonist (see Oberfield et al, Proc. Nat. Acad. Sci., 96: 6102–6106, 1999) also dose dependently inhibited rosiglitazone mediated induction of SEAP gene in CV-1 cells with an $ED_{50}$=0.37 μM for inhibition and verified the reliability of data.

Figure 4:
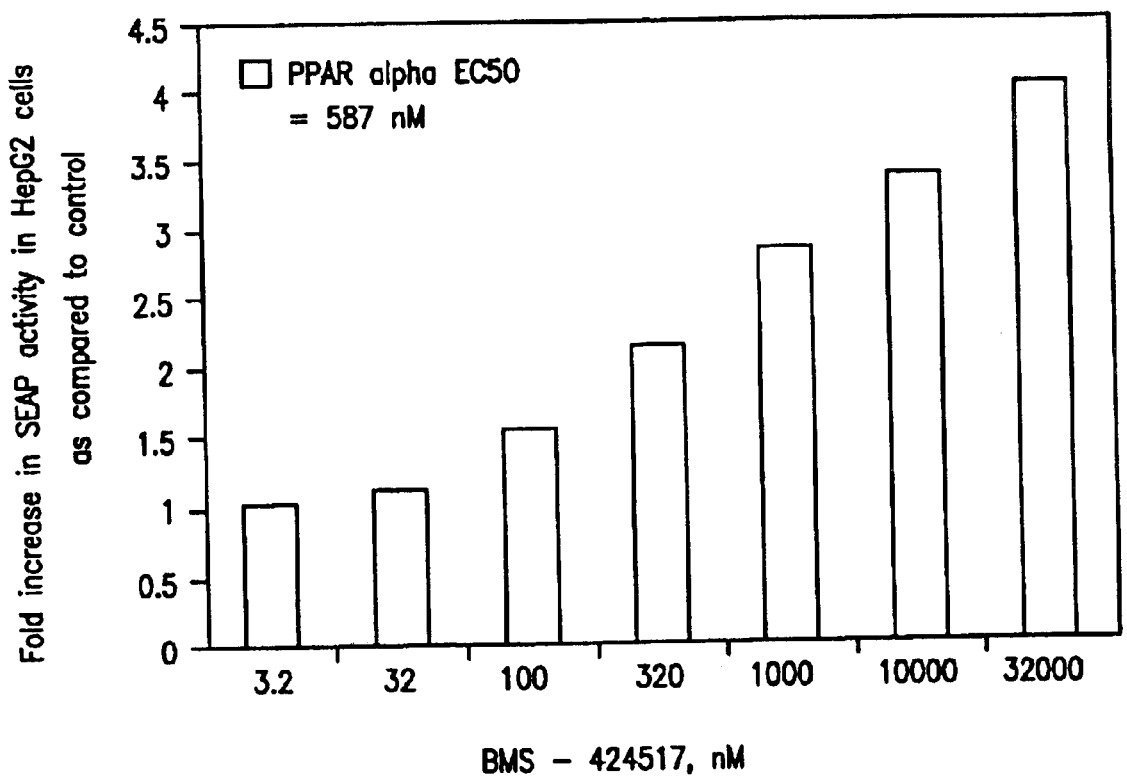
FIG. 4: Illustrates the ability of Compound Y to dose dependently stimulate PPARα dependent SEAP reporter gene activity in human liver cell line HepG2 (this cell line shows significant amounts of PPARα) with a stably integrated PPARα dependent SEAP reporter.

As illustrated in FIG. 4 Compound Y dose dependently stimulated PPARα dependent transactivation of SEAP reporter gene in human liver cells HepG2, showing thereby that it is an agonist of PPARα. HepG2 cells (human liver origin), that express endogenous PPARα gene were stably transfected with a PPAR responsive SEAP reporter gene. Upon treatment, Compound Y dose dependently stimulated SEAP gene expression in HepG2 cells with an $EC_{50}$ for PPARα transactivation=0.587 μM. In this study BMS-250773 (a PPARα selective agent) dose dependently stimulated PPARα dependent transactivation of SEAP reporter gene with an $EC_{50}$=0.063 μM and rosiglitazone (a PPARγ agonist) showed very little activation.

Thus, the in vitro PPARγ and PPARα ligand binding studies and PPARγ and PPARα dependent cell based transactivation studies described in FIGS. 1, 2, 3,4 show Compound Y is a potent ligand for both PPARγ and PPARα, however, it shows antagonist activity towards PPARγ and agonist activity towards PPARα. These findings indicate Compound Y belongs to a novel class of molecules which possess both (dual) PPARγ antagonist activity and PPARα agonist activity in a single molecule.

TABLE 1

| Gene expression in WAT | Rosiglitazone γ agonist | BMS-compound C Dual α/γ agonist | Compound Y Dual γ antagonist/ α agonist | Comments/Likely outcome |
|---|---|---|---|---|
| HMGic | NC | NC | 2.2 | PPAR γ antagonist effect |
| | | | | Reduced adipocyte differentiation |
| Glycerol-3 PO4 dehydrogenase | NC | NC | 0.39 | PPAR γ antagonist effect |
| | | | | Reduced adipocyte differentiation |
| Fatty acid transport protein | 2.5 | 3.7 | NC | PPAR γ antagonist effect |
| | | | | No change in FA transport into cell |
| G-protein coupled receptor 26 | 4.3 | 19.2 | NC | PPAR γ antagonist effect |
| | | | | Play a role in adipocyte differentiation |
| Adipophilin | NC | 9.6 | 4.1 | PPAR α agonist effect |
| | | | | Increased FA mobilization in cytoplasm |
| Keratinocyte fatty acid binding protein | NC | 2.6 | 3.3 | PPAR α agonist effect |
| | | | | Increased FA retention in cytoplasm |

As illustrated in Table 1, Compound Y shows both PPARγ antagonist and PPARα agonist effects at the level of expression of several genes in vivo. In order to demonstrate the in vivo PPARγ antagonist and PPARα agonist effect of Compound Y, obese diabetic db/db mice were treated with Compound Y, rosiglitazone (an authentic PPARγ agonist) and BMS-compound C (this compound possess agonist activity towards both PPARα and PPARγ. At the termination of the study white adipose tissue (WAT) was harvested, total RNA prepared and analyzed for effect on target gene expression. These analyses demonstrated that a number of genes whose expression is specifically altered by Compound Y treatment and confirmed the in vivo PPARγ antagonist activity of Compound Y. For example expression of (1) HMGic which prevent adipocyte differentiation is induced by Compound Y and not by rosiglitazone or BMS-compound C, (2) glycerol3-$PO_4$ dehydrogenase which promote adipocyte differentiation is inhibited by Compound Y and not by rosiglitazone and BMS-compound C, (3) fatty acid transport protein which promote fatty acid transport into the cell remained unaffected by Compound Y was, however, induced by rosiglitazone and BMS-compound C and (4) an orphan GPCR 26 which is related to the bombesin receptor remained unaffected by Compound Y was induced by rosiglitazone and BMS-compound C. These analyses also demonstrated a number of other genes whose expression is induced only by Compound Y and BMS-compound C and not by rosiglitazone confirming PPARα agonist activity of Compound Y in vivo. Examples of such genes include adipophilin and keratinocyte fatty acid binding protein, the gene products of these genes are involved in intracellular fatty acid trafficking).

Thus the gene expression profiling studies confirm the in vivo PPARγ antagonist and PPARα agonist activity of the dual PPARγ antagonist/PPARα agonist Compound Y. Furthermore, these studies also show a method for treating obesity by changing genes which affect adipocyte differentiation such as HMGic, glycerol 3-$PO_4$ dehydrogenase, fatty acid transport protein and the novel orphan G-protein coupled receptor 26 levels, in adipose (fat) tissue through administration of PPARγ antagonists and or dual PPARγ antagonist/PPARα agonists. These studies also show a method for treating obesity by changing adipophilin and keratinocyte fatty acid binding protein levels in adipose (fat) tissue through administration of PPARα agonist and or dual PPARγ antagonist/PPARα agonist.

with a dual PPARγ antagonist/PPARα agonist such as Compound Y.

TABLE 3

| Treatment | Glucose (mg/dL) | Triglyceride (mg/dL) | Free fatty acids (meq/L) |
|---|---|---|---|
| Vehicle | 780.9 ± 43.8 | 265.2 ± 34.3 | 1.18 ± 0.06 |
| Compound Y (3 mg/kg/day) | 683.0 ± 25.2 −13% | 145.3 ± 12.5 −45%* | 0.76 ± 0.12 −36%* |

*$p < 0.05$

As illustrated in Table 3 treatment of obese diabetic db/db mice with the dual PPARγ antagonist/PPARα agonist Compound Y results in no significant change in plasma glucose and a significant decrease in plasma triglycerides and free fatty acids levels. As indicated before, changes in lipid and glycemic conditions are two significant potential concerns of reducing PPARγ activity. Based on the study described here it is concluded that obese mammals can be safely treated with a dual PPARγ antagonist/PPARα agonist. The reduction in plasma triglycerides and free fatty acids are likely due to the PPARγ agonist activity of Compound Y.

TABLE 2

| Gene expression in WAT | Rosiglitazone γ agonist | BMS-compound C Dual α/γ agonist | Compound Y Dual γ antagonist/ α agonist | Comments/ Likely outcome of PPARγ antagonist effect |
|---|---|---|---|---|
| PAI-1 | NC | NC | 0.45 | PPAR γ antagonist effect Reduced risk for thrombosis |
| Angiotensinogen precursor | NC | NC | 0.46 | PPAR γ antagonist effect Lower angiotensinogen I/II level Reduced risk for hypertension |
| Renin | 13.9 | 2.1 | NC | PPAR γ agonist effect No change in angiotensinogen I/II level No change in risk for hypertension |

As illustrated in Table 2, expression profiling analysis of white adipose tissue (WAT) of obese diabetic db/db mice treated with dual PPARγ antagonist/PPARα agonist Compound Y shows substantial beneficial changes in the expression of several genes which are known to play a role in the development of cardiovascular disease. Adipose (fat) tissue is a major place of synthesis of PAI-1, a risk factor for thrombosis, angiotensinogen precursor, a risk factor for hypertension and renin, a risk factor for hypertension (see Ahima and Flier, TEM, 11: 327–332, 2000). The inhibition of PAI-1 and angiotensinogen precursor gene expression and absence of a change in the expression of renin gene, selectively with Compound Y confirms once again the PPARγ antagonist activity, and shows the cardiovascular beneficial effects of treatment of obese mammals including human

TABLE 4

| Treatment | % Fat body mass | % Lean body mass |
|---|---|---|
| Vehicle | 47.2 ± 1.5 | 50.5 ± 1.4 |
| Compound Y (10 mg/kg/day) | 41.5 ± 1.8 (−12%)* | 56.0 ± 1.8 (+11%)* |

*$P < 0.05$

As illustrated in Table 4, treatment of diet induced obese mice with dual PPARγ antagonist/PPARα agonist Compound Y for 3 weeks at 10 mg/kg/day, once a day resulted in a significant 15% reduction of body fat mass and a corresponding 14% increase in lean body mass indicating to the beneficial effect of Compound Y. Reduction in fat mass upon treatment with dual PPARγ antagonist/PPARα agonist Compound Y is most likely due to the result of inhibition of PPARγ activity leading to reduced adipocyte (fat cell) expansion and reduced accumulation of fat mass. Although, no significant reduction in body weight is observed in this study, reduced fat mass and compensating increase in lean body mass (such a compensation is not observed in human lipodystrophic patients with defects in fat tissue accumulation) represent a significant beneficial effect of treatment with dual PPARγ antagonist/PPARα agonist Compound Y. It is possible that PPARα agonist activity contributes to the increase in lean muscle mass build up, possibly through induction of fatty acid metabolism pathway genes and or through induction muscle protein synthesis by an unknown mechanism.

TABLE 5

| Treatment | Cholesterol (mg/dL) | Triglyceride (mg/dL) | Glucose (mg/dL) | Insulin (ng/ml) |
| --- | --- | --- | --- | --- |
| Vehicle | 281.8 ± 26.5 | 95.1 ± 7.2 | 241.4 ± 12.8 | 9.7 ± 1.5 |
| Compound Y (10 mg/kg/day) | 270.4 ± 9.4 | 105.5 ± 8.1 | 260.7 ± 12.3 | 8.2 ± 1.2 |

As illustrated in Table 5 treatment of diet induced obese mice with the dual PPARγ antagonist/PPARα agonist Compound Y resulted in very little change in plasma lipid (free fatty acids, triglycerides and cholesterol) and glycemic (glucose and insulin) parameters. As indicated before, changes in lipid and glycemic conditions are two potential concerns of reducing PPARγ activity. Based on the study described here it is concluded that safe reduction of fat mass in an obese diabetic mammal (including human) is possible through administration of a dual PPARγ antagonist/PPARα agonist. This feature is in contrast to the observed hyperlipidemia and hyperglycemia in lipodystrophic patients and in patients with severe mutations in PPARγ gene.

TABLE 6

| Treatment | Liver triglycerides (mg/g) | ALT (IU/L) |
| --- | --- | --- |
| Vehicle | 72.5 ± 4.8 | 158.8 ± 20.2 |
| Compound Y (10 mg/kg/day) | 55.4 ± 7.0 (−24%) | 98.0 ± 12.6 (−38%)* |

*P < 0.05

As illustrated in Table 6, treatment of diet induced obese mice with the dual PPARγ antagonist/PPARα agonist Compound Y results in an improvement in liver phenotype. In obese mice, as in obese human, the liver lipid level is elevated. Often, this is accompanied by an increase in plasma liver enzyme ALT level indicating to liver damage. Upon treatment with dual PPARγ antagonist/PPARα agonist Compound Y there was a substantial reduction in liver triglyceride content, although not reaching statistical significance, which was accompanied by a significant reduction in plasma liver enzyme ALT levels. Both these changes are indicative of improvement in liver function as a result of stimulation of PPARα mediated fatty acid oxidation and reduction of lipid synthesis leading to reduced lipid content (see. Torra et al., *Current Opinion in Lipidology*, 10: 151–159, 1999; Kersten et al., Nature, 405: 421424, 2000).

The present invention therefore shows the discovery of a novel dual acting PPARγ antagonist/PPARα agonist agent. This invention provides a pharmacological proof of principle for treating obesity through the administration of a dual PPARγ antagonist/PPARα agonist. In accordance with this invention, combining PPARγ antagonist activity and PPARα agonist activity in a single molecule or combining PPARγ antagonist activity and PPARα agonist activity in a medicament, will offer treatment of obesity without any further deterioration of lipid and or glycemic control in obese individuals.

This invention presents the identity of a list of genes whose expression is modified to achieve anti-obesity (such as HMGic, glycereol-PO$_4$ dehydrogenase, fatty acid transport protein, G-protein coupled receptor 26, adipophilin, keratinocyte fatty acid binding protein) and cardiovascular (such as angiotensinogen, PAI-1, renin) benefits through treatment by a PPARγ antagonist, or a dual PPARγ antagonist/PPARα agonist or a PPARα agonist.

This invention also presents a method for treating liver dysfunction through the administration of a dual PPARγ antagonist/PPARα agonist or PPARα agonist.

The present invention also provides a method for treating obesity, in mammals, including human, through administration of a pharmacological composition containing a single agent or a combination of two agents which will simultaneously reduce: (1) the activity of PPARγ protein, or (2) expression of the PPARγ gene, (3) binding of a co-activator or (4) expression of PPARγ regulated target genes (or any combination of the above) and increase (1) the activity of PPARα protein, or (2) expression of the PPARα gene, or (3) binding of a co-activator or (4) expression of PPARα regulated target genes (or any combination of the above). The resulting product of these changes may include any combination of (but are not limited to): (1) prevention of weight gain, (2) weight loss, (3) specific reduction fat mass, (4) increase in lean body mass (5) change in body fat mass/lean mass ratio, (7) reduction of liver lipid and improvement in liver function.

The present invention also provides a treatment method involving the use of a combination of a dual PPARγ antagonist/PPARα agonist with anti-diabetic agents such as but not limited to metformin, sulfonylurea, insulin, insulin sensitizers, aP2 inhibitor, SGLT2 inhibitor, agents that affect liver glucose output, a lipid lowering agent such as a PPARα agonist (such as but not limited to fenofibrate and gemfibrozil) and a HMG-CoA reductase inhibitor (such as, but not limited to, pravastatin, lovastatin, simvastatin and atorvastatin), niacin, ACT inhibitors, LCAT activators, bile acid sequestering agents and other anti-obesity agents (such as, but not limited to, orlistat, sibutramine, aP2 inhibitor, adiponectin) to control body weight, insulin resistance, Type 2 diabetes, hyperlipidemia and cardiovascular diseases in obese patients.

The compounds of the formula I of the present invention may be prepared according to the following general synthetic schemes, as well as relevant published literature procedures that are used by one skilled in the art. Exemplary reagents and procedures for these reactions appear hereinafter and in the working Examples. Protection and deprotection in the Schemes below may be carried out by procedures generally known in the art (see, for example, Greene, T. W. and Wuts, P. G. M., Protecting Groups in Organic Synthesis, 3$^{rd}$ Edition, 1999 [Wiley]).

The synthesis of key intermediates required for the synthesis of the compounds of the invention are described in Scheme 1. An alcohol 1 (R$^5$(CH$_2$)$_x{}^2$OH) (of which one of the most favored is 2-phenyl-5-methyl-oxazole-4-ethanol) is coupled with a hydroxy aryl- or heteroaryl-aldehyde 2 under standard Mitsunobu reaction conditions (e.g. Mitsunobu, O., *Synthesis*, 1981, 1) to furnish the key intermediate aldehyde 3. Alternatively, the alcohol 1 can be converted to its methanesulfonate ester 4 under standard conditions; the mesylate 4 can then be used to alkylate the hydroxy aryl- or heteroaryl-aldehyde 2 to furnish the aldehyde 3.

Scheme 2 describes a general synthesis of 2-aryl (heteroaryl) 4-carboxy-triazoles I. Treatment of a suitably protected oxybenzoic or oxyphenylacetic acid chloride 5 with Meldrum's acid in the presence of base provides the corresponding crude Meldrum's acid adduct 6 which is immediately reacted with aniline to give the β-keto anilide 7 (*Synthesis*, 1992, 1213–1214). The β-keto amide 7 is reacted with nitrous acid (generated in situ from base/sodium nitrite) followed by acid treatment to furnish the corresponding α-oxime β-keto amide 8 (Reference: Hamanaka, E. S., et al, WO9943663). The β-keto-amide 8 is then condensed with an appropriately substituted hydrazine 9 to provide the corresponding β-hydrazone-amide 10. Treatment of intermediate 10 with acid furnishes the desired 2-substituted 4-carboxamido-triazole 11 (Reference: Hamanaka, E. S., et al, WO9943663). Deprotection of the phenolic protecting group of triazole-anilide 11 furnishes the corresponding phenol 12. The phenol-triazole 12 is then coupled with an appropriate alcohol 1 under standard Mitsunobu reaction conditions (e.g. Mitsunobu, O., *Synthesis*, 1981, 1) to furnish the desired alkylated triazole-amide 13. Alternatively, the phenol can be coupled with the methanesulfonate ester 4 under basic conditions to furnish the alkylated triazole-amide 13 (Reference: Cheng, P. T. W., et. al., WO0121602). Subsequent base-mediated deprotection of this anilide furnishes the desired 2-substituted 4-carboxy triazole II of the invention.

Scheme 3 illustrates a complementary approach to that shown in Scheme 2 for the preparation of 2-aryl 4-carboxy triazoles I. An appropriately protected hydroxyaryl or hydroxyheteroaryl carboxylic acid 14 is treated either with: 1) mesylate 4 in the presence of base or 2) alcohol 1 under standard Mitsunobu conditions to furnish, after deprotection of the carboxylic acid, the key alkylated acid intermediate 15. Conversion of acid 15 to the corresponding acid chloride 16 is achieved using oxalyl chloride. Treatment of acid chloride 16 with Meldrum's acid furnishes the corresponding adduct 17, which is then immediately reacted with aniline to provide the β-keto anilide 18. Treatment of the β-keto anilide 18 with nitrous acid (generated in situ from base/NaNO₂) then furnishes the corresponding β-keto α-oximino-anilide 19, which is then reacted with an appropriately substituted hydrazine 9 to provide the intermediate β-hydrazone-amide 20. Acid-mediated cyclization of the oxime-hydrazone 20 then gives the aryltriazole anilide 21. Finally, base-mediated hydrolysis of the anilide furnishes the desired 2-substituted 4-carboxytriazole IIA of the invention.

Scheme 4 describes the synthesis of 1-substituted 4-carboxytriazoles II. Treatment of β-keto anilide 18 with p-toluenesulfonyl azide (Padwa, A., et al, *J. Org. Chem.*, 1997, 62, 6842) furnishes the corresponding β-keto α-diazo-anilide 21. Lewis acid-mediated reaction of the β-keto α-diazo-anilide 21 with an appropriately substituted amine 22 furnishes the corresponding 1-substituted-4-amido triazole 23 (Ohno, M., et al, *Synthesis*, 1993, 793). Deprotection of the phenol functionality of triazole-anilide 23 furnishes the phenol 23. Alkylation of the phenol-triazole 23 is then achieved with alcohol 1 under standard Mitsunobu reaction conditions (e.g. Mitsunobu, O., *Synthesis*, 1981, 1) to furnish the corresponding alkylated triazole-amide.

Alternatively, the phenol-triazole 23 can be coupled with the methanesulfonate ester 4 under basic conditions to furnish the same alkylated triazole-amide. Subsequent base-mediated deprotection of carboxylic acid furnishes the desired 1-substituted-4-carboxy triazole III of the invention.

Scheme 5 describes the synthesis of the regioisomeric 1-substituted-5-carboxy triazoles III and 1-substituted-4-carboxy triazoles IV. Aldehyde 3 is reacted with an appropriately protected propargylic acid under basic/anionic conditions (*J. Org. Chem.*, 1980, 45, 28) to furnish the corresponding acetylenic alcohol adduct 25. The acetylenic alcohol 25 is then deoxygenated under standard literature conditions (Czernecki, S., et al, *J. Org. Chem.*, 1989, 54, 610) to give the acetylenic ester 26. Dipolar cycloaddition of the acetylenic ester 26 with an appropriately substituted aryl azide 27 under thermal conditions (*Can. J. Chem.*, 1980, 58, 2550) furnishes, after deprotection of the carboxylic acid functionality, the desired aryl triazole acids IV and V of the invention.

Scheme 6 shows a slightly altered sequence for the preparation of triazole acids IV and V as well as the hydroxy triazole acids VI and VII. The acetylenic alcohol adduct 25 can immediately undergo the dipolar cycloaddition reaction with the appropriately substituted azide 27 under thermal conditions to give the corresponding regioisomeric hydroxy triazole esters 28 and 29, which are then deprotected to provide the hydroxy triazole acids VI and VII respectively, of the invention. Alternatively, the hydroxy triazole esters 28 and 29 undergo deoxygenation and deprotection reactions to furnish the triazole acids IV and V of the invention.

Scheme 7 describes the synthesis of 1-substituted 4-carboxypyrazoles VIII. A protected phenol-alcohol 30 is converted to the corresponding chloride 31 by standard literature methods (*Tetrahedron Lett.*, 1986, 42, 2725). A protected cyanoacetate 32 is then alkylated with chloride 31 in the presence of base to provide the cyanoacetate 33. Deprotection of the cyanoacetate 33 furnishes the cyanoacetic acid 34. Treatment of cyanoacetic acid 34 with an appropriately substituted hydrazine 9 in the presence of nitrous acid (generated in situ from sodium nitrite and acid) provides the corresponding cyano-hydrazone 35 (Skorcz, J. A., et al, *J. Med. Chem.*, 1966, 9, 656). Reaction of cyano-hydrazone 35 with an appropriately protected acrylate 36 in the presence of base (Kim, Y. H., et al, *Tetrahedron Lett.*, 1996, 37, 8771) gives the key aryl-pyrazole ester intermediate 37. A three-step sequence involving: 1) removal of the phenolic protecting group of pyrazole 37, 2) alkylation of the resulting phenol with mesylate 4 under basic conditions and 3) deprotection of the carboxylic acid furnishes the 1-aryl 3-substituted 4-carboxypyrazole VIII of the invention.

Scheme 8 illustrates the synthesis of the regioisomeric 1-substituted 5-substituted 4-carboxypyrazoles IX. The protected phenol-acid chloride 5 is treated with Meldrum's acid under basic conditions to give the corresponding adduct, which is reacted with an appropriate alcohol R₃OH to provide the β-ketoester 38. Treatment of the β-keto-ester 38 with dimethyl formamide dimethyl acetal (Almansa, C., et al, *J. Med. Chem.*, 1997, 40, 547) gives the α-enamino-β-keto-ester 39. Reaction of the α-enamino-β-keto-ester 39 with an appropriately substituted hydrazine 9 followed by intramolecular cyclization furnishes the aryl-N-pyrazole ester 40. A three step sequence: 1) removal of the phenolic protecting group of 40, 2) alkylation of the resulting phenol with mesylate 4 and 3) deprotection of the carboxylic acid furnishes the N-substituted pyrazole acid IX of the invention.

A synthesis of the regioisomeric carboxypyrazoles X is shown in Scheme 9. Treatment of aldehyde 3 (with an appropriately substituted alkynylmetal reagent 41) furnishes the acetylenic alcohol adduct 42. Alcohol 42 is then treated with ketene dimer under thermal conditions (Kato, T., et al, *Chem. Pharm. Bull.*, 1975, 20, 2203) to provide the acetoacetate ester 43. Chlorination of acetoacetate ester 43 under standard conditions (reference) furnishes the α-chloro, β-ketoester 44. Treatment of the α-chloro, β-ketoester 44 with an appropriately substituted diazo compound 45 under thermal conditions furnishes the chlorohydrazone 46 (Garantic, L., et al, *Synthesis*, 1975, 666). Base-mediated thermal intramolecular cycloaddition of chlorohydrazone 46 (Garantic, L., et al, *Synthesis*, 1975, 666) then furnishes the pyrazole-lactone 47. Concomitant ring-opening/deoxygenation of the pyrazole-lactone 47 is achieved under a number of different reaction conditions (TMSCl/NaI or Zn/NH$_4$OH; Sabitha, G., *Synth. Commun.*, 1998, 28, 3065) to furnish the pyrazole acid 48. A three step sequence: 1) removal of the phenolic protecting group of 48, 2) alkylation of the resulting phenol with mesylate 4 and 3) deprotection of the carboxylic acid furnishes the N-substituted pyrazole acids X of the invention.

A general route to the N-substituted pyrrole 3-carboxylic acids XI is shown in Scheme 10. The aldehyde 3 is reacted under basic conditions with an appropriately protected propiolate ester 49 ((*J. Org. Chem.*, 1980, 45, 28) to provide the alkyne-alcohol 50. Deoxygenation of the alcohol functionality of alkyne 50 using standard methods (e.g. Et$_3$SiH/acid; *Tetrahedron Lett.*, 1987, 28, 4921) provides the alkynoate ester 51. Reduction of the alkynoate ester 51 using standard methods ("Preparation of Alkenes, A Practical Approach", J. M. J. Williams, Ed., Chapter 6, "Reduction of Alkynes", J. Howarth. Oxford University Press, 1996) furnishes the Z-alkenyl ester 52. The α,β unsaturated ester 52 is then reacted with tosylmethyl isocyanate (TosMIC) under standard literature conditions (Van Leusen, A. M., et al, *Tetrahedron Lett.*, 1972, 5337) to give the corresponding pyrrole-ester 53. Coupling of the pyrrole-ester 53 with an appropriately substituted aryl or heteroaryl boronic acid 54 using standard literature conditions (Lam, P. Y. S., et al, *Tetrahedron Lett.*, 1998, 39, 2941) furnishes the N-substituted pyrrole ester 55. Deprotection of the N-substituted pyrrole ester 55 then provides the N-substituted pyrrole acid XI of the invention.

Scheme 11 illustrates a synthetic route to N-substituted pyrrole 3-carboxylic acids XII. The aldehyde 3 undergoes a Wittig reaction with a phosphoranylidene ester 53 ("Preparation of Alkenes, A Practical Approach", J. M. J. Williams, Ed., Chapter 2, "The Wittig reaction and related methods", N. J. Lawrence, Oxford University Press, 1996) or a Horner-Emmons reaction with a phosphonate ester 56 (J. M. J. Williams, supra and N. J. Lawrence, supra) to give the predominantly E-alkenyl ester 57. The E-alkenyl ester 57 is then reacted with tosylmethyl isocyanate (TosMIC) to provide the pyrrole-ester 58. Pyrrole-ester 58 is then reacted with appropriate boronic acid 54 under standard literature conditions (Evans reference) to provide the corresponding N-substituted pyrrole ester 59. Deprotection of N-substituted pyrrole ester 59 then gives the N-substituted pyrrole acid XII of the invention.

Scheme 12 shows the preparation of the required intermediate 2-aryl (or 2-heteroaryl)-5-methyl-oxazol-4-yl methyl chloride (following the general procedure described in Malamas, M. S., et al, *J. Med. Chem.*, 1996, 39, 237–245). A substituted aldehyde 60 is condensed with butane-2,3-dione mono-oxime under acidic conditions to give the corresponding oxazole N-oxide 61. Deoxygenation of the oxazole N-oxide 61 with concomitant chlorination furnishes the desired chloromethyl aryl (or heteroaryl)-oxazole 62. Hydrolysis of chloromethyl oxazole 62 under basic conditions furnishes the corresponding oxazole-methanol 63. Oxidation of alcohol 63 to the corresponding aldehyde is followed by conversion to the corresponding dibromoalkene 64 (e.g. Ph$_3$P/CBr$_4$). The dibromide 64 is converted to the corresponding alkynyl-lithium species (using an organo-lithium reagent such as n-BuLi), which can be reacted in situ with an appropriate electrophile such as formaldehyde to give the corresponding acetylenic alcohol (ref: Corey, E. J., et al., *Tetrahedron Lett.* 1972, 3769, or Gangakhedkar, K. K., *Synth. Commun.* 1996, 26, 1887–1896). This alcohol can then be converted to the corresponding mesylate 65 and alkylated with an appropriate phenol 66 to provide, after deprotection of the carboxylic acid, analog XIII. In general, phenol 66 is obtained by deprotection of the phenol functionality of appropriate intermediates such as 11, 23 and 37. Stereoselective partial reduction of alkyne XIII of the invention (e.g. H$_2$/Lindlar's catalyst) provides the E- or Z-alkenyl analog XIV. Complete reduction of alkene analog XIV (hydrogenation) provides the alkyl analog XV of the invention. Alternatively, complete reduction (e.g. H$_2$/Palladium on Carbon catalyst) of alkyne analog XIII of the invention also provides the alkyl analog XV of the invention.

The synthesis of carbon-linked analogs XVI, XVII, and XVIII are shown in Schemes 13–14. The synthetic sequence is analogous to that shown in Scheme 2. Treatment of a suitably protected halo-aryl (or heteroaryl) acid chloride 67 with Meldrum's acid in the presence of base provides the corresponding crude Meldrum's acid adduct 68 which is immediately reacted with aniline to give the β-keto anilide 69. The β-keto amide 69 is reacted with nitrous acid (generated in situ from base/sodium nitrite) followed by acid treatment to furnish the corresponding a-oxime β-keto amide 70. The β-keto-amide 70 is then condensed with an appropriately substituted hydrazine 9 to provide the corresponding β-hydrazone-amide 71. Treatment of intermediate 71 with acid furnishes the desired 2-aryl 4-carboxamidotriazole 72. Coupling of the alkyne 73 with halo-triazole 72 under standard Sonogashira reaction conditions (e.g. "Organocopper Reagents, a Practical Approach", R. J. K. Taylor, E., Chapter, 10, p 217–236, Campbel, I. B., Oxford University Press, 1994) furnishes the corresponding alkynyl triazole 74. Hydrolysis of the anilide 74 then provides the alkynyl triazole acid analog XVI of the invention. Selective reduction of the alkynyl triazole acid XVI of the invention (e.g. H$_2$/Lindlar catalyst) provides the E- or Z-alkenyl triazole acid XVII of the invention. Complete reduction of alkenyl triazole acid XVII of the invention then provides the saturated alkyl triazole acid XVIII of the invention.

The synthesis of ether-containing analogs XIX and XX are shown in Schemes 15–16.

In Scheme 15, treatment of a suitably protected halo-aryl triazole 72 with a metallating agent (e.g. isopropyl magnesium bromide, reference: P. Knochel et al., *Synthesis*, 2002, 565–569) furnishes the corresponding arylmagnesium reagent, which is then reacted with formaldehyde to provide benzyl alcohol 75. Treatment of alcohol 75 with mesylate VIII in the presence of base provides the corresponding ether-anilide, which is then deprotected to furnish the ether-acid XIX of the invention.

In Scheme 16, treatment of a suitably protected halo-aryl triazole 72 with an appropriate vinyl tin reagent (e.g. tributylvinyltin) under Stille coupling conditions (reference: Farina, V., Krishnamurthy, V., and Scott, W. J., *Organic*

Reactions, 1997, 50, 1) provides the corresponding vinyl intermediate, which can then undergo hydroboration (e.g. borane-THF) to give the alcohol 76. Treatment of alcohol 76 with mesylate VIII in the presence of base provides the corresponding ether anilide, which is then deprotected to provide the ether acid XX of the invention.

A synthesis of 2-substituted triazole-4-acids XXI is shown in Scheme 17. Treatment of acetylenic ester 26 with sodium azide results in a dipolar cycloaddition which provides the triazole-ester 77. Coupling of the triazole-ester 77 with an appropriately substituted aryl or heteroaryl boronic acid 54 using standard literature conditions (Lam, P. Y. S., et. al., *Tetrahedron Lett.*, 1998, 39, 2941) furnishes preferentially the N(2)-substituted triazole ester 78. Deprotection of the triazole-ester 78 then provides the N(2)-substituted triazole acid XXI of the invention.

The syntheses of the homologated ether-containing analogs XXII–XXIV are shown in Schemes 18–19.

In Scheme 18, treatment of a suitably protected halo-aryl triazole 72 with a suitably protected acetylenic alcohol 79 (where $x^3$=1–3 is preferred) under standard Sonogashira coupling conditions (e.g.

"Organocopper Reagents, a Practical Approach", R. J. K. Taylor, E., Chapter, 10, p 217–236, Campbell, I. B., Oxford University Press, 1994) furnishes the corresponding alkynyl triazole 80. Hydrogenation of 80 followed by deprotection of the alcohol provides the triazole-alcohol 81. Treatment of alcohol 81 with mesylate VIII in the presence of base provides the corresponding ether-anilide, which is then deprotected to furnish the ether-acid XXII of the invention.

In Scheme 19, deprotection of triazole 80 furnishes the acetylenic alcohol 81, which undergoes reaction with mesylate VIII in the presence of base to provide the corresponding ether anilide, which is then deprotected to provide the ether acid XXIII of the invention. Selective reduction of the alkynyl triazole acid XXIII (e.g. $H_2$/Lindlar catalyst) provides the E- or Z-alkenyl triazole acid XXIV of the invention.

These general synthetic schemes for the preparation of triazole-acid analogs are also applicable to pyrrole-acid analogs, as shown in Schemes 20–21. The synthetic scheme for the preparation of pyrrole acid analogs XXV–XXIX follows the approach described in Scheme 10. The haloaldehyde 83 is reacted under basic conditions (most preferably with fluoride anion in the presence of 18-crown-6) with a trimethylsilylpropiolate ester 84 to provide the alkyne-alcohol 85. Deoxygenation of the alcohol functionality of alkyne 50 using standard methods (e.g. $Et_3SiH$/acid; Tetrahedron Lett., 1987, 28, 4921) provides the alkynoate ester 86. Reduction of the alkynoate ester 86 using standard methods ("Preparation of Alkenes, A Practical Approach", J. M. J. Williams, Ed., Chapter 6, "Reduction of Alkynes", J. Howarth. Oxford University Press, 1996) furnishes the Z-alkenyl ester 87. The α,β-unsaturated ester 87 is then reacted with tosylmethyl isocyanate (TosMIC) under standard literature conditions (Van Leusen, A. M., et al, *Tetrahedron Lett.*, 1972, 5337) to give the corresponding pyrroleester 88. Coupling of the pyrrole-ester 88 with an appropriately substituted aryl or heteroaryl boronic acid 54 using standard literature conditions (Lam, P. Y. S., et al, *Tetrahedron Lett.*, 1998, 39, 2941) furnishes the key intermediate, halo-aryl N-substituted pyrrole ester 89, which is the pyrrole equivalent of the halo-aryl triazole intermeidate 72. Subjection of the haloaryl pyrrole 89 to the same reaction sequences as described in Schemes 15, 16, 18 and 19 for triazole 72 provides the pyrrole acids XXV–XXIX of the invention as shown in Scheme 21.

The synthesis of homologated triazole acids XXX is shown in Scheme 22 and follows a modified Arndt-Eistert protocol (ref. E. Gordon et al., *J. Med. Chem.*, 1988, 31, 2199). Treatment of triazole-acid IIA with oxalyl chloride provides the corresponding acid chloride, which is immediately reacted with diazomethane to provide the corresponding α-diazoketone 90. Treatment of diazoketone 90 with a silver salt (e.g. silver benzoate) in the presence of methanol affords the corresponding homologated triazole ester. Hydrolysis of the triazole-ester furnishes the desired homologated triazole-acids XXX.

The synthesis of homologated pyrrole-acids XXXI is shown in Schemes 23–24. Coupling of protected aryl halide 91 with the silyl-alkyne 92 under standard Sonogashira conditions (ref. Organocopper Reagents, a Practical Approach, R. J. K. Taylor, Ed., Chapter 10, pp 217–236, Campbell, I. B., Oxford University Press, 1994) provides the arylalkyne 93. Removal of the silyl group (e.g. fluoride) followed by treatment with base and an appropriate chloroformate 94 (e.g. methyl chloroformate) furnishes the alkynoate ester 95. 1,3-Dipolar cycloaddition of acetylenic ester 95 with N-trimethylsilylmethyl N-methoxymethyl benzylamine 96 under standard literature conditions (e.g. J. S. Carey, *J. Org. Chem.*, 2001, 66, 2526–2529) furnishes the N-benzyl dihydropyrrole 97. Selective deprotection of the N-benzyl group under standard literature conditions (R. A. Olofson et al, *J. Org. Chem.*, 1984, 49, 2081) provides the dihydropyrrole 98, which is then reprotected (e.g. $PG_3$ as the t-butyloxy carbamate or as the benzyloxy carbamate) as intermediate 99. Reduction of dihydropyrrole ester 99 by standard literature methods (e.g. diisobutylaluminum hydride) furnishes the corresponding allylic alcohol, which then undergoes halogenation by standard literature methods (e.g. $Ph_3P/CBr_4$ or $PBr_3$ to furnish the bromide; $Ph_3P/CCl_4$ to furnish the chloride) furnishes the corresponding allylic halide 100. Carbonylation (ref. Kiji, J. et al, *Bull. Chem. Soc. Jpn.*, 1996, 69, 1029–1031) with carbon monoxide in the presence of a palladium catalyst and methanol) of 100 provides the dihydropyrrole ester 101, which is deprotected to afford amine 102. Reaction of 102 with boronic acids 54 in the presence of a copper (I) salt and base with heating furnishes the pyrrole-ester 103. Deprotection of the phenol of 103 is carried out by treatment with boron tribromide followed by alkylation with mesylate 4 under basic conditions provides the pyrrole ester 104. Deprotection of pyrrole-ester 104 by hydrolysis then furnishes the homologated pyrrole-acids XXXI of the invention.

An alternative synthesis of triazole acids IIA is shown in Scheme 25. Treatment of β-ketoester 38 with a diazonium salt 105 provides the diazo-β-ketoester 106 (ref: V. S. Jolly et al, *J. Indian Chem. Soc.*, 1991, 68, 513–514). Reaction of diazo-β-ketoester 106 with a copper (II) salt such as copper (II) acetate under elevated temperatures (ref: F. Zumstein et al, German patent DT2133012, 1970) furnishes the triazole ester 107. A 3-step sequence comprising: 1) deprotection of the phenol moiety of triazole ester 107 for example by treating with boron tribromide; 2) alkylation of the phenol with mesylate 4 under basic conditions and 3) deprotection of the acid for example by hydrolysis, then provides the desired triazole-acids IIA.

SCHEME 1
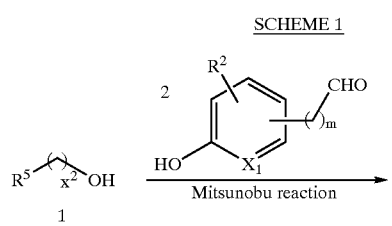
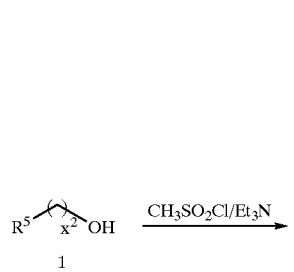
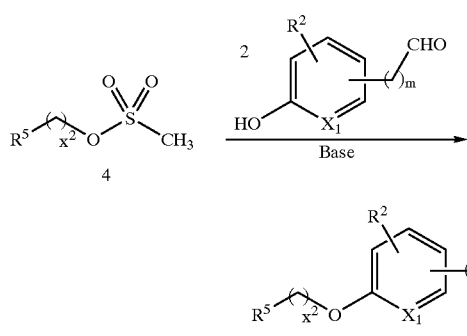
In this and the following Reaction Schemes,
$R^5$ =
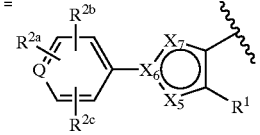
SCHEME 2
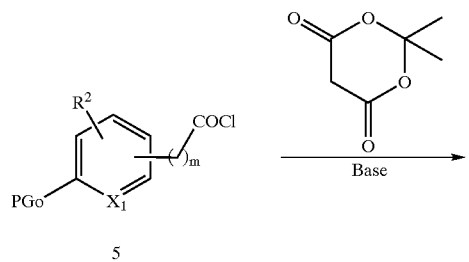
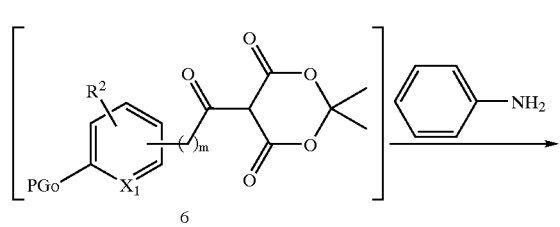
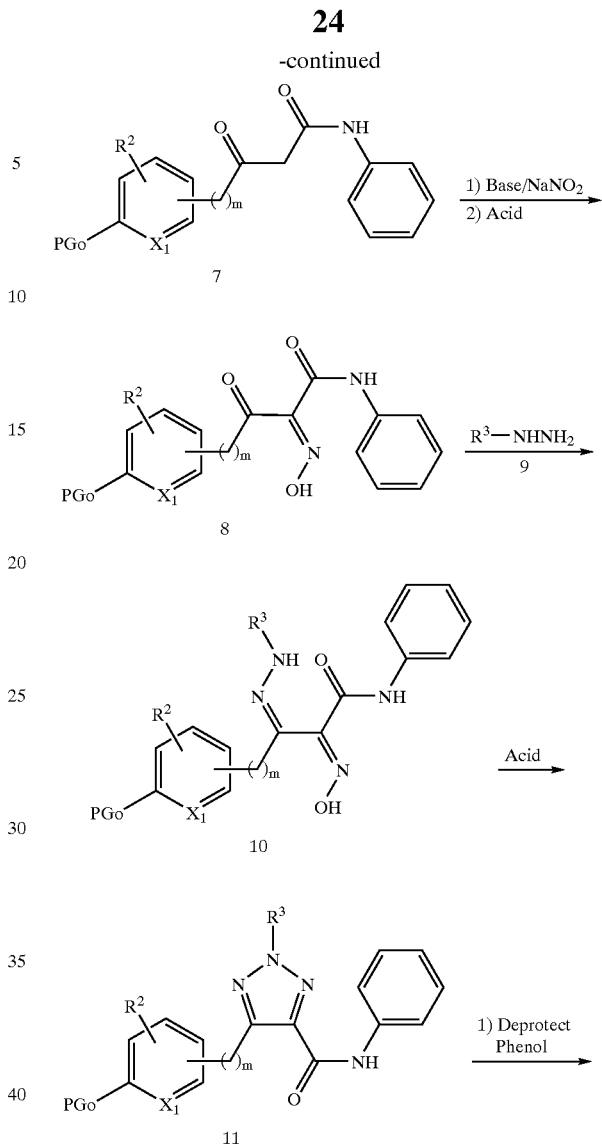
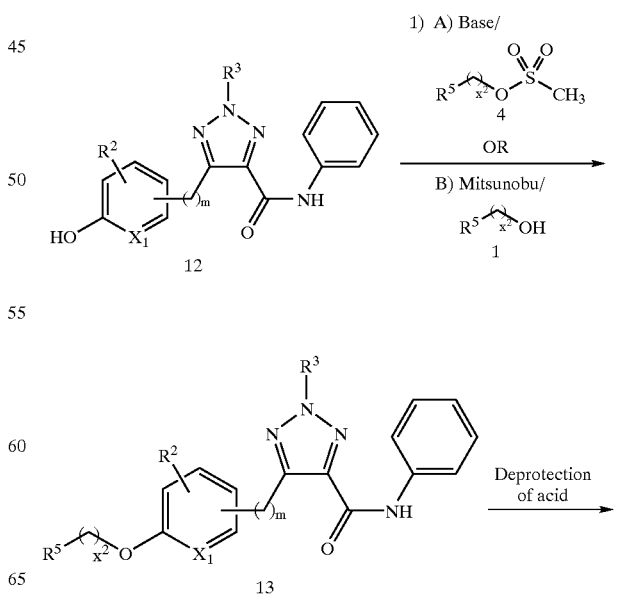

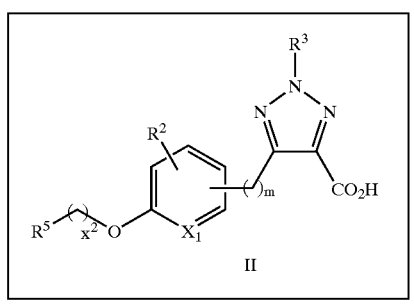
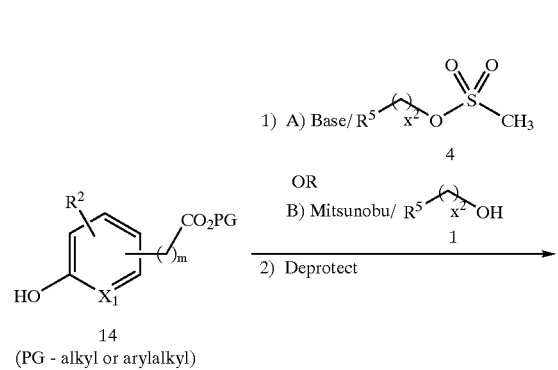
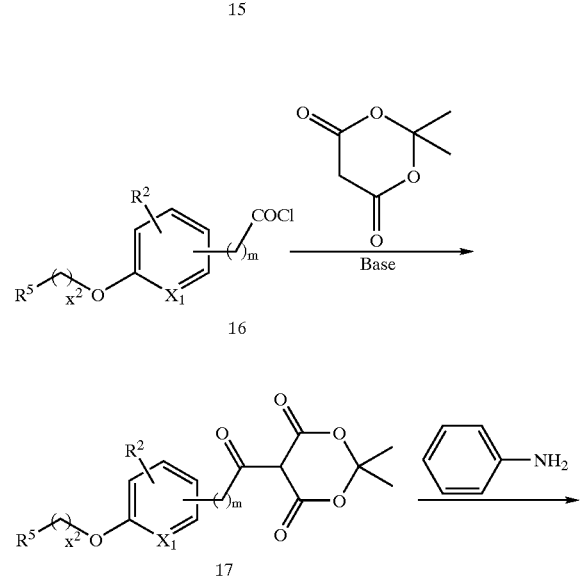
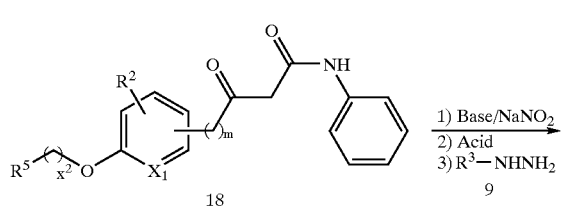
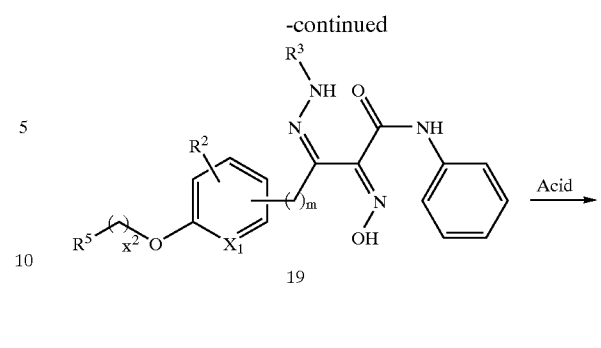
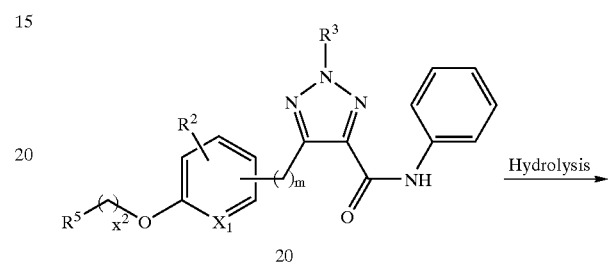
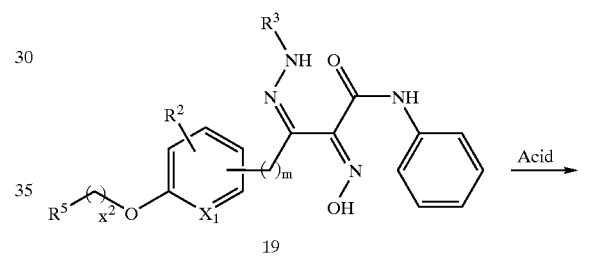
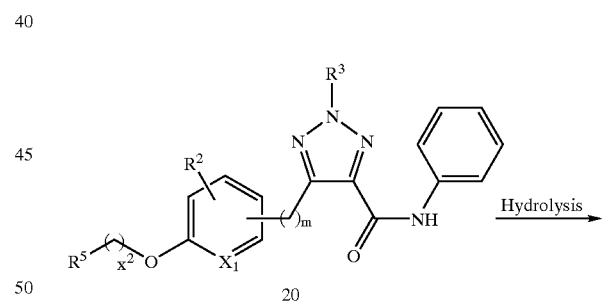
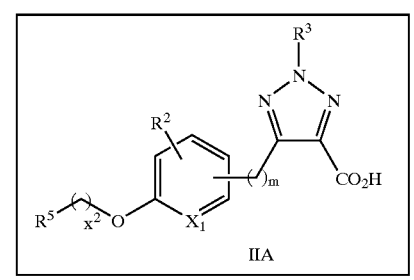

SCHEME 4
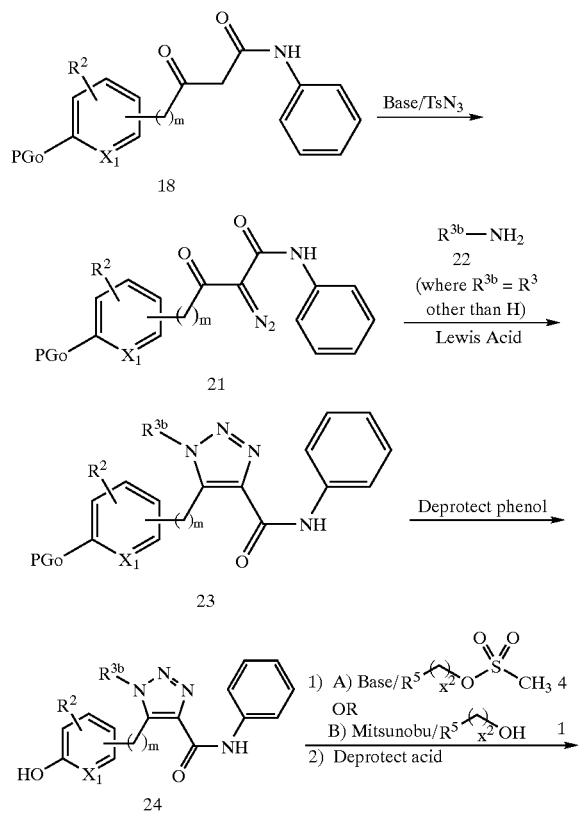
SCHEME 5
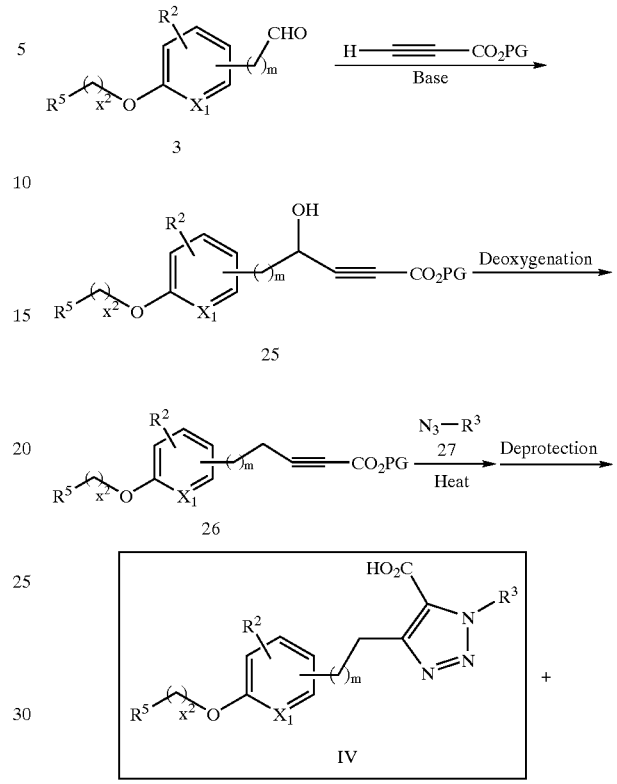
SCHEME 6
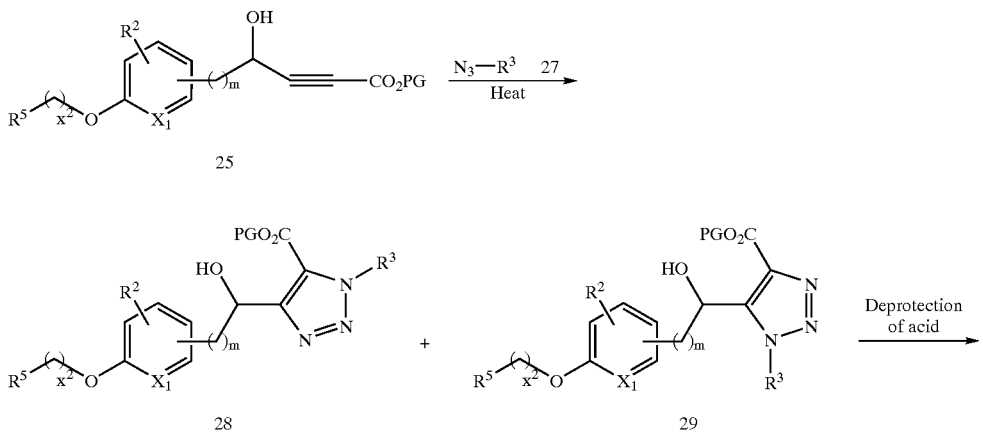

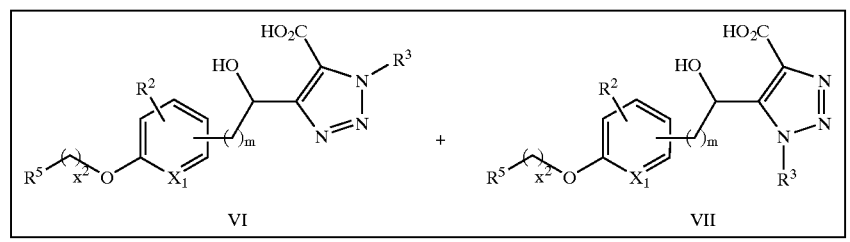
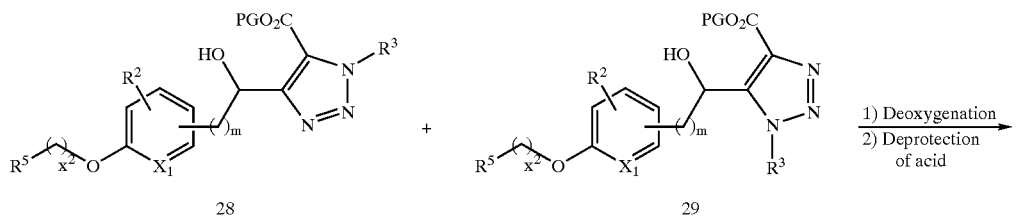
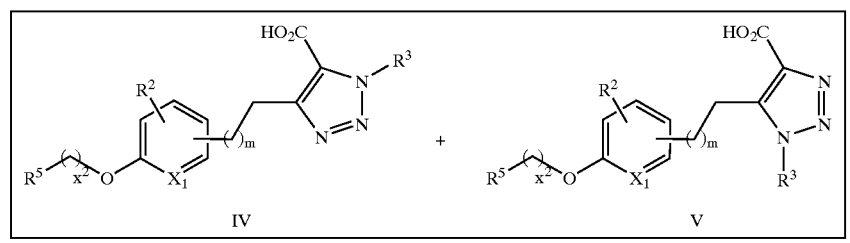
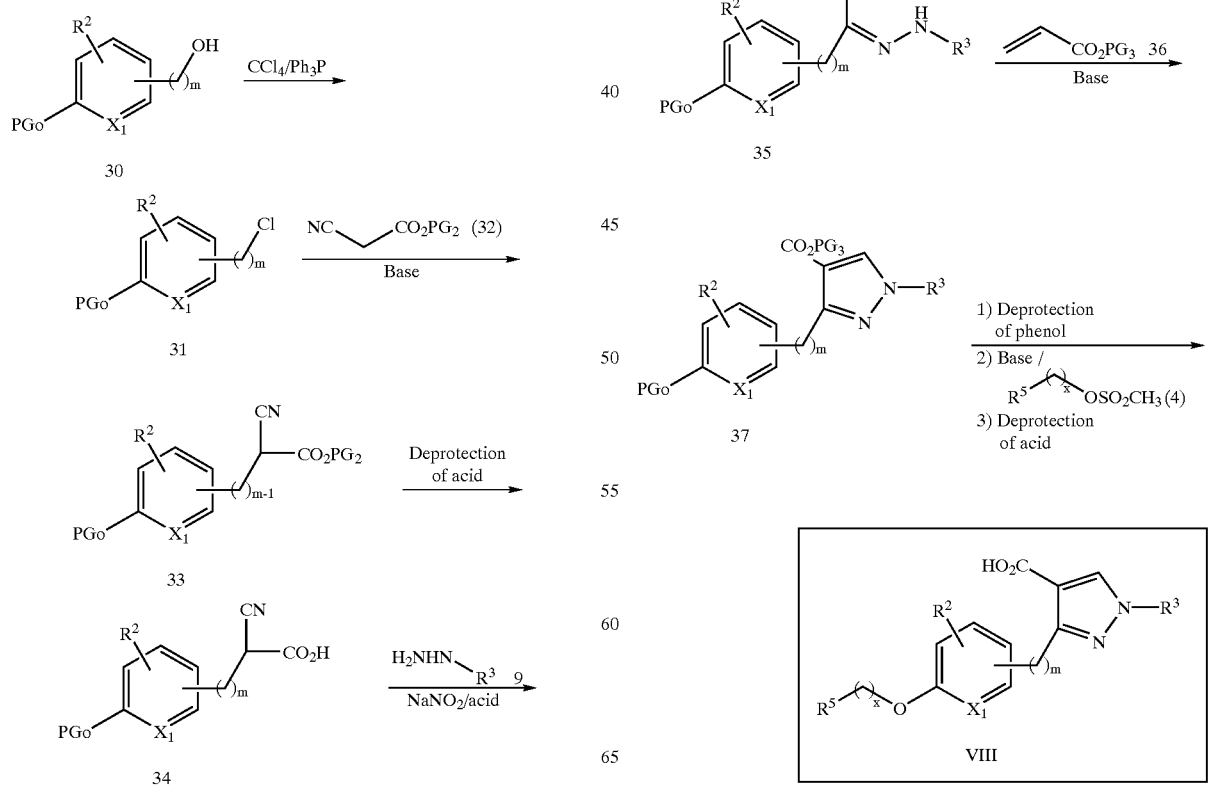

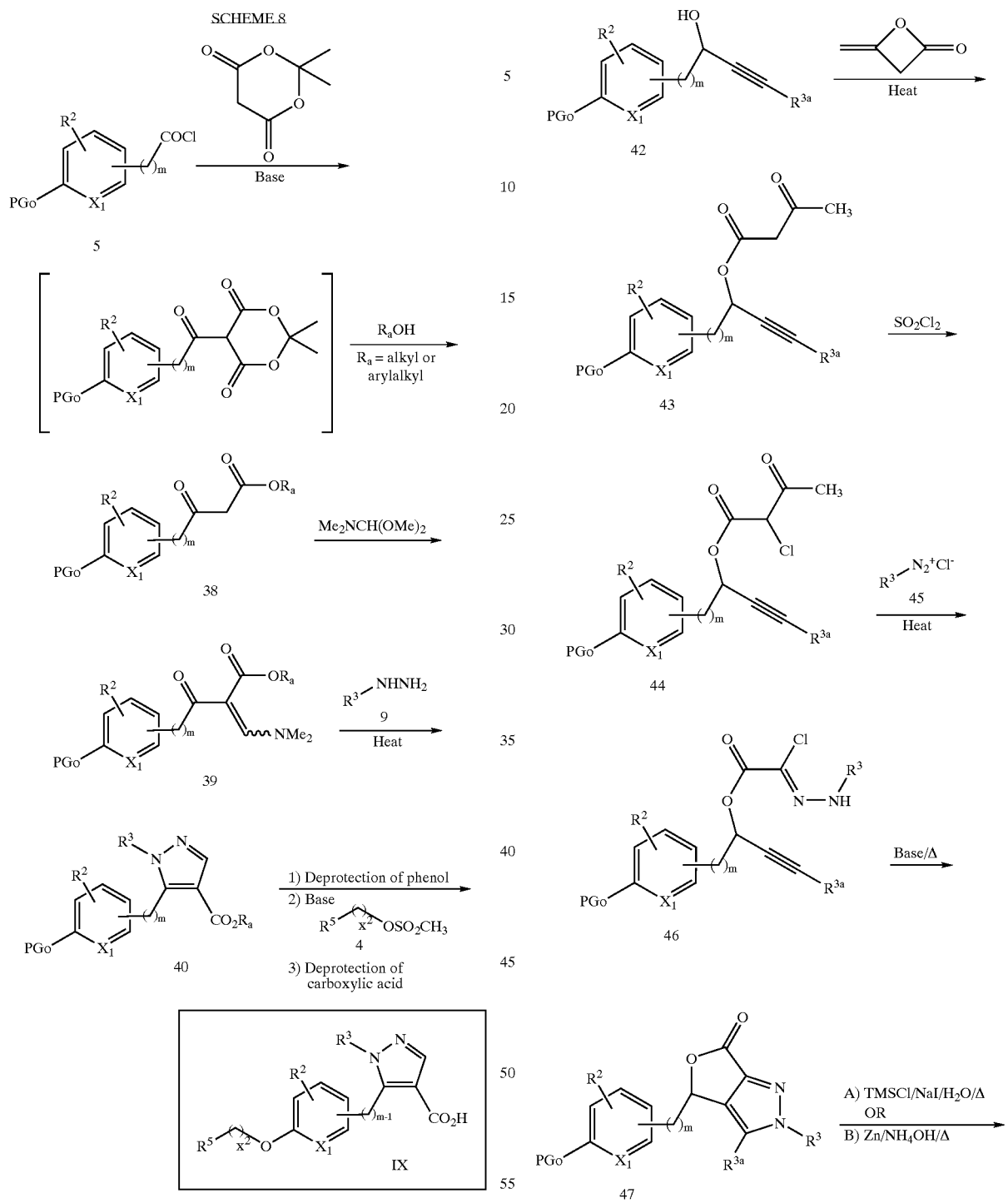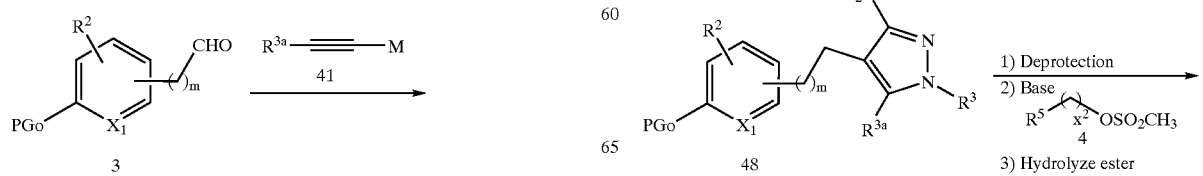

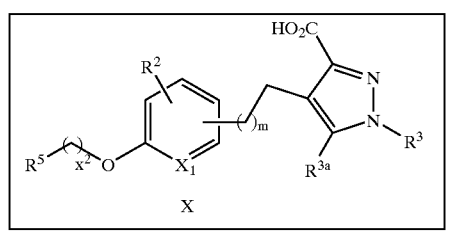
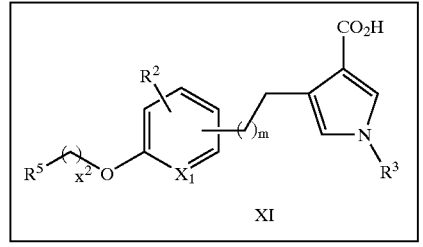
SCHEME 10
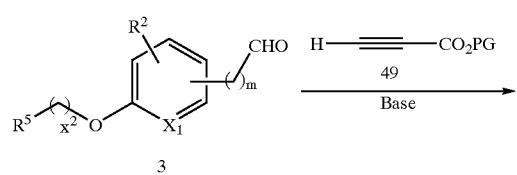
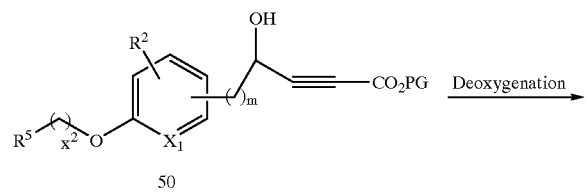
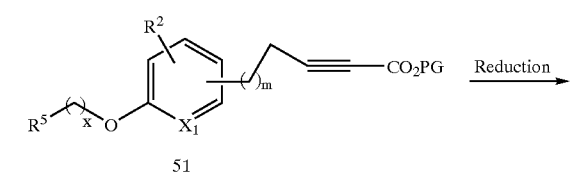
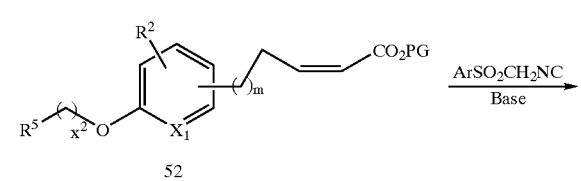
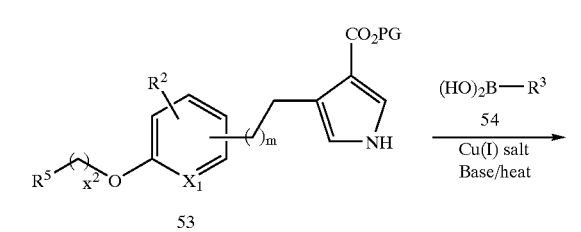
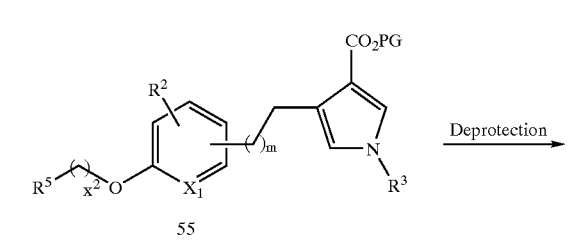
SCHEME 11
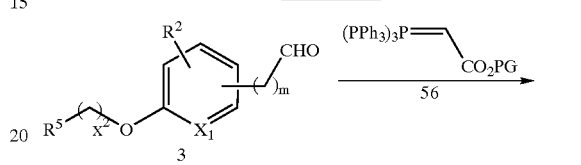

SCHEME 12
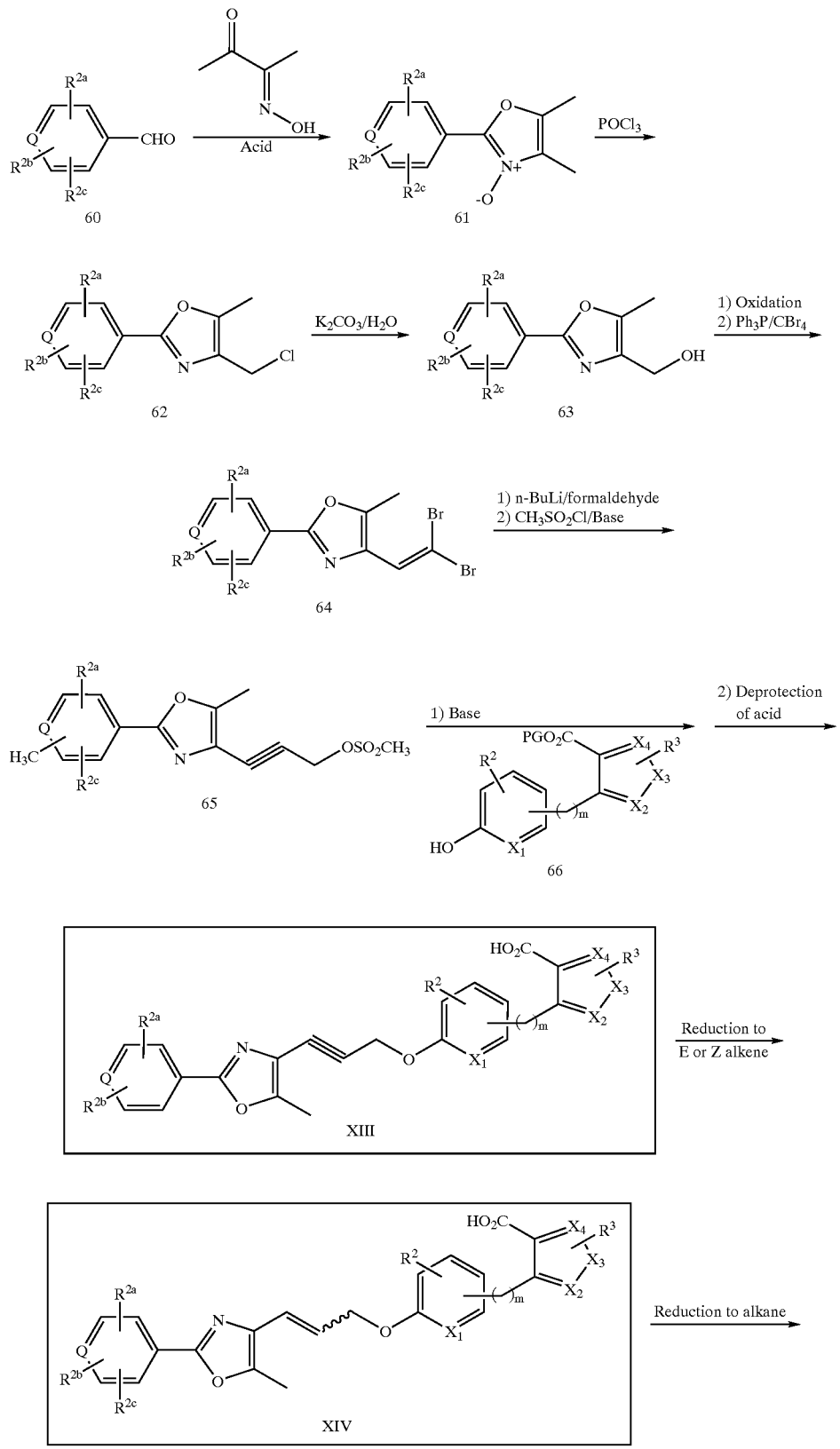

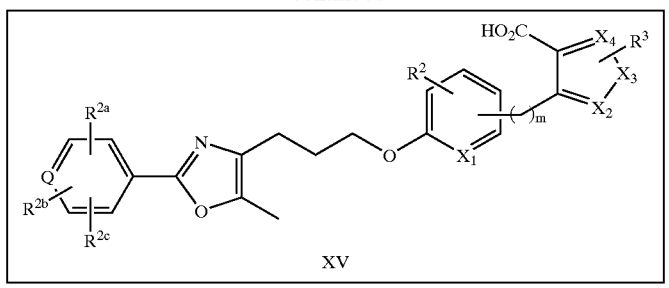
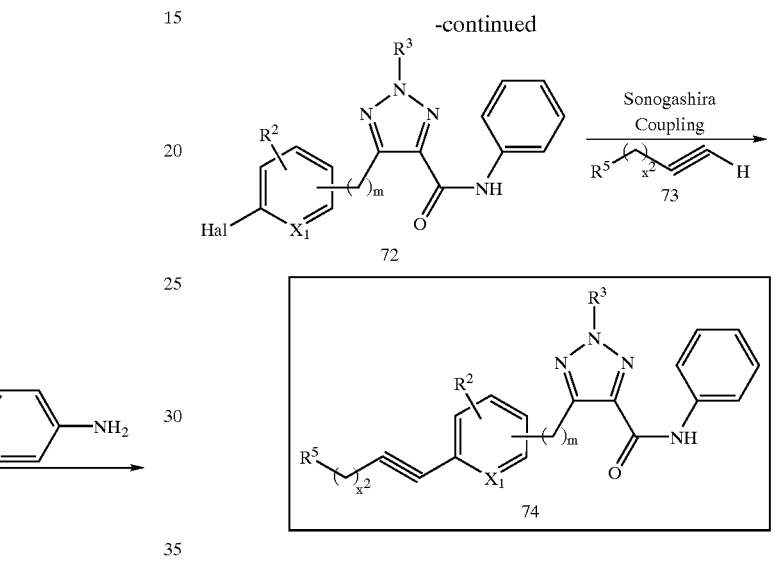
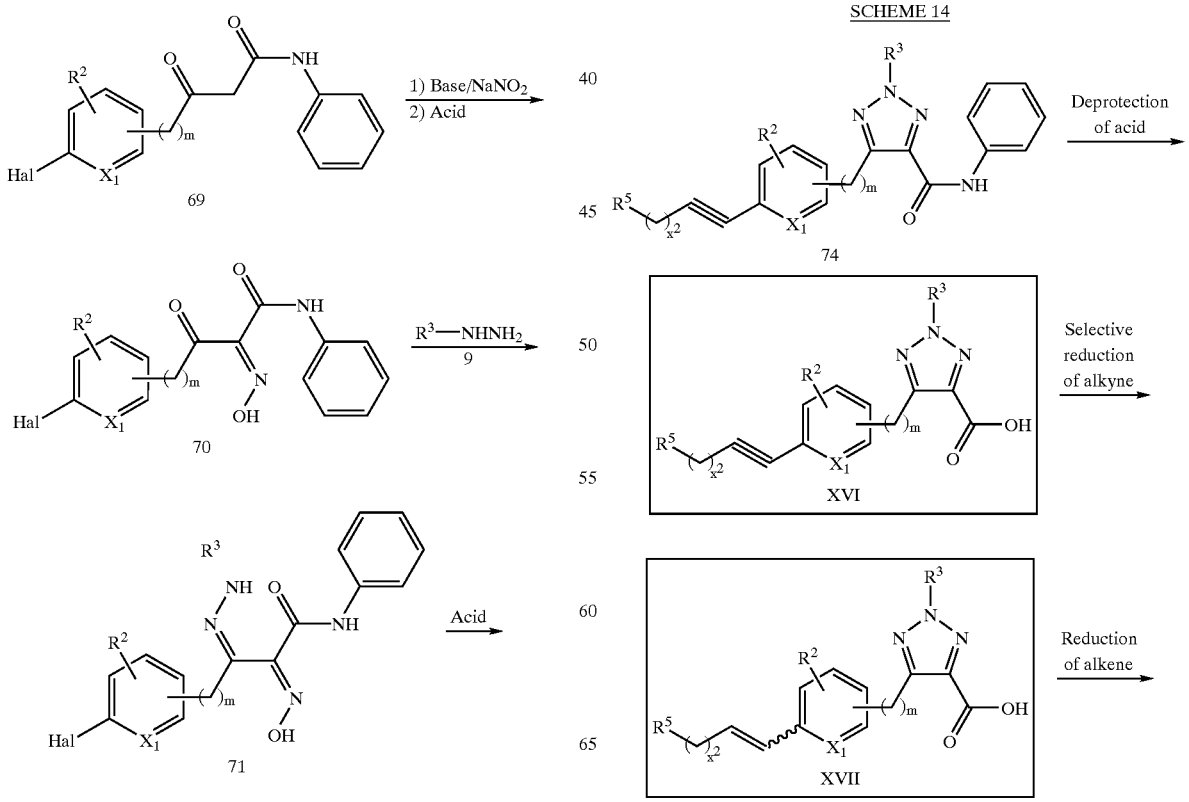

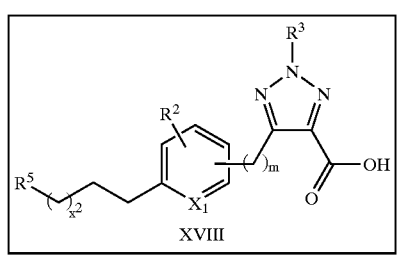
XVIII
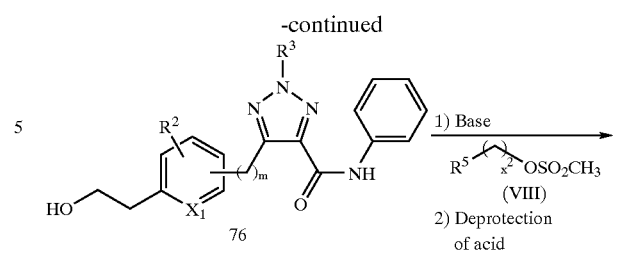
76
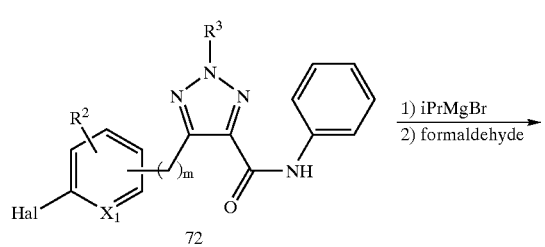
SCHEME 15
72
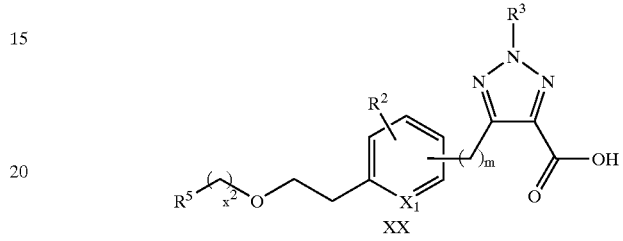
XX
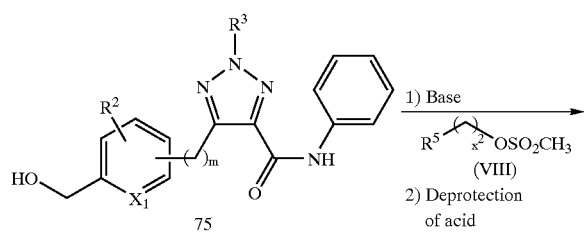
75
SCHEME 17
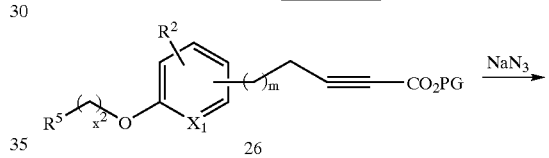
26
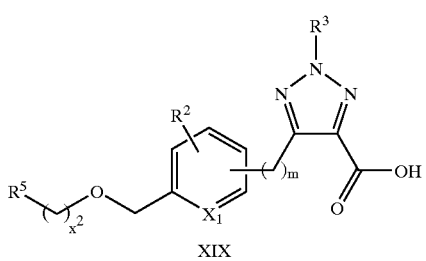
XIX
SCHEME 16
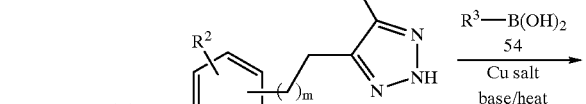
77
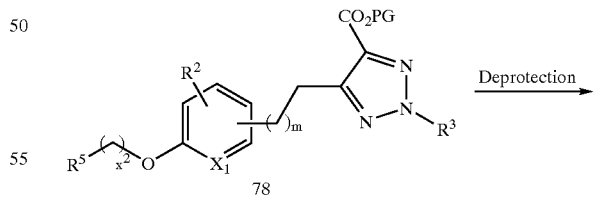
78
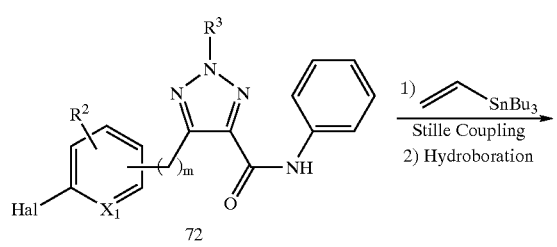
72
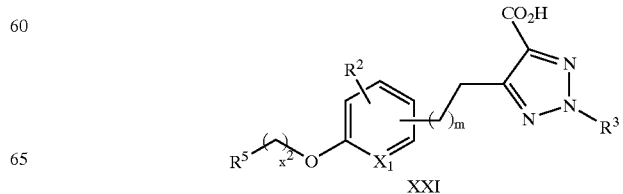
XXI SCHEME 18
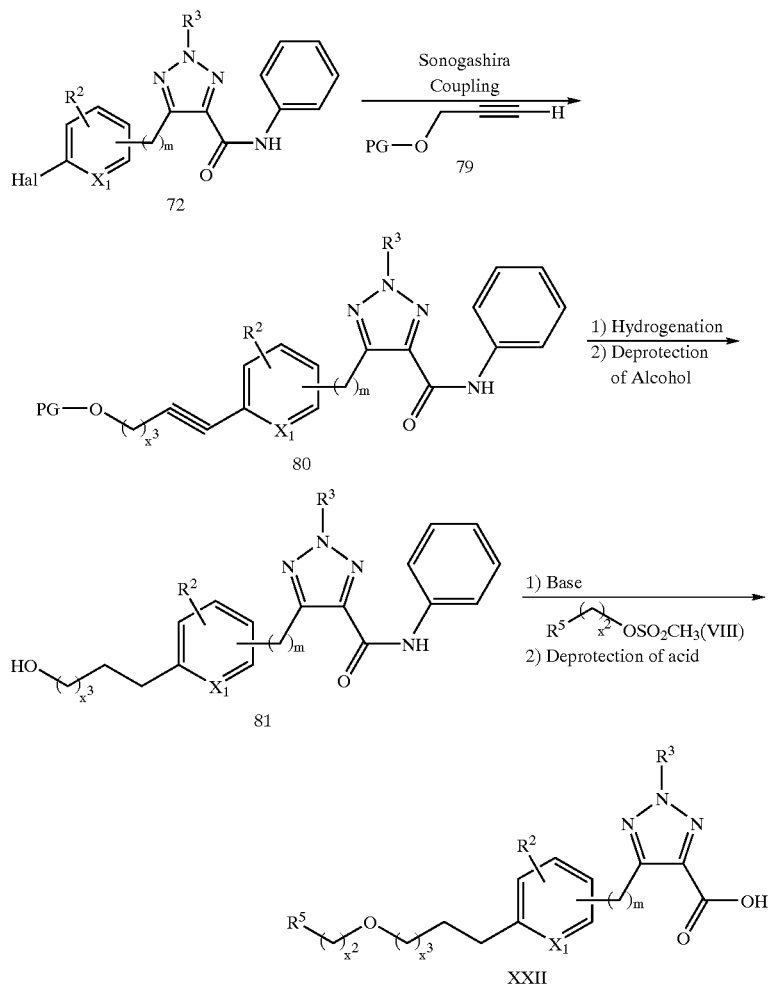
SCHEME 19
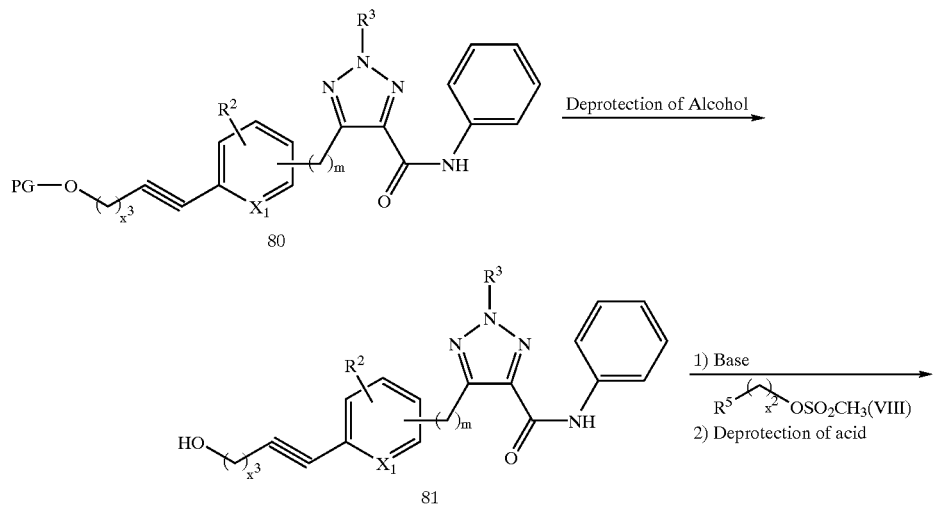

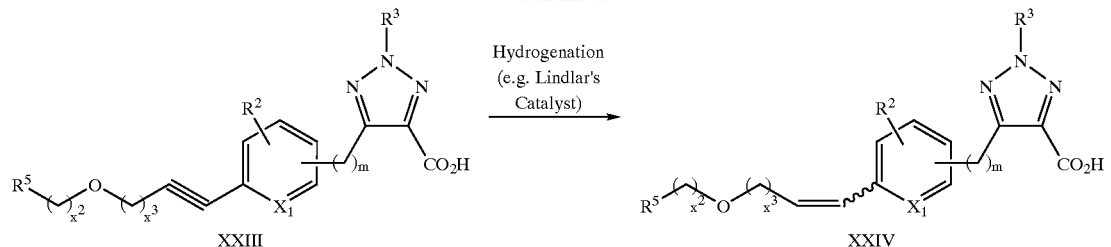
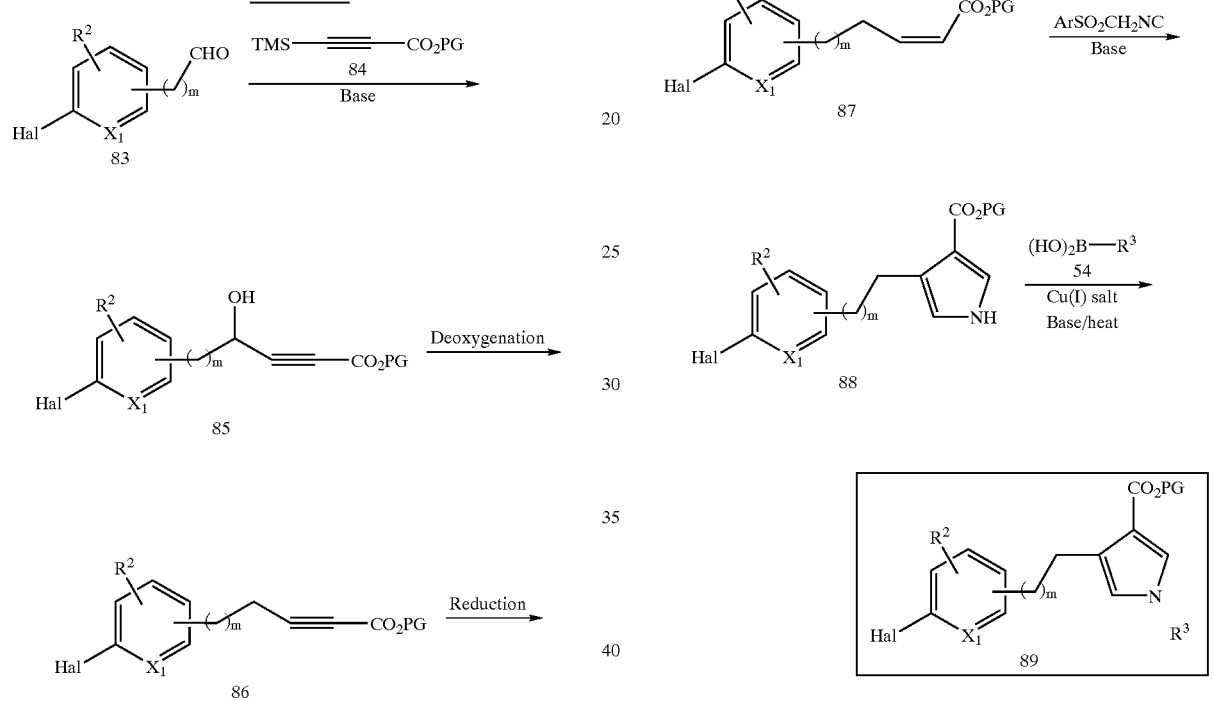
SCHEME 20
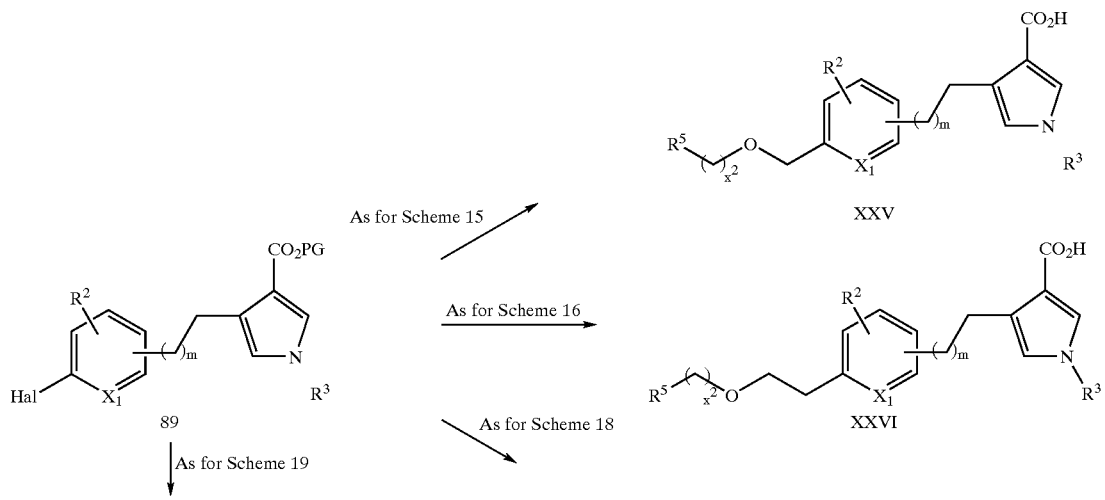
SCHEME 21

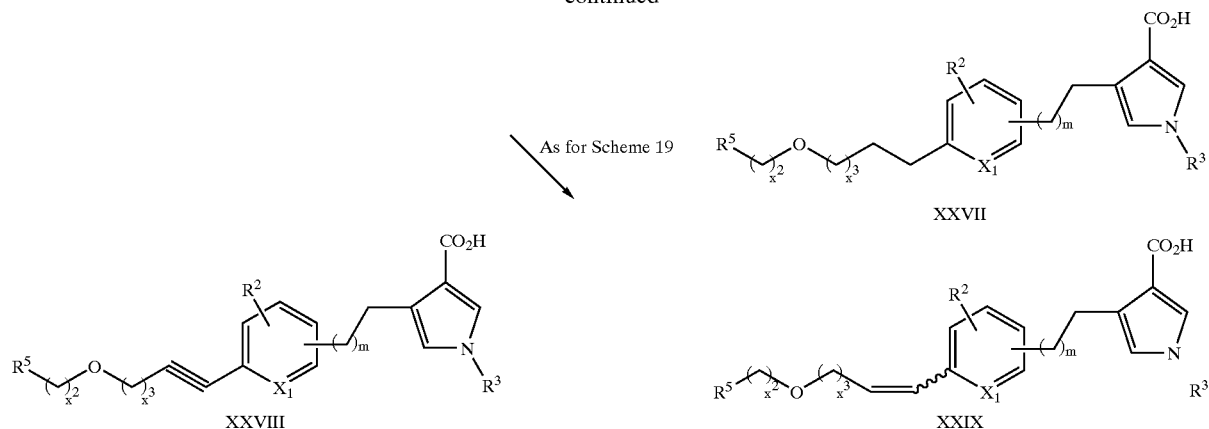
SCHEME 22
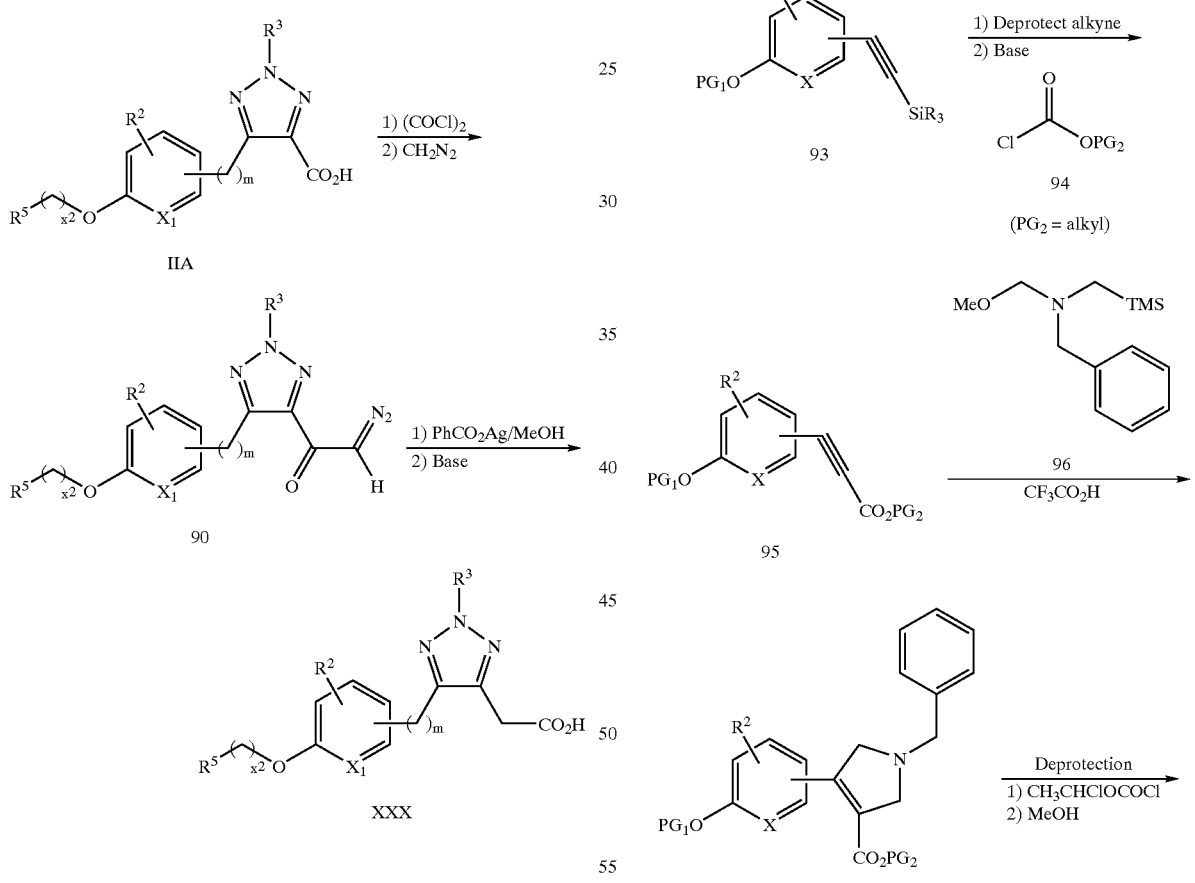
SCHEME 23
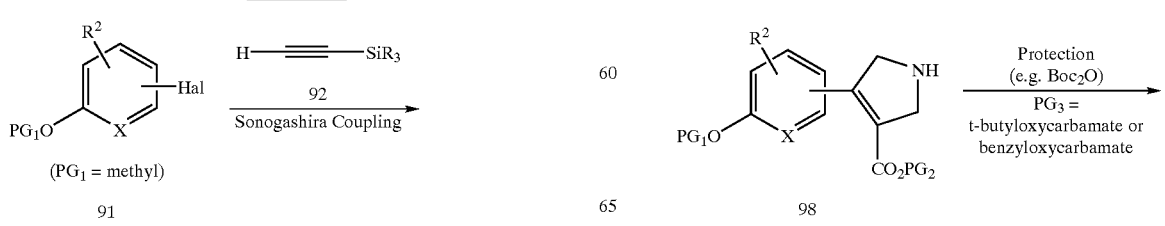

-continued
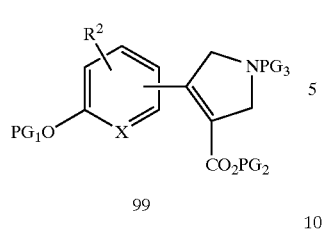
99
SCHEME 24
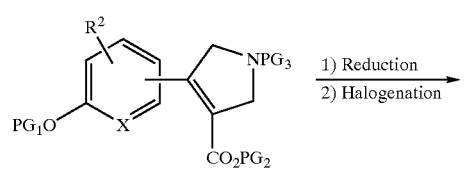
99
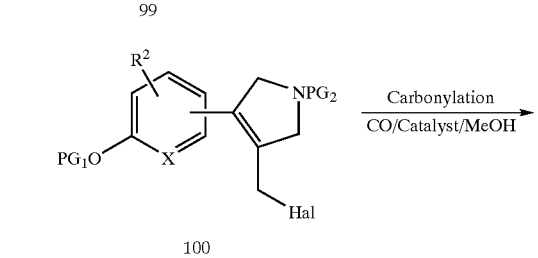
100
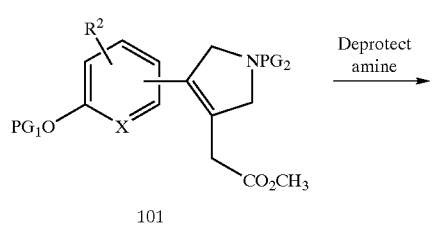
101
-continued
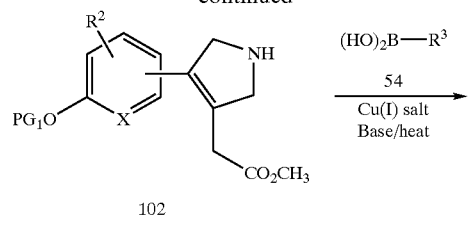
102
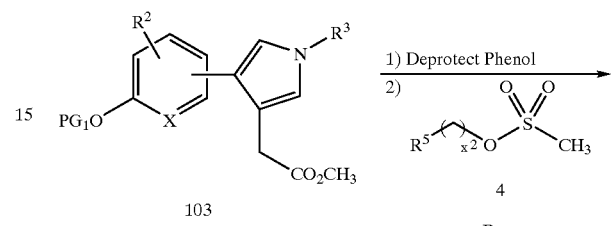
103
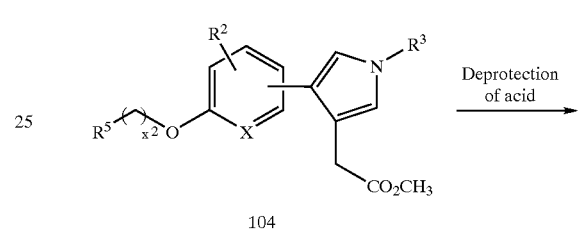
104
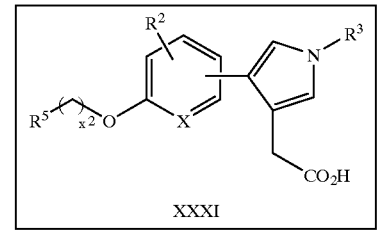
XXXI
SCHEME 25
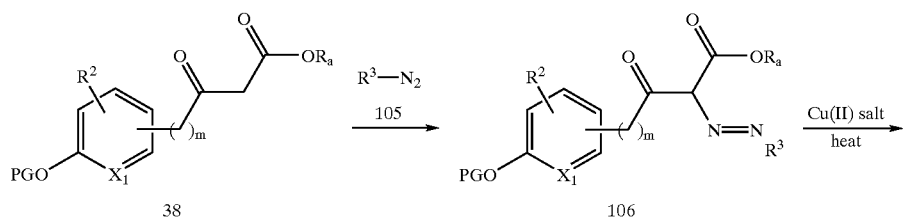
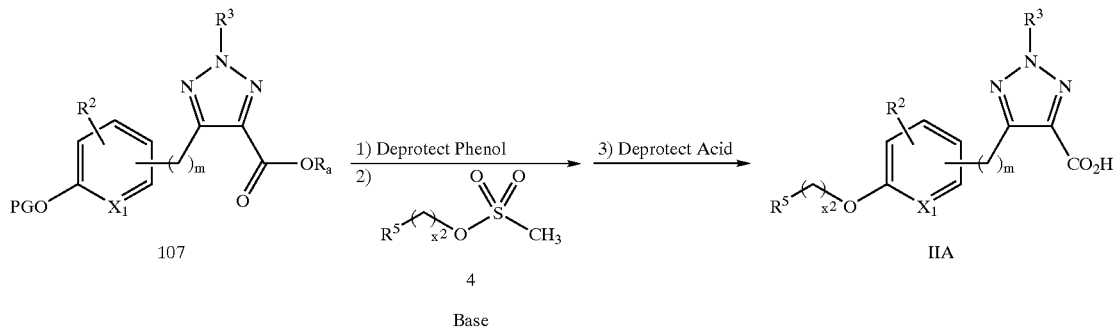

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, and may optionally include an oxygen or nitrogen in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio and/or any of the $R^3$ groups.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

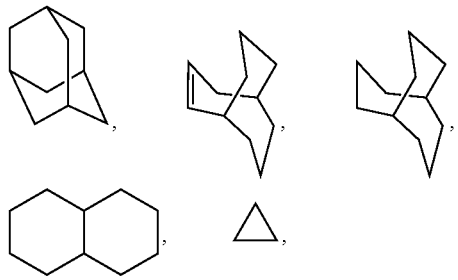

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

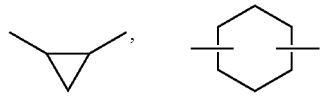

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, and may optionally include an oxygen or nitrogen in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the substituents for alkyl set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, and may optionally include an oxygen or nitrogen in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the substituents for alkyl set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

$(CH_2)_x$, $(CH_2)_x^1$, $(CH_2)_x^2$, $(CH_2)_x^3$, $(CH_2)_m$, or $(CH_2)_n$ includes alkylene, allenyl, alkenylene or alkynylene groups, as defined herein, each of which may optionally include an oxygen or nitrogen in the normal chain, which may optionally include 1, 2, or 3 substituents which include alkyl, alkenyl, halogen, cyano, hydroxy, alkoxy, amino, thioalkyl, keto, $C_3$-$C_6$ cycloalkyl, alkylcarbonylamino or alkylcarbonyloxy; the alkyl substituent may be an alkylene moiety of 1 to 4 carbons which may be attached to one or two carbons in the $(CH_2)_x$, $(CH_2)_x^1$, $(CH_2)_x^2$, $(CH_2)_x^3$ or $(CH_2)_m$ or $(CH_2)_n$ group to form a cycloalkyl group therewith.

Examples of $(CH_2)_x$, $(CH_2)_x^1$, $(CH_2)_x^2$, $(CH_2)_x^3$, $(CH_2)_m$, $(CH_2)_n$, alkylene, alkenylene and alkynylene include

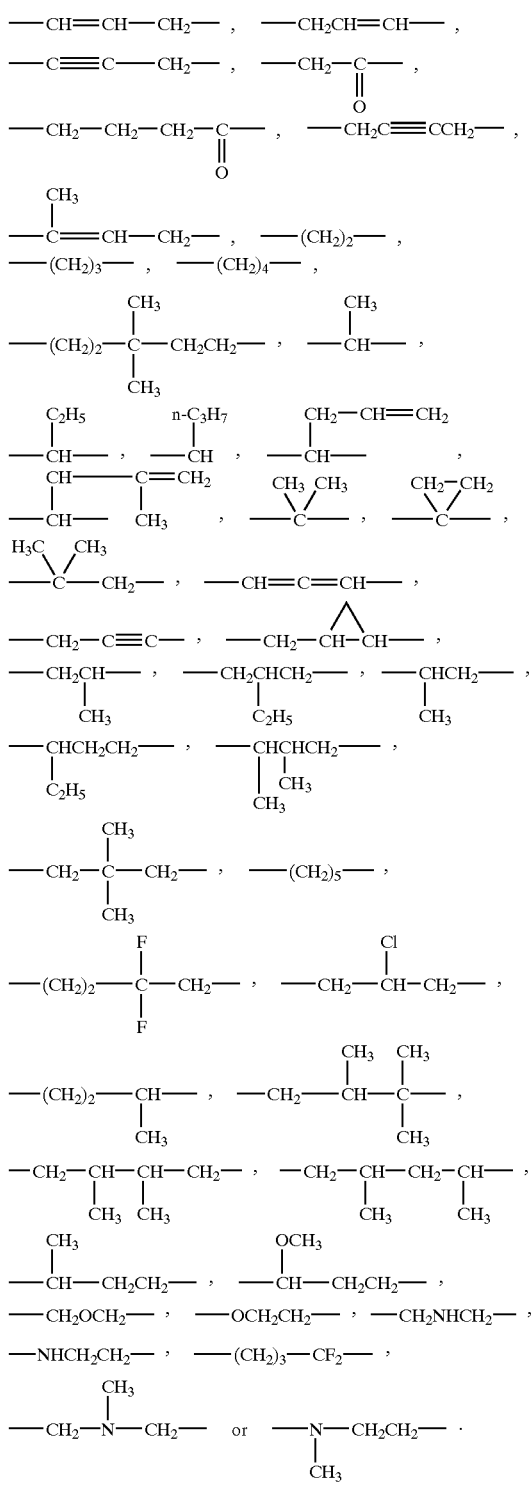

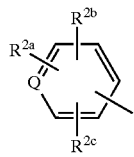

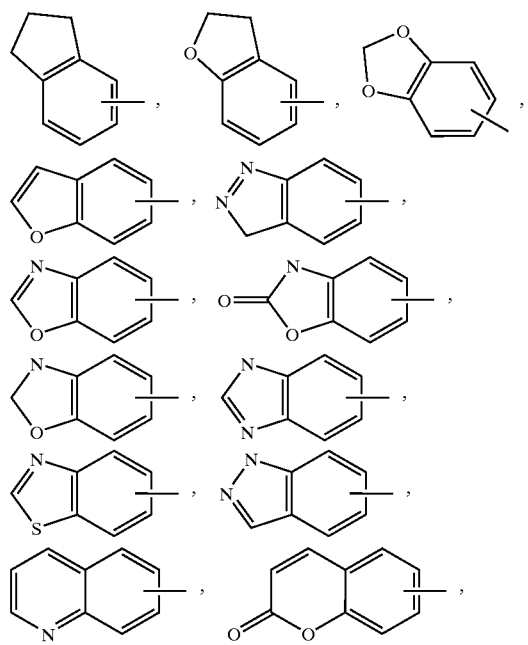

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or the group where Q is C, as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the substituents for alkyl set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

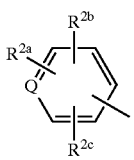

group; examples of acyl groups include any of the $R^3$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 1, 2 or 3), such as

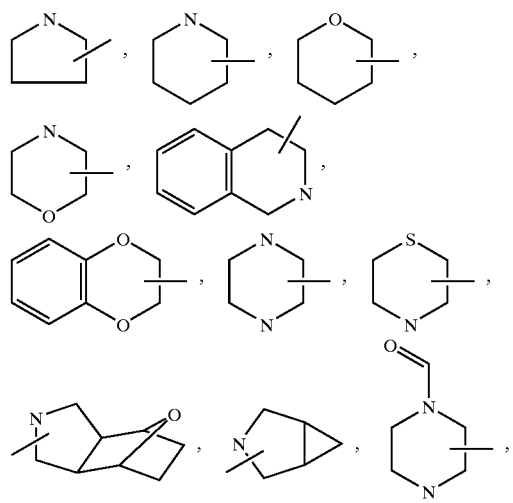

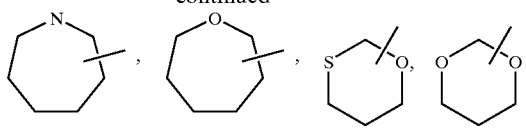

and the like. The above groups may include 1 to 4 substituents such as alkyl, halo, oxo and/or any of of the substituents for alkyl or aryl set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring including

where Q is N, which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the the substituents for alkyl or aryl set out above. Examples of heteroaryl groups include the following:

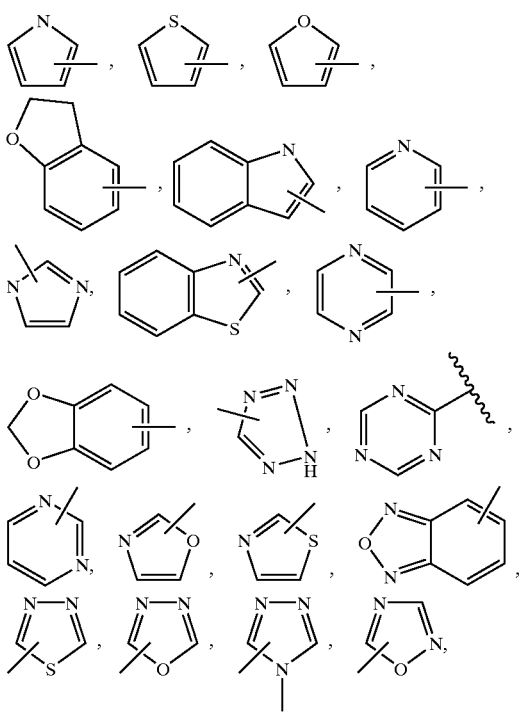

and the like.

Examples of

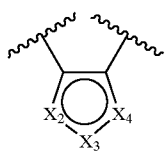

groups include, but are not limited to:

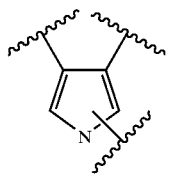
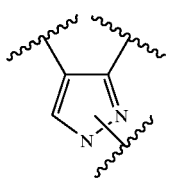
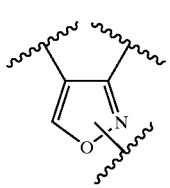
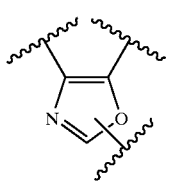
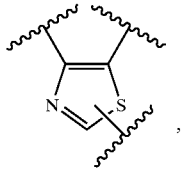
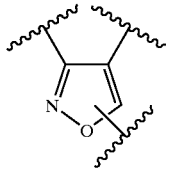
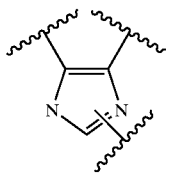

Examples of

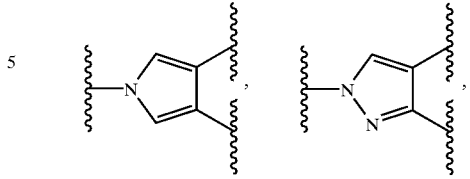

groups include, but are not limited to,

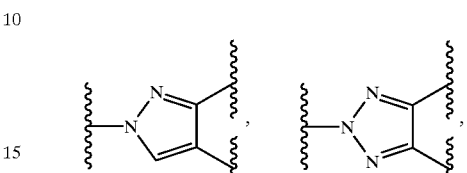
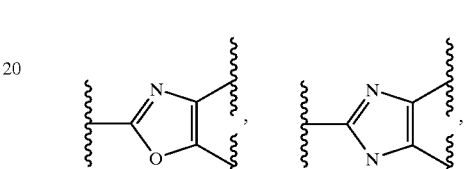
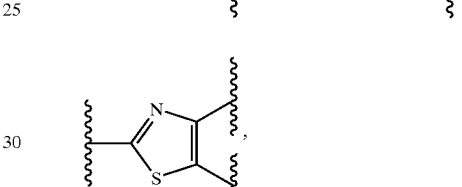

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a —$(CH_2)_p$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes prodrug esters which are known in the art for carboxylic and phosphorus acid esters such as methyl, ethyl, benzyl and the like. Other prodrug ester examples of $R^4$ include the following groups: (1-alkanoyloxy)alkyl such as,

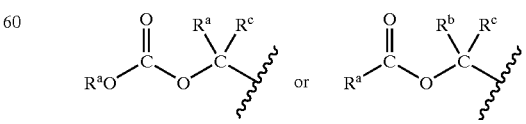

wherein $R^a$, $R^b$ and $R^c$ are H, alkyl, aryl or arylalkyl; however, $R^a O$ cannot be HO.

Examples of such prodrug esters $R^4$ include

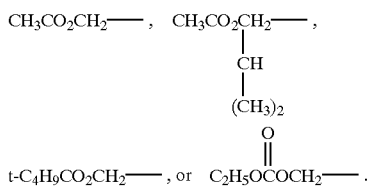

Other examples of suitable prodrug esters $R^4$ include

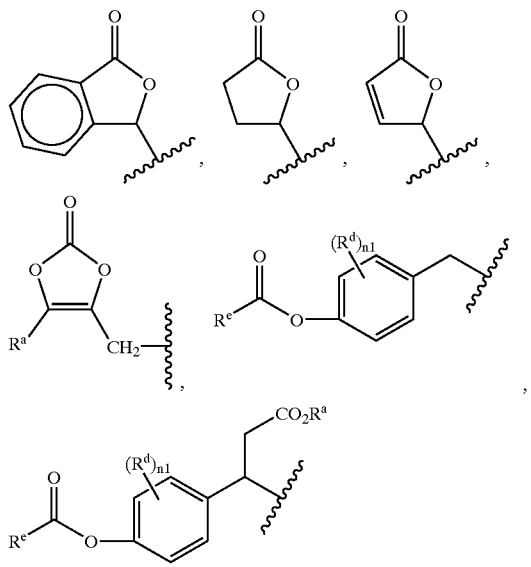

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

Where the compounds of structure I are in acid form they may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, lysine (D or L), ethylenediamine, t-butylamine, t-octylamine, tris-(hydroxymethyl) aminomethane (TRIS), N-methyl glucosamine (NMG), triethanolamine and dehydroabietylamine.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Where desired, the compounds of structure I may be used in combination with one or more hypolipidemic agents or lipid-lowering agents or lipid modulating agents and/or one or more other types of therapeutic agents including antidiabetic agents, anti-obesity agents, antihypertensive agents, platelet aggregation inhibitors, and/or anti-osteoporosis agents, which may be administered orally in the same dosage form, in a separate oral dosage form or by injection.

The hypolipidemic agent or lipid-lowering agent or lipid modulating agents which may be optionally employed in combination with the compounds of formula I of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and 5,760,246.

The most preferred MTP inhibitor is 9-[4-[4-[[2-(2,2,2-Trifluoroethoxy)benzoyl]amino]-1-piperidinyl] butyl]-N-(2, 2,2-trifluoroethyl)-9H-fluorene-9-carboxamide

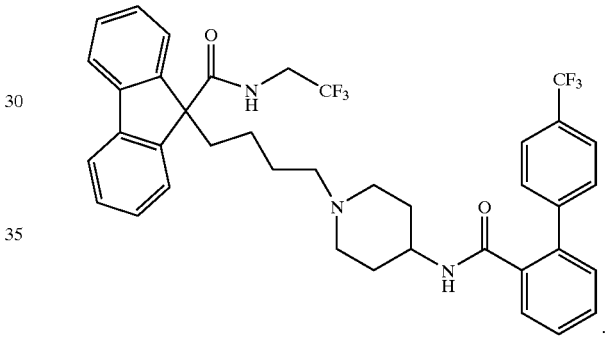

The hypolipidemic agent may be an HMG CoA reductase inhibitor which includes, but is not limited to, mevastatin and related compounds as disclosed in U.S. Pat. No. 3,983, 140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354, 772, cerivastatin disclosed in U.S. Pat. Nos. 5,006,530 and 5,177,080, atorvastatin disclosed in U.S. Pat. Nos. 4,681, 893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3- disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58–035, American Cyanamid CL-277,082 and CL-283,546 (disubstituted urea derivatives), nicotinic acid (niacin), acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's $SCH_{48461}$ as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

The lipid-modulating agent may be a cholesteryl ester transfer protein (CETP) inhibitor such as Pfizer's CP 529, 414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1,2,3 or more antidiabetic agents or antihyperglycemic agents including insulin secretagogues or insulin sensitizers, or other antidiabetic agents preferably having a mechanism of action different from the compounds of formula I of the invention, which may include biguamides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguamide such as metformin or phenformin or salts thereof, preferably metformin HCl.

Where the antidiabetic agent is a biguamide, the compounds of structure I will be employed in a weight ratio to biguamide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation- Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998).

The antidiabetic agent may be an SGLT2 inhibitor such as disclosed in U.S. application Ser. No. 09/679,027, filed Oct. 4, 2000, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000, employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597-11603, 1999, TSL-225 (tryptophyl-1,2,3,4-tetrahydro-isoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may optionally be employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), GB98/284425 (KaroBio), and U.S. Provisional Application No. 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79–022 and Curr. Ther. Res. 40:74 (1986); Ru 44570 (Hoechst) disclosed in Arzneimittelforschung 34:1254 (1985), cilazapril (Hoffman-LaRoche) disclosed in J. Cardiovasc. Pharmacol. 9:39 (1987); R 31–2201 (Hoffman-LaRoche) disclosed in FEBS Lett. 165:201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. clin. Pharmacol. 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3- phenylpropyl]amino]-1-oxopropyl]-1,2,3,4-tetrahydro-6,7-dimethoxy-3-isoquinolinecarboxylic acid HCl)disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, 5,552,397, 5,504,080, 5,612,359, 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, BMS 189,921 ([S-(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®). Dosages employed will be as set out in the Physician's Desk Reference.

In carrying out our the method of the invention, a pharmaceutical composition will be employed containing the compounds of structure I, with or without another therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 50 and 2,000 mg per day, which can be administered in a single dose or in the form of individual doses from 1–4 times per day.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The following Examples represent preferred embodiments of the invention.

The following abbreviations are employed in the Examples:

Ph=phenyl
Bn=benzyl
t-Bu=tertiary butyl
Me=methyl
Et=ethyl
TMS=trimethylsilyl
$TMSN_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
$Et_2O$=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane
HMPA=hexamethyl phosphoric triamide
HOAc or AcOH=acetic acid
TFA=trifluoroacetic acid
TFAA=trifluoroacetic anhydride
i-$Pr_2$NEt=diisopropylethylamine
$Et_3$N=triethylamine
NMM=N-methyl morpholine
DMAP=4-dimethylaminopyridine
$NaBH_4$=sodium borohydride
$NaBH(OAc)_3$=sodium triacetoxyborohydride
DIBALH=diisobutyl aluminum hydride LiAlH₄=lithium aluminum hydride
n-BuLi=n-butyllithium
Pd/C=palladium on carbon
PtO₂=platinum oxide
KOH=potassium hydroxide
NaOH=sodium hydroxide
LiOH=lithium hydroxide
K₂CO₃=potassium carbonate
NaHCO₃=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H₂O=1-hydroxybenzotriazole hydrate
HOAT=1-Hydroxy-7-azabenzotriazole
BOP reagent=benzotriazol-1-yloxy-tris (dimethylamino) phosphonium hexafluorophosphate
NaN(TMS)₂=sodium hexamethyldisilazide or sodium bis(trimethylsilyl)amide
Ph₃P=triphenylphosphine
Pd(OAc)₂=Palladium acetate
(Ph₃P)₄Pd°=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
N₂=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point

EXAMPLE 1

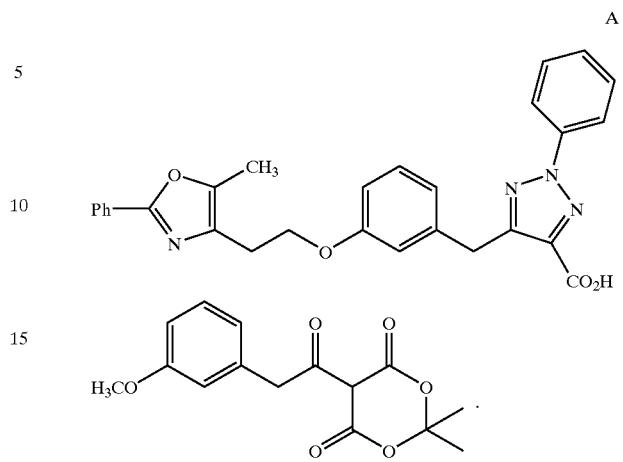

To a 0° C. solution of Meldrum's acid (9.4 g; 65 mmol) and pyridine (8.0 g; 100 mmol) in CH₂Cl₂ was added dropwise 3-methoxyphenylacetyl chloride (10.0 g; 54 mmol) over 2 h. The resultant mixture was stirred at RT for 2 h, then partitioned between aq. 2N HCl and CH₂Cl₂. The organic layer was dried (Na₂SO₄) and concentrated in vacuo to give crude Part A compound as an oil. This material was used in the next step without further purification.

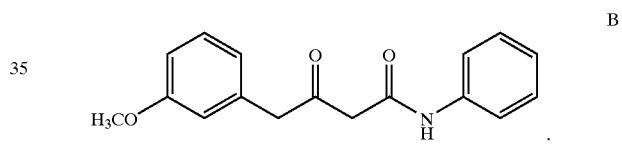

A solution of the crude Part A compound and aniline (5.0 g; 54 mmol) in toluene (20 mL) was heated to reflux for 3 h. The reaction solution was then washed with aq 1M HCl, then concentrated in vacuo to a small volume, upon which the desired product Part B compound (9.0 g; 59%) precipitated as a yellow solid.

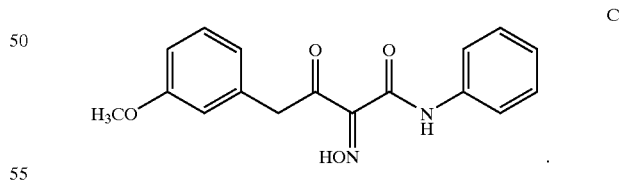

To 0° C. aqueous H₂SO₄ (5 mL of a 1.84 M solution) was added dropwise over 20 min a solution of Part B compound (6.0 g; 14 mmol), NaNO₂ (1.38 g; 20 mmol) and aq. 1 M NaOH (14 mL). The reaction mixture was stirred at 0° C. for 30 min; the resulting precipitate was filtered off and washed with H₂O to provide a yellow solid. This material was chromatographed (SiO₂; stepwise gradient from 5:1 to 3:1 hex:EtOAc) to give Part C compound (3.0 mg; 68%) as yellow crystals.

D

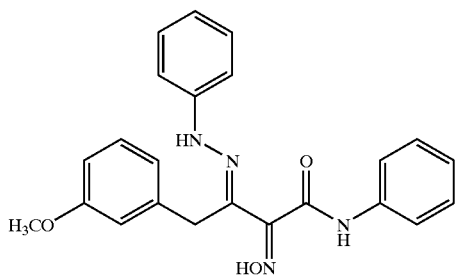

A solution of Part C compound (0.100 g; 0.32 mmol), phenylhydrazine (0.060 g; 0.55 mmol) and MgSO$_4$ (200 mg) was refluxed in EtOH (10 mL) for 2 h, at which point starting material had been consumed by analytical HPLC. Volatiles were removed in vacuo and the residue was recrystallized from hexane/CH$_2$Cl$_2$ (1:1) to provide Part D compound (90 mg; 70%) as yellow crystals.

E

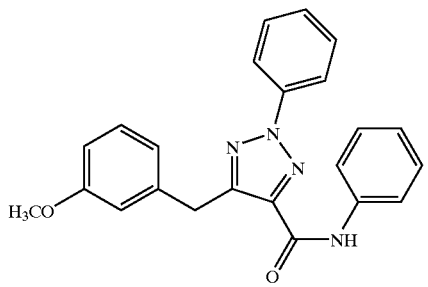

A mixture of Part D compound (90 mg; 0.22 mmol), TFAA (1 mL) and TFA (1 mL) was heated in a sealed tube at 45° C. for 10 h. At this point starting material had been consumed by analytical HPLC. Volatiles were removed in vacuo and the residue was partitioned between EtOAc and aq NaHCO$_3$. The organic phase was dried (Na$_2$SO$_4$) and concentrated in vacuo. The residue was chromatographed (SiO$_2$; 3:1 hex:EtOAc) to give Part E compound (30 mg; 35%) as a yellow solid.

F

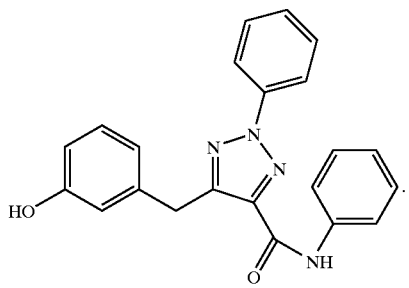

To a −70° C. solution of Part E compound (30 mg; 0.078 mmol) in CH$_2$Cl$_2$ (2.0 mL) was added dropwise BBr$_3$ (1.0 mL of a 1M solution in CH$_2$Cl$_2$). The mixture was allowed to warm to 0° C. and stirred at 0° C. for 3 h. The reaction was cooled to −20° C. and quenched with aq. NH$_4$Cl solution. This mixture was allowed to warm to RT and stirred for 30 min, then extracted with EtOAc. The organic phase was washed successively with aq 1 M HCl and water, then dried (Na$_2$SO$_4$) and concentrated in vacuo to give crude Part F compound (30 mg; 99%) as an oil which was used in the next step without further purification.

G

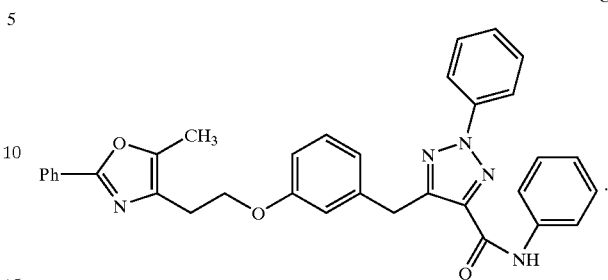

A mixture of Part F compound (30 mg; 0.081 mmol), 5-methyl 2-phenyl oxazole 4-ethanol mesylate (30 mg; 0.11 mmol; prepared as described in Example 11) and K$_2$CO$_3$ (500 mg; 3.61 mmol) in DMF (3 mL) was stirred at 80° C. for 12 h. LC/MS indicated that starting material had been completely consumed. The reaction mixture was filtered and the filtrate was concentrated in vacuo to give an oil, which was chromatographed (SiO$_2$; 3:1 hex:EtOAc) to give Part G compound (12 mg; 36%) as a light brown solid.

H

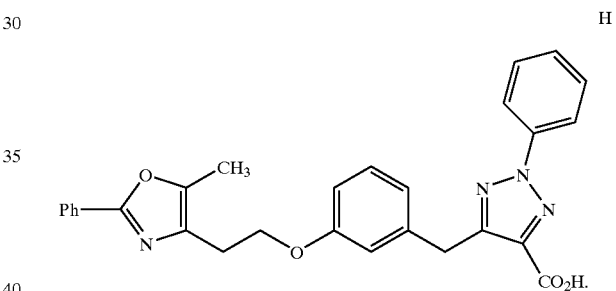

A solution of Part G compound (38 mg; 0.054 mmol) and KOH (200 mg; 3.6 mmol) in EtOH (30 mL) in a sealed tube was heated at 90° C. for 24 h. The reaction mixture was partitioned between EtOAc and aq 1 M HCl. The organic phase was washed with water, dried (Na$_2$SO$_4$) and concentrated in vacuo. The resulting oil was purified by preparative HPLC (YMC reverse phase column; continuous gradient from 30:70 B:A to 100% B) to give the title compound (8 mgs; 31%) as a solid. [M+H]$^+$=481.1

$^1$H NMR (CDCl$_3$; 400 MHz) δ: 2.43 (s, 3H), 3.05 (t, 2H; J=Hz), 4.26 (t, 2H; J=Hz), 4.35 (s, 2H), 6.73 (dd, 1H; J=Hz), 6.93 (d, 1H; J=Hz), 7.14 (dd, 2H; J=Hz), 7.41 (t, 1H; J=Hz), 7.47–7.54 (m, 5H), 8.05 (dd, 2H; J=Hz), 8.10 (dd, 2H; J=Hz), 11.32 (br s, 1H).

13C NMR (CDCl$_3$; 100 MHz) δ: 10.2, 24.5, 31.7, 65.6, 113.6, 114.7, 119.4, 121.6, 124.5, 126.7, 128.4, 129.2, 129.3, 129.5, 130.1, 131.9, 137.5, 139.1, 139.6, 146.8, 151.4, 157.9, 160.2, 163.5

EXAMPLE 1

Alternative Synthesis

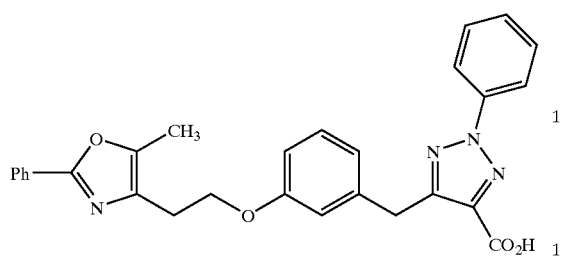

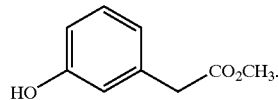

A solution of 3-hydroxyphenylacetic acid (3.89 g; 25 mmol) and concentrated H₂SO₄ (4 drops) in MeOH (30 mL) was heated at reflux overnight, then cooled to RT and concentrated in vacuo. The residue was partitioned between EtOAc (150 mL) and saturated aqueous NaHCO₃ (20 mL). The organic phase was dried (MgSO₄) and concentrated in vacuo to provide Part A compound (3.80 g; 92%) as an oil.

B

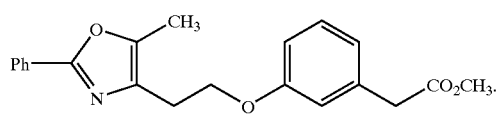

A mixture of Part A compound (5.50 g; 33 mmol), 5-methyl 2-phenyl oxazole 4-ethanol mesylate (5.43 g; 19 mmol; prepared as described in Example 11) and K₂CO₃ (5.50 g; 40 mmol) in MeCN (50 mL) was heated at reflux overnight, then cooled to RT and filtered. The filtrate was concentrated in vacuo, then partitioned between EtOAc (150 mL) and 1 N aqueous NaOH (15 mL). The organic phase was washed with 1 N aqueous NaOH (15 mL), dried (MgSO₄) and concentrated in vacuo. The residue was chromatographed (SiO₂; continuous gradient from hexane to 7:3 hexane:EtOAc over 10 min; then at 7:3 hex:EtOAc for 15 min, then continuous gradient from 7:3 to 2:3 hex:EtOAc for 5 min, then at 2:3 hex:EtOAc for 15 min) to provide Part B compound (4.30 g; 64%) as a viscous oil.

C

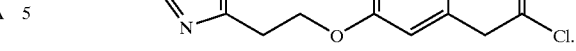

A mixture of Part B compound (4.30 g; 12 mmol) and LiOH.H₂O (1.02 g; 24 mmol) in 1:1 THF:H₂O (60 mL) was stirred overnight at RT, after which aqueous HCl (15 mL of a 1 N solution) was added. Organic solvents were removed in vacuo and the aqueous phase was extracted with EtOAc (2×120 mL). The combined organic extracts were dried (Na₂SO₄) and concentrated in vacuo. The residue was stripped from toluene (50 mL) to give Part C compound (4.12 g; 100%) which was used in the next step without further purification.

D

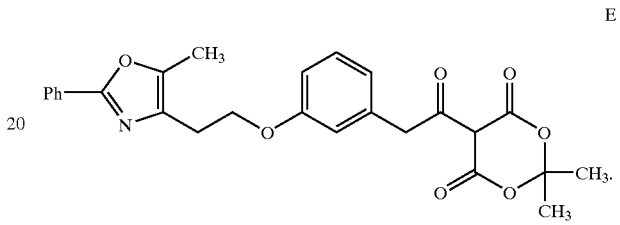

To a solution of Part C compound (4.12 g; 12 mmol) in anhydrous CH₂Cl₂ was added dropwise a solution of oxalyl chloride in CH₂Cl₂ (15.3 mL of a 2 M solution; 15 mmol). The mixture was stirred at RT for 2 h, then concentrated in vacuo. The residue was stripped from toluene (50 mL) to provide Part D as a yellow solid, which was used in the next step without further purification.

E

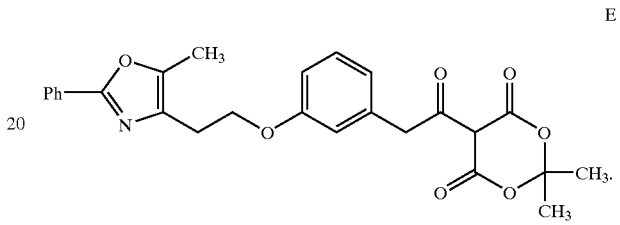

To a 0° C. solution of Meldrum's acid (2.16 g; 15 mmol) in anhydrous CH₂Cl₂ (44 mL) was added pyridine (3.63 mL; 45 mmol) dropwise over 15 min. A solution of Part D compound in anhydrous CH₂Cl₂ (44 mL) was, then added dropwise by syringe pump over 2 h. The reaction was warmed to RT and stirred at RT overnight, after which it was partitioned between EtOAc (300 mL) and aqueous HCl (30 mL of a 1 N solution). The organic phase was dried (MgSO₄) and concentrated in vacuo to give Part E compound.

F

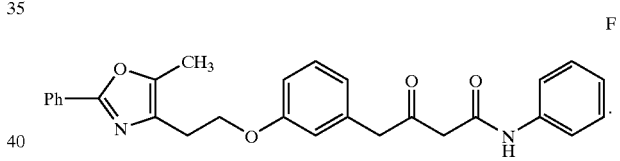

A solution of the crude Part E compound and aniline (1.1 mL; 12 mmol) in toluene (22 mL) was heated to reflux for 2 h. The reaction solution was partitioned between EtOAc (150 mL) and aqueous 1M HCl (20 mL); the organic phase was concentrated in vacuo. The residue was chromatographed (SiO₂; stepwise gradient from 100% hexane to 2:3 hex:EtOAc to 2:5 hex:EtOAc) to give Part F compound (4.27 g; 77% overall for 3 steps) precipitated as a yellow solid.

G

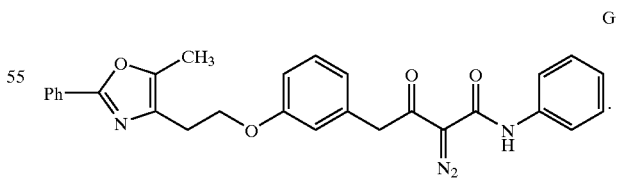

A solution of Part F compound (4.27 g; 9.40 mmol), p-toluenesulfonyl azide (2.50 mg; 12.7 mmol) and Et₃N (1.83 mL; 13.1 mmol) in CH₂Cl₂ (60 mL) was stirred at RT for 2.5 h. Volatiles were removed in vacuo, and the residue was chromatographed (SiO₂; stepwise gradient from 1:1 hex:EtOAc to 100% EtOAc to 10:1 EtOAc:MeOH) to provide Part G compound (3.50 g; 77%) as a yellow solid.

H

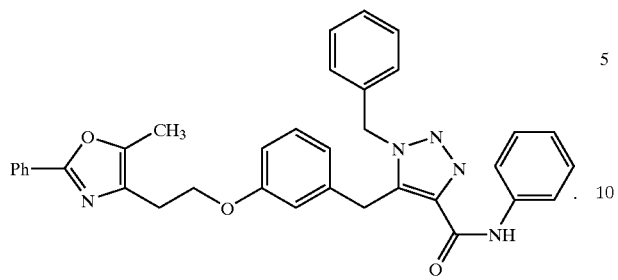

A mixture of Part G compound (3.50 mg; 7.24 mmol), benzylamine (1.13 mL; 11.1 mmol) and TiCl₄ (7.24 mL of a 1 M solution in CH₂Cl₂; 7.24 mmol) in DCE (100 mL) was heated at 88° C. in a sealed tube for 2 h. The reaction mixture was cooled to RT and partitioned between EtOAc (200 mL) and H₂O (50 mL). The organic phase was dried (MgSO₄) and concentrated in vacuo. The residue was chromatographed (SiO₂; continuous gradient from 100% hexane to 1:1 hex:EtOAc) to give Part H compound (2.30 g; 55%) as a light-brown solid foam.

I

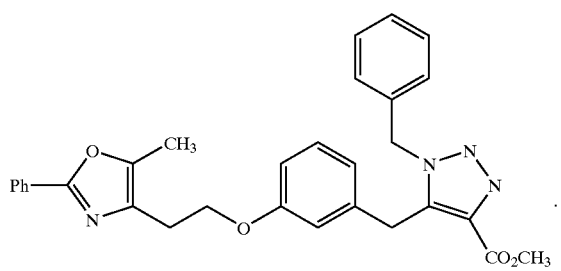

A mixture of Part H compound (2.0 g; 3.51 mmol) and KOH (4.35 g; 77 mmol) was heated in EtOH (75 mL) at 118° C. for 3 h. At this point, HPLC/MS showed that reaction was complete. The reaction mixture was cooled to RT and partitioned between EtOAc (150 mL), H₂O (20 mL) and excess concentrated HCl (6 mL). The organic phase was washed with H₂O, dried (MgSO₄) and concentrated in vacuo to give the crude acid as a brown solid. This material was dissolved in a solution of saturated HCl in MeOH (30 mL) and the reaction was stirred at RT for 4 days, then concentrated in vacuo. The residue was partitioned between EtOAc (150 mL) and saturated aqueous NaHCO₃ (20 mL). The organic phase was concentrated in vacuo and the residue was chromatographed (SiO2; continuous gradient from 100% hexane to 1:1 hex:EtOAc over 20 min, then 1:1 hex:EtOAc for 20 min) to give Part I compound (1.35 g; 76%) as a solid.

J

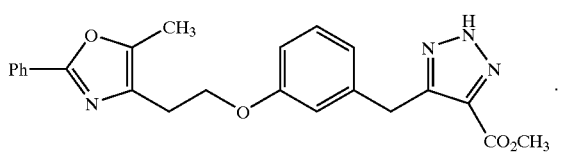

A mixture of Part I compound (1.35 g; 2.65 mmol) and 10% palladium on carbon (1.35 g) in MeOH (60 mL) and a solution of saturated HCl in MeOH (1 mL) was stirred under an atmosphere of H₂ (balloon) for 70 h. The balloon was removed, additional MeOH (60 mL) was added and the mixture was heated to reflux and filtered hot. The filtrate was concentrated in vacuo to give Part J compound (1.10 g; 91%) as a white solid.

K

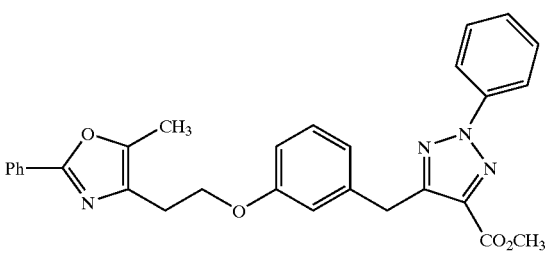

To a mixture of Part J compound (25 mg; 0.55 mmol), phenyl boronic acid (22 mg; 1.80 mmol) and Cu(OAc)₂ (16 mg; 0.88 mmol) were added pyridine (50 μL) and Et₃N (50 μL). The mixture was stirred at RT overnight, then was partitioned between EtOAc and H₂O (10 mL each). The organic phase was concentrated in vacuo, and the residue was chromatographed (SiO₂; stepwise gradient from 5:1 to 3:1 hexane:EtOAc) to give Part K compound (3 mg; 10%) as an oil.

L

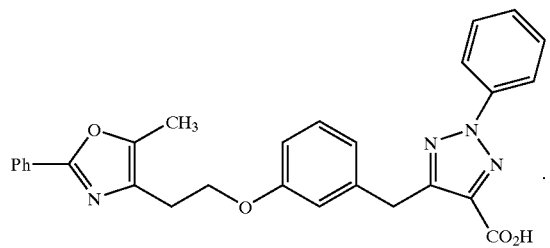

A mixture of Part K compound (3 mg; 0.006 mmol) and LiOH.H₂O (2 mg; 0.48 mmol) in 1:1 THF:H₂O (0.60 mL) was stirred for 4 h at RT, then the THF was removed in vacuo. Aqueous 1 N HCl was added until the pH was ~3, and the mixture was extracted with EtOAc (5 mL). The organic phase was concentrated in vacuo, and the residue was purified by preparative HPLC (YMC reverse-phase ODS 20×100 mm column; flow rate=20 mL/min; 10 min continuous gradient from 25:75 B:A to 100% B+5 min hold-time at 100% B, where solvent A=90:10:0.1H₂O:MeOH:TFA and solvent B=90:10:0.1 MeOH:H₂O:TFA) to give the title compound (1.2 mg; 41%) as a colorless oil. [M+H]⁺=481

EXAMPLE 2

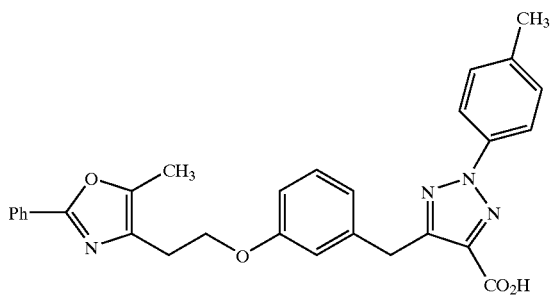

The method described in Example 1 was used except that 4-methylphenylhydrazine was used instead of phenylhydrazine to prepare the title compound. [M+H]$^+$=495.0

EXAMPLE 3

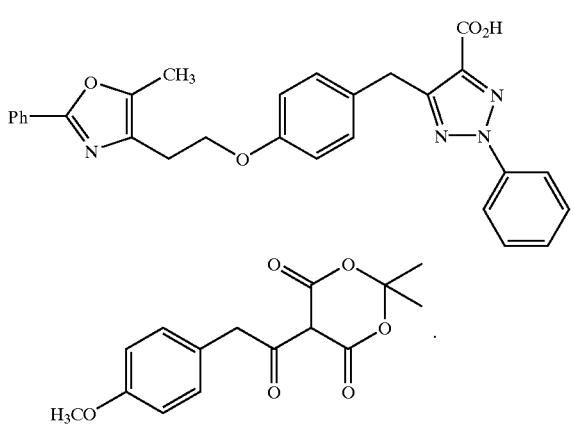

To a 0° C. solution of Meldrum's acid (9.4 g; 65 mmol) and pyridine (8.0 g; 100 mmol) in CH$_2$Cl$_2$ was added dropwise 4-methoxyphenylacetyl chloride (10.0 g; 54 mmol) over 2 h. The resultant mixture was stirred at RT for 2 h, then partitioned between aq. 2N HCl and CH$_2$Cl$_2$. The organic layer was dried (Na$_2$SO$_4$) and concentrated in vacuo to give crude Part A compound as an oil. This material was used in the next step without further purification.

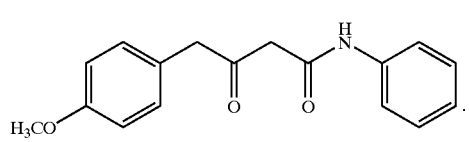

A solution of the crude Part A compound and aniline (5.0 g; 54 mmol) in toluene (20 mL) was heated to reflux for 3 h. The reaction solution was then washed with aq 1M HCl, then concentrated in vacuo to a small volume, upon which the desired product Part B compound (7.5 g; 49%) precipitated as a yellow solid.

To 0° C. aqueous H$_2$SO$_4$ (5 mL of a 1.84 M solution) was added dropwise over 20 min a solution of Part B compound (2.0 g; 7.1 mmol), NaNO$_2$ (0.73 g; 10.6 mmol), aq. 1 M NaOH (7.06 mL) and THF (50 mL). The reaction mixture was stirred at 0° C. for 30 min; the resulting precipitate was filtered off and washed with H$_2$O to provid a yellow solid. This material was chromatographed (SiO$_2$; stepwise gradient from 5:1 to 3:1 hex:EtOAc) to give Part C compound (2.00 g; 91%) as yellow crystals.

A solution of Part C compound (0.250 g; 0.80 mmol), phenylhydrazine (0.097 g; 0.90 mmol) and MgSO$_4$ (2 g) was refluxed in EtOH (10 mL) for 2 h, at which point starting material had been consumed by analytical HPLC. Volatiles were removed in vacuo and the residue was chromatographed (SiO$_2$; stepwise gradient from 3:1 to 1:1 hex:EtOAc) to provide Part D compound (200 mg; 62%) as a yellow solid.

A mixture of Part D compound (30 mg; 0.075 mmol), TFAA (1 mL) and TFA (1 mL) was heated in a sealed tube at 45° C. for 10 h. At this point starting material had been consumed by analytical HPLC. Volatiles were removed in vacuo and the residue was partitioned between EtOAc and aq NaHCO$_3$. The organic phase was dried (Na$_2$SO$_4$) and concentrated in vacuo. The residue was chromatographed (SiO$_2$; 3:1 hex:EtOAc) to give Part E compound (25 mg; 86%) as a yellow solid.

F

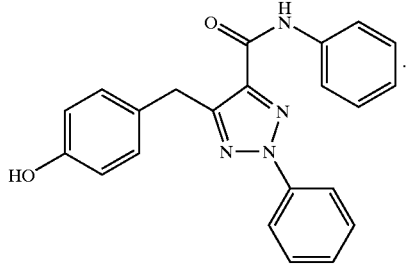

To a −70° C. solution of Part E compound (25 mg; 0.065 mmol) in CH₂Cl₂ (2.0 mL) was added dropwise BBr₃ (1.0 mL of a 1 M solution in CH₂Cl₂). The mixture was allowed to warm to 0° C. and stirred at 0° C. for 3 h. The reaction was cooled to −20° C. and quenched with aq. NH₄Cl solution. This mixture was allowed to warm to RT and stirred for 30 min, then extracted with EtOAc. The organic phase was washed successively with aq 1 M HCl and water, then dried (Na₂SO₄) and concentrated in vacuo to give crude Part F compound (30 mg) as an oil which was used in the next step without further purification.

G

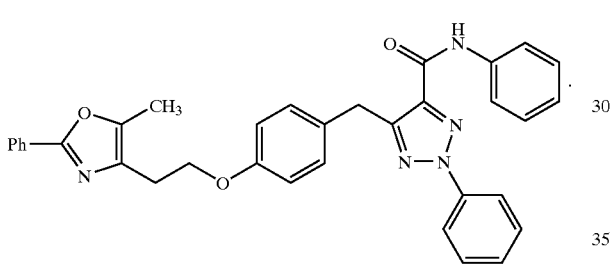

A mixture of Part F compound (30 mg; 0.081 mmol), 5-methyl 2-phenyl oxazole 4-ethanol mesylate (30 mg; 0.11 mmol; prepared as described in Example 11) and K₂CO₃ (500 mg; 3.61 mmol) in DMF (3 mL) was stirred at 80° C. for 12 h. LC/MS indicated that starting material had been completely consumed. The reaction mixture was filtered and the filtrate was concentrated in vacuo to give an oil, which was chromatographed (SiO₂; 3:1 hex:EtOAc) to give Part G compound (13 mg; 28% over 2 steps) as a solid.

H

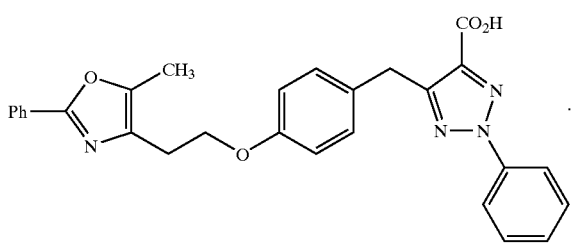

A solution of Part G compound (0.013 g; 0.023 mmol) and KOH (200 mg; 3.6 mmol) in EtOH (30 mL) in a sealed tube was heated at 90° C. for 24 h. The reaction mixture was partitioned between EtOAc and aq 1 M HCl. The organic phase was washed with water, dried (Na₂SO₄) and concentrated in vacuo. The resulting oil was purified by preparative HPLC (as described for the purification of BMS-460913; see below) to give the title compound (9 mg; 81%) as a solid. [M+H]⁺=481.1

EXAMPLE 4

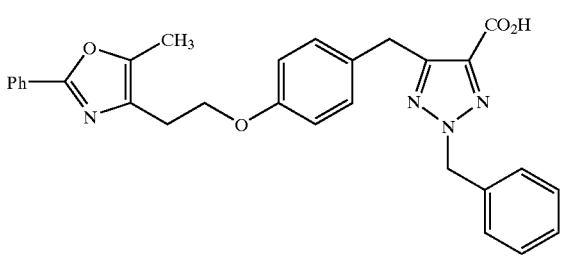

The procedure of Example 3 was employed to prepare the title compound except that 4-methylphenylhydrazine was used in place of phenylhydrazine. [M+H]⁺=495.1.

EXAMPLE 5

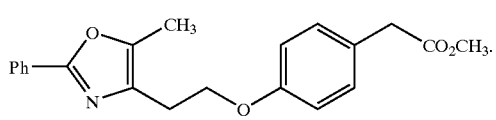

A

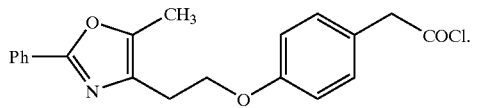

To a 0° C. solution of methyl 4-hydroxyphenylacetate (2.66 g; 1.6 mmol), 5-phenyl 2-methyl oxazole-3-ethanol (3.25 g; 1.6 mmol) and Ph₃P (5.0 g; 1.9 mmol) in anhydrous THF (30 mL) was added DEAD (3.5 g; 2.0 mmol) dropwise. The reaction mixture was stirred at 0° C. for 30 min and then was allowed to warm to RT and stirred at RT overnight. Volatiles were removed in vacuo and the residue was chromatographed (SiO₂; stepwise gradient; hexane:EtOAc 5:1 to 5:2) to give Part A compound (3.5 g; 62%) as a white solid.

B

A solution of Part A compound (2.85 g; 0.812 mmol) and aqueous LiOH (2.0 mL of a 1 M solution; 2.0 mmol) in THF (2 mL) was stirred at RT for 3 h. At this point, HPLC/MS indicated that all starting material had been consumed. Volatiles were removed in vacuo and the reaction was acidified with aqueous 1 N HCl. The aqueous phase was extracted with EtOAc (2×250 mL); the combined organic extracts were dried (Na₂SO₄) and concentrated in vacuo to give the crude phenylacetic acid. To a solution of the crude acid was added oxalyl chloride (10 mL of a 2 M solution in CH₂Cl₂ and the reaction mixture was stirred at RT for 3 h. Volatiles were removed in vacuo to give Part B compound as a solid which was used in the next reaction without further purification.

C

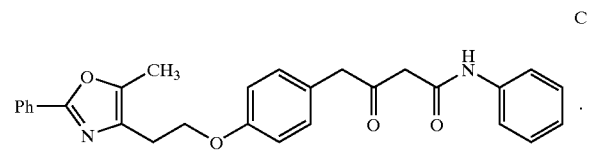

To a 0° C. solution of Meldrum's acid (980 mg; 678 mmol) and pyridine (1.0 mL; 10 mmol) in anhydrous $CH_2Cl_2$ (10 mL) was added dropwise a solution of Part B compound (2.0 g; 5.65 mmol) in $CH_2Cl_2$ (5 mL) over 2 h. The reaction mixture was allowed to warm to RT and stirred at RT for 2 h. The mixture was then acidified by addition of excess aqueous 2N HCl and extracted with $CH_2Cl_2$ (2×25 mL). The combined organic extracts were dried ($Na_2SO_4$) and concentrated in vacuo to provide the crude Meldrum's acid adduct. A solution of this crude product and aniline (600 µL) in toluene (10 mL) was refluxed for 3 h. The reaction was cooled to RT and washed with aqueous 1N HCl. Volatiles were removed in vacuo to give Part C compound (2.50 g; 97%) as a yellow solid.

D

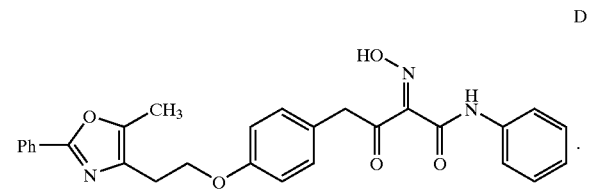

To a 0° C. solution of aqueous $H_2SO_4$ (0.60 mL of a 1.84 M solution; 1.10 mmol) was added dropwise a solution of Part C compound (300 mg, 0.60 mmol), $NaNO_2$ (64 mg; 1.0 mmol) and aqueous 1N NaOH (0.70 mL; 0.70 mmol) in THF (10 mL) over 20 min. The reaction mixture was stirred at RT for 30 min, after which the precipitate was filtered off and washed with $H_2O$ to give a yellow solid. This material was chromatographed ($SiO_2$; hexane:EtOAc 5:1 to 3:1) to give Part D compound (250 mg; 84%) as a yellow solid.

E

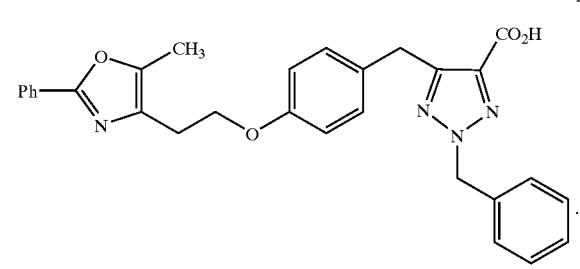

A solution of benzylhydrazine.2HCl (41 mg; 0.21 mmol) and sodium ethoxide (200 µL of a 21% solution in EtOH; 0.42 mmol) in ethanol (5 mL) was stirred at RT for 2 h. Part D compound (100 mg; 0.21 mmol) and anhydrous MgSO4 (200 mg) were then added and the reaction mixture was heated at 80° C. in an oil bath for 16 h. TLC indicated that all starting material had been consumed. Volatiles were removed in vacuo, and the residue (the crude triazole-anilide) was dissolved in 2-ethoxyethanol (10 mL). This solution was added to a solution of KOH (1.0 g; 8 mmol) in 2-ethoxyethanol (20 mL) at 150° C. The reaction mixture was heated at 150° C. for 30 min. HPLC/MS indicated that all of the anilide had been consumed at this point. The reaction mixture was cooled to RT, acidified with excess aqueous 1N HCl, and extracted with EtOAc (3×). The combined organic extracts were dried (Na2SO4) and concentrated in vacuo. The residue was purified by preparative HPLC (YMC reverse-phase ODS 30×250 mm column; flow rate=25 mL/min; 30 min continuous gradient from 30:70 B:A to 100% B+10 min hold-time at 100% B, where solvent A=90:10:0.1$H_2O$:MeOH:TFA and solvent B=90:10:0.1 MeOH:$H_2O$:TFA) to give the title compound (61 mg; 58%) as a white solid after stripping from MeOH. $[M+H]+=495.0$.

$^1$H NMR (DMSO; 400 MHz) 2.34 (s, 3H), 2.87–2.92 (t, J=6.6 Hz, 2H), 4.14–4.17 (m, 4H), 5.65 (s, 2H), 6.82–6.85 (d, J=8.76 Hz, 2H), 7.09–7.11 (d, J=8.32 Hz, 2H), 7.26–7.40 (m, 5H), 7.42–7.55 (m, 3H), 7.94–7.97 (m, 2H).

EXAMPLE 6

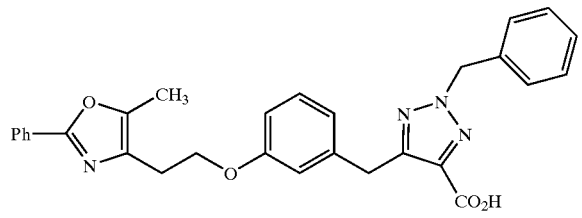

The procedure of Example 5 was employed to prepare the title compound except that methyl 3-hydroxyphenyl-acetate was used as the starting material in place of methyl 4-hydroxyphenyl-acetate. The title compound (6 mg) was obtained as a solid. $[M+H]^+=495.2$.

EXAMPLE 7

A

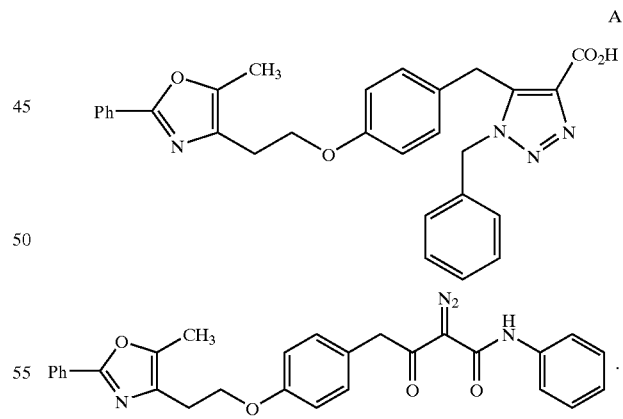

A solution of Example 5 Part C compound (100 mg; 0.22 mmol), p-toluenesulfonyl azide (60 mg; 0.3 mmol) and $Et_3N$ (50 µL; 0.3 mmol) in $CH_2Cl_2$ (3 mL) was stirred at RT for 3 h, at which point the reaction was complete by TLC. Volatiles were removed in vacuo, and the residue was chromatographed ($SiO_2$; stepwise gradient from 1:1 hex:EtOAc to EtOAc to $CH_2Cl_2$:MeOH:$Et_3N$ 10:1:1) to provide Part A compound (100 mg; 95%) as a yellow solid.

B

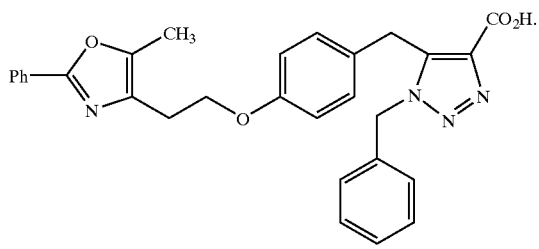

A solution of Part A compound (100 mg; 0.21 mmol), benzylamine (30 μL; 0.30 mmol) and TiCl$_4$ (300 μL of a 1 M solution in CH$_2$Cl$_2$; 0.30 mmol) in 1,2 dichloroethane (5 mL) was heated at 88° C. in a sealed tube for 18 h. At this point LC/MS showed the formation of the desired triazole. The reaction mixture was cooled to RT and partitioned between EtOAc and H$_2$O (100 mL each). The organic phase was dried (Na$_2$SO$_4$) and concentrated in vacuo to give the crude triazole-anilide as an oil. A mixture of this crude material and KOH (300 mg) was heated in EtOH (3 mL) at 80° C. for 3 h. At this point, HPLC/MS showed that reaction was complete. The reaction mixture was cooled to RT and partitioned between EtOAc and excess aqueous 1 M HCl. The organic phase was washed with H$_2$O, dried (Na2SO4) and concentrated in vacuo. The residue was purified by preparative HPLC (YMC reverse-phase ODS 30×250 mm column; flow rate=25 mL/min; 30 min continuous gradient from 30:70 B:A to 100% B+10 min hold-time at 100% B, where solvent A=90:10:0.1H$_2$O:MeOH:TFA and solvent B=90:10:0.1 MeOH:H$_2$O:TFA) to give the title compound (48 mg; 46%) as a solid. [M+H]$^+$=495.1

EXAMPLE 8

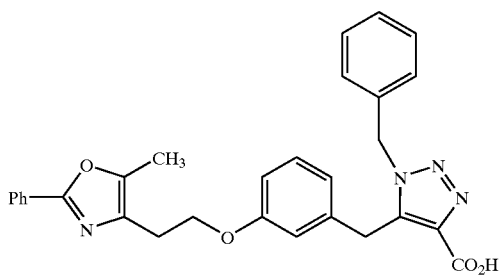

The synthetic sequence described in Example 7 was used for the preparation of the title compound except that the corresponding 1,3-substituted intermediate diazo-β-ketoamide

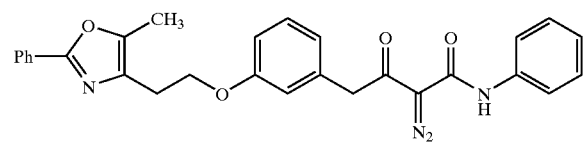

was used instead of the Example 7 Part A 1,4-substituted intermediate. This 1,3-substituted intermediate was prepared according to the procedure described for the synthesis of Example 5 Part C compound, except that methyl 3-hydroxyphenylacetate was used instead of methyl 4-hydroxyphenylacetate. [M+H]$^+$=495.2.

EXAMPLES 9 AND 10

The procedures of Examples 7 and 8 were employed to prepare the following analogs:

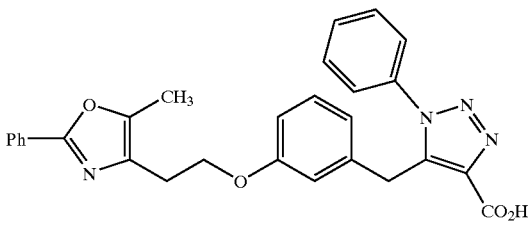

EXAMPLE 9

[M+H]$^+$=481.1

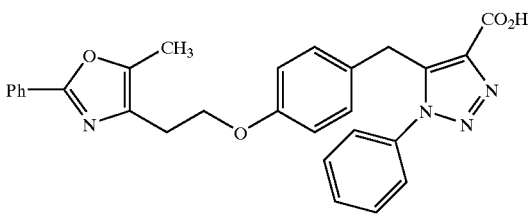

EXAMPLE 10

[M+H]$^+$=481.1.

EXAMPLE 11

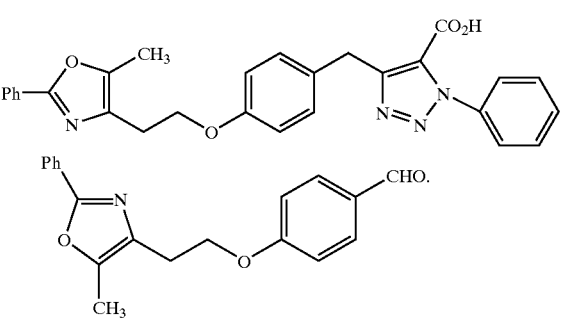

To a 0° C. solution of 4-hydroxybenzaldehyde (1.70 g, 12.3 mmol), 5-phenyl-2-methyl-oxazole-4-ethanol (Maybridge; 2.50 g, 14.0 mmol) and Ph$_3$P (4.20 g, 16.0 mmol) in dry THF (30 mL) was added dropwise DEAD (3.20 g, 15.0 mmol). The solution was stirred at 0° C. for 0.5 h, then was allowed to warm to RT and stirred overnight. The orange-red solution was concentrated in vacuo and the residue was chromatographed (stepwise gradient from 5:1 to 5:2 hex:EtOAc) to give Part A compound (2.47 g, 65%) as a clear, slightly yellow viscous oil.

Alternative Procedure for Preparing Part A aldehyde:

(1)

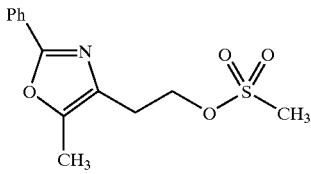

To a −5° C. solution of 5-phenyl-2-methyl-oxazole-4-ethanol (20.00 g, 0.098 mol) in CH$_2$Cl$_2$ (100 mL) was added methanesulfonyl chloride (12.40 g, 0.108 mol) in one portion (exothermic reaction). After recooling to −5° C., Et$_3$N (11.1 g, 0.110 mol) was added slowly over 30 min (internal temperature <3° C.). The reaction was allowed to warm to RT and stirred for 1 h (reaction monitored by analytical HPLC), at which point starting material had been consumed. The reaction was washed with aqueous HCl (2×50 mL of a 3N solution). The combined aqueous layers were extracted with CH$_2$Cl$_2$ (50 mL). The combined organic extracts were successively washed with satd. aqueous NaHCO$_3$ and brine (50 mL each), dried (Na$_2$SO$_4$), and concentrated to ~30 mL volume. Methyl tert-butyl ether (120 mL) was added and the mixture was stirred; a white solid was formed. The mixture was cooled to −20° C. for complete crystallization. The product was filtered and vacuum-dried to give the product mesylate (23.3 g, 85%) as a white solid. The mother liquor was concentrated in vacuo and recrystallized from methyl tert butyl ether/heptane to give a second crop of product mesylate (3.3 g, 12%; total yield=97%).

(2)

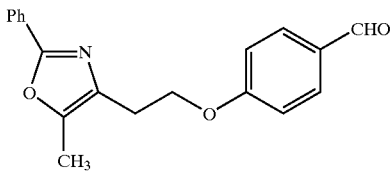

A mixture of the above mesylate (13.6 g, 0.048 mol), 4-hydroxybenzaldehyde (7.09 g, 0.058 mol) and K$_2$CO$_3$ (9.95 g, 0.072 mol) in DMF (110 mL) was heated at 100° C. for 2 h (reaction complete by analytical HPLC). The mixture was allowed to cool to RT and then poured into ice-water (400 mL) and stirred for 30 min. The solid product was filtered and washed with cold water (3×25 mL) and dried in vacuo at 50°–60° C. overnight. The crude product was crystallized from methyl tert-butyl ether/hexane to give (12.2 g, 82%; 2 crops) of Part A compound as a white solid.

B

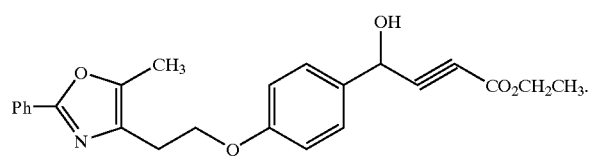

To a −78° C. solution of ethyl propiolate (256 mg; 2.6 mmol) in THF (12 mL) was added dropwise n-butyllithium (1.04 mL of a 2.5 M solution in hexane; 2.6 mmol). The solution was stirred at −78° C. for 30 min; a solution of Part A aldehyde (800 mg; 2.6 mmol) in THF (3 mL) was then added dropwise. The reaction was stirred at −70° C. for 1 h, then quenched by dropwise addition of saturated aqueous NH$_4$Cl. The mixture was allowed to warm to RT, then extracted with EtOAc. The organic phase was washed with H$_2$O, dried (Na$_2$SO$_4$) and concentrated in vacuo to give crude Part B compound as an oil, which was used in the next step without further purification.

C

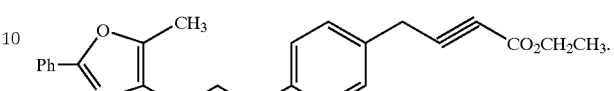

To a 0° C. solution of the crude Part B compound from above in dry MeCN (5 mL) were successively added Et$_3$SiH (620 μL; 3.97 mmol) and BF$_3$.OEt$_2$ (384 μL; 3.1 mmol). The reaction mixture was allowed to warm to RT and stirred at RT for 2 h, at which point analytical HPLC showed that all starting material had been consumed. Volatiles were removed in vacuo and the residue was partitioned between H$_2$O and EtOAc. The organic phase was washed with aqueous NaHCO$_3$ and then concentrated in vacuo. The crude product was chromatographed (SiO$_2$; 4:1 hexane:EtOAc) to give Part C compound (514 mg; 50% over 2 steps) as white crystals.

D

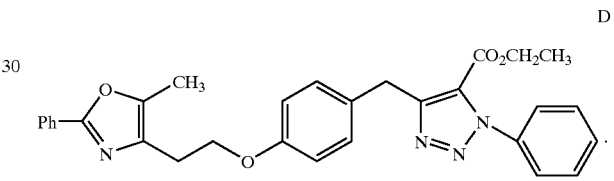

A mixture of Part C compound (233 mg; 0.60 mmol) and phenyl azide (2 mL; prepared from aniline according to the procedure in Organic Syntheses Collective Volume IV, p. 75–77) in toluene (50 mL) was heated in a sealed tube at 130° C. for 18 h. The mixture was cooled to RT and concentrated in vacuo. The brown residue was chromatographed (SiO$_2$; stepwise gradient from 4:1 to 2:1 hexane:EtOAc) to give Part D compound (50 mg; 16%) as well as the isomeric product Part E compound

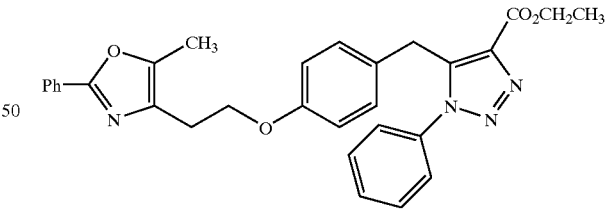

(100 mg; 32%) as a solid. [M+H]$^+$=509.0

F

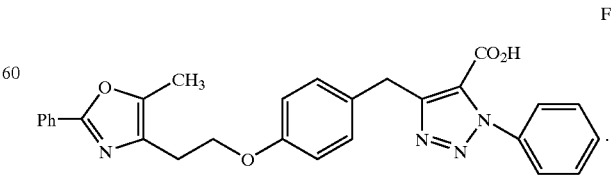

A solution of Part D compound (50 mg; 0.098 mmol) and aqueous 1 M LIOH (1 mL; 1.0 mmol) in THF (5 mL) was stirred at RT overnight. The reaction was acidified with 1 M HCl (2 mL; 2.0 mmol) and extracted with EtOAc (2×). The combined organic extracts were washed with H₂O and concentrated in vacuo. The residue was purified by preparative HPLC to give the title compound as a white solid (38 mg; 13% for 2 steps). [M+H]⁺=481.2

EXAMPLE 12

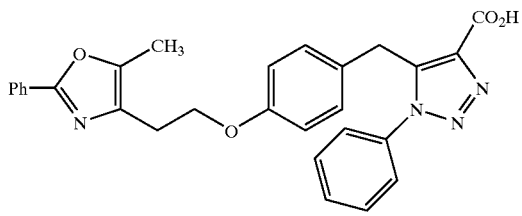

A solution of Example 11 Part E compound (50 mg; 0.098 mmol)

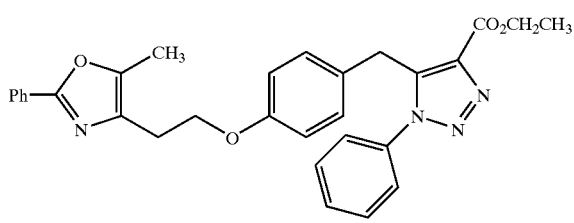

and aqueous 1 M LiOH (1 mL; 1.0 mmol) in THF (5 mL) was stirred at RT overnight. The reaction was acidified with 1 M HCl (2 mL; 2.0 mmol) and extracted with EtOAc (2×). The combined organic extracts were washed with H₂O and concentrated in vacuo. The residue was purified by preparative HPLC to give the title compound as a white solid (80 mg; 26% for 2 steps). [M+H]⁺=481.1

EXAMPLE 13

A

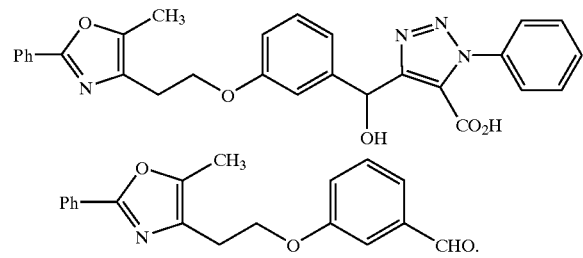

This intermediate was prepared employing the Example 11 Part A procedure for the corresponding 1,4 derivative except that 3-hydroxybenzaldehyde was used as starting material instead of 4-hydroxybenzaldehyde.

B

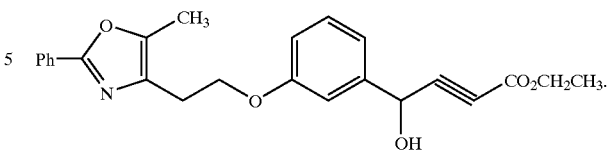

To a −78° C. solution of ethyl propiolate (256 mg; 2.6 mmol) in THF (12 mL) was added dropwise n-butyllithium (1.04 mL of a 2.5 M solution in hexane; 2.6 mmol). The solution was stirred at −78° C. for 30 min; a solution of Part A aldehyde (800 mg; 2.6 mmol) in THF (3 mL) was then added dropwise. The reaction was stirred at −70° C. for 1 h, then quenched by dropwise addition of saturated aqueous NH₄Cl. The mixture was allowed to warm to RT, then extracted with EtOAc. The organic phase was washed with H₂O, dried (Na₂SO₄) and concentrated in vacuo to give crude Part B compound as an oil, which was used in the next step without further purification.

C. and D.

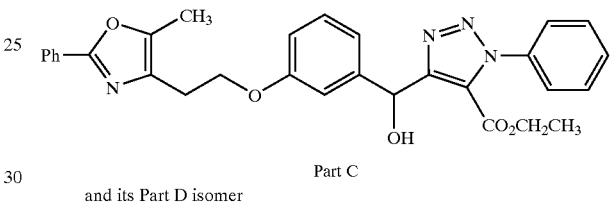

Part C
and its Part D isomer

A mixture of Part A compound (230 mg; 0.57 mmol) and phenyl azide (2 mL; prepared from aniline according to the procedure in Organic Syntheses Collective Volume IV, p. 75–77) in toluene (50 mL) was heated in a sealed tube at 130° C. for 18 h. The mixture was cooled to RT and concentrated in vacuo. The brown residue was chromatographed (SiO₂; stepwise gradient from 4:1 to 2:1 hexane:EtOAc) to give Part C compound (70 mg; 23%) as well as the isomeric product Part D compound

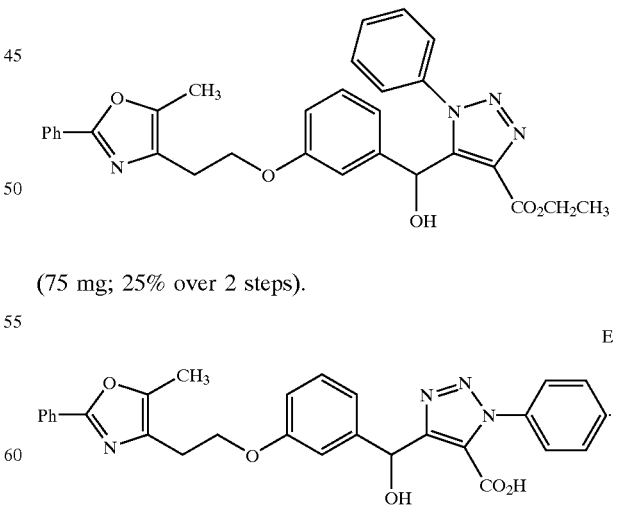

(75 mg; 25% over 2 steps).

E

A solution of Part C compound (45 mg; 0.085 mmol) and aqueous 1 M LiOH (1 mL; 1.0 mmol) in THF (5 mL) was stirred at RT for 24 h. The reaction was acidified with 1 M HCl (2 mL; 2.0 mmol) and extracted with EtOAc (2×). The

87 combined organic extracts were washed with H$_2$O and concentrated in vacuo. The residue was purified by preparative HPLC (YMC reverse phase ODS 30×250 mm column; continuous 30 min gradient from 70:30 A:B to 100% B, where solvent A=90:10:0.1H$_2$O:MeOH:TFA and B=90:10:0.1 MeOH:H$_2$O:TFA; flow rate=25 mL/min) to give the title compound as a white solid (34 mg; 80%). [M+H]$^+$=497.1

EXAMPLE 14

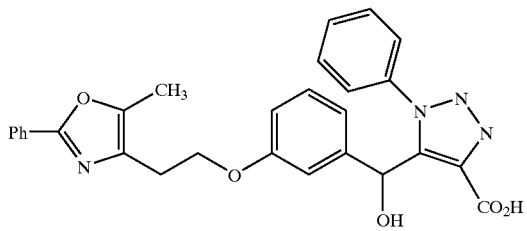

A solution of Example 13 Part D compound (45 mg; 0.085 mmol) and aqueous 1 M LiOH (1 mL; 1.0 mmol) in THF (5 mL) was stirred at RT overnight. The reaction was acidified with 1 M HCl (2 mL; 2.0 mmol) and extracted with EtOAc (2×). The combined organic extracts were washed with H$_2$O and concentrated in vacuo. The residue was purified by preparative HPLC (conditions as for the purification of Example 13 compound) to give the title compound (32 mg; 75%) as a white solid. [M+H]+=497.1

EXAMPLE 15

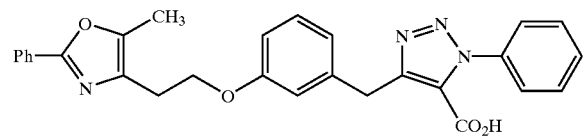

To a 0° C. solution of Example 13 Part C compound (35 mg; 0.067 mmol) in dry MeCN (2.5 mL) were successively added Et$_3$SiH (12 mg; 0.10 mmol) and BF$_3$.OEt$_2$ (14 mg; 0.10 mmol). The reaction mixture was allowed to warm to RT and stirred at RT for 2 h, at which point analytical HPLC showed that all starting material had been consumed. Volatiles were removed in vacuo and the residue was partitioned between H$_2$O and EtOAc. The organic phase was washed with aqueous NaHCO$_3$ and then concentrated in vacuo. The crude product was hydrolyzed using 1 M aqueous LiOH/THF as described for the synthesis of Examples 13 and 14 to give the title compound (26 mg; 80% over 2 steps) as a yellow solid. [M+H]$^+$=481.1

88

EXAMPLE 16

A

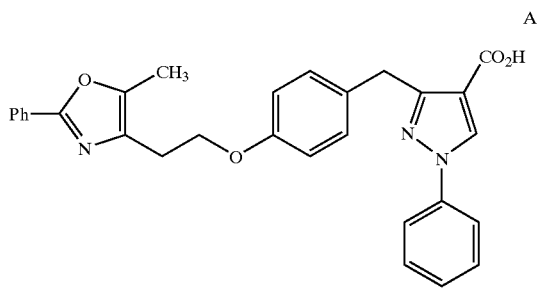

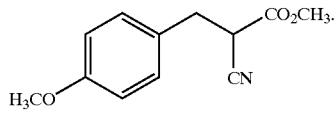

To a solution of methyl cyanoacetate (26 g; 256 mmol) and sodium methoxide in MeOH (152 mL of a 0.5 M solution; 76 mmol) was added 4-methoxybenzyl chloride (10.0 g; 64 mmol) at RT over 1 h. The resulting milky suspension was heated to reflux for 3 h, after which volatiles were removed in vacuo. The residue was partitioned between H$_2$O and Et$_2$O. The organic phase was washed with H$_2$O, dried (Na$_2$SO$_4$), and partially concentrated in vacuo. A white solid precipitate was filtered off, and the filtrate was concentrated in vacuo to give an oil. This crude material was purified by Kugelrohr distillation (b.p.=180° C. @ 0.3 mm Hg) to give Part A compound (7.6 g; 54%) as a clear oil which at RT crystallized as a white solid.

B

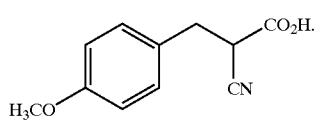

A solution of Part A compound (7.6 g; 35 mmol) and NaOH (4.4 g; 110 mmol) in H$_2$O (50 mL) was stirred at RT for 1 h. The reaction mixture was partitioned between Et$_2$O (50 mL) and concentrated HCl (12 mL). The organic phase was washed with water, concentrated in vacuo and dried (Na$_2$SO$_4$) to give Part B compound (7.1 g; 96%) as a residue which became a white solid at RT.

C

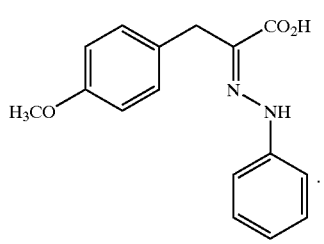

A diazotized solution of aniline (prepared according to the procedure of Walker, T. K., *J. Chem. Soc.*, 1924, 1622–1625) in HCl was treated with NaOAc (338 mg; 4.9 mmol; to remove free HCl) followed by addition of Part B compound (1 g; 4.9 mmol) at 0° C. (resulting in evolution of CO$_2$). The reaction mixture was stirred at 0° C. for 24 h. A yellow syrup was separated from the aqueous phase and dissolved in CH$_2$Cl$_2$. The aqueous phase was extracted with CH$_2$Cl$_2$ (2×20 mL); the combined organic extracts were dried (Na₂SO₄) and concentrated in vacuo to give Part C compound (40 mg; 7%) as an oil.

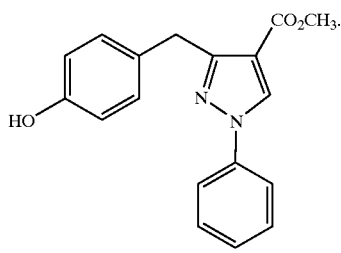

D

To a −78° C. solution of Part C compound (20 mg; 0.062 mmol) in CH₂Cl₂ (2 mL) was added BBr₃ (20 mg; 0.079 mmol). The reaction was stirred at −78° C. and then allowed to warm to RT. Workup (details needed) gave Part D compound (20 mg) as a crude oil which was used in the next reaction without further purification.

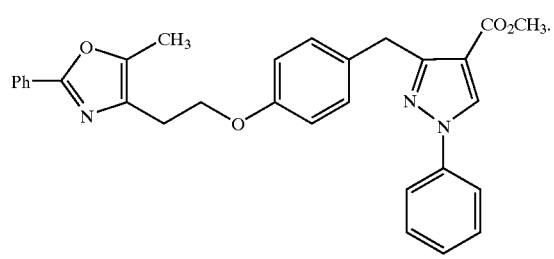

E

A mixture of Part D compound (20 mg; 0.064 mmol), the mesylate (30 mg; 0.11 mmol)

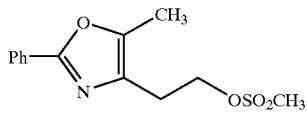

K₂CO₃ (100 mg; 0.72 mmol) in MeCN (5 mL) was heated at 80° C. Workup gave crude Product E (20 mg) as an oil which was used in the next step without further purification.

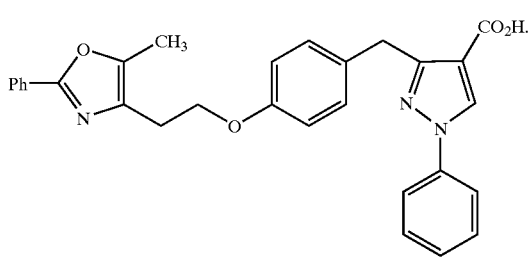

F

A solution of crude Product E and aqueous LiOH (1 mL of a 1M solution) in THF was stirred at RT overnight. The reaction was acidified with 1 M HCl (2 mL) and extracted with EtOAc (2×). The combined organic extracts were washed with H₂O and concentrated in vacuo. The residue was purified by preparative HPLC (as described for the purification of Example 13 compound) to give the title compound (7 mg; 22%) as a white solid. [M+H]⁺=480.2

EXAMPLE 17

The following compound was prepared employing the procedure of Example 16 except that in Part A 3-methoxybenzyl chloride was employed in place of 4-methoxybenzyl chloride.

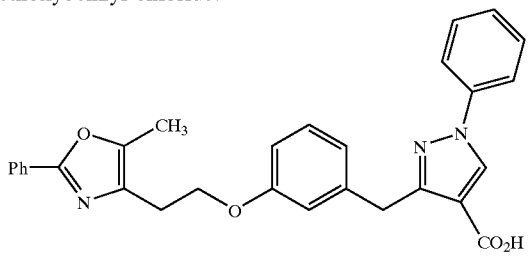

[M+H]⁺=480.2

EXAMPLE 18

A

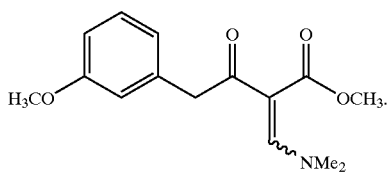

To a 0° C. solution of Meldrum's acid (4.33 g; 30 mmol) and pyridine (7.0 mL; 100 mmol) in CH₂Cl₂ (100 mL) was added dropwise 3-methoxyphenylacetyl chloride (5.0 g; 27 mmol) over 1 h. The resultant mixture. was stirred at RT for 2 h, then partitioned between aqueous 2N HCl and CH₂Cl₂. The organic layer was dried (Na₂SO₄) and concentrated in vacuo to give the crude adduct. This residue was dissolved in MeOH (20 mL) and the solution was heated at reflux for 3 h. The reaction mixture was cooled to RT, volatiles were removed in vacuo to give Part A compound (5.0 g; 83%) as a clear oil.

B

A solution of Part A compound (1.0 g; 4.5 mmol), dimethyl formamide dimethyl acetal (600 mg; 5.0 mmol) in CH₂Cl₂ (2.5 mL) was stirred at RT for 2 h. The reaction mixture was directly chromatographed (SiO₂; stepwise gradient from hexane:EtOAc 1:1 to EtOAc) to give Part B compound (400 mg; 32%) as an oil.

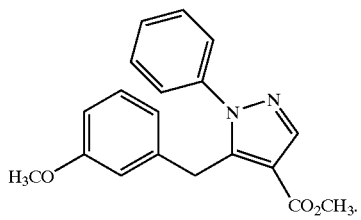
C

A solution of Part B compound (100 mg; 0.36 mmol), phenylhydrazine (40 mg 0.38 mmol) and activated 4A molecular sieves (500 mg) was heated at 100° C. for 10 h. At this point analytical LC-MS indicated that the reaction was complete. The reaction was cooled to RT, filtered, and the filtrate was concentrated in vacuo. The residue was chromatographed (SiO$_2$; hexane:EtOAc 4:1) to provide Part C compound (90 mg; 77%) as a clear oil.

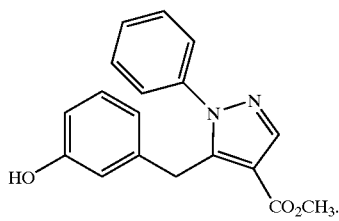
D

To a −78° C. solution of Part C compound (80 mg; 0.25 mmol) in CH$_2$Cl$_2$ (5 mL) was added BBr$_3$ (124 mg; 0.50 mmol) dropwise. The reaction mixture was stirred at −78° C. for 30 min, then allowed to warm to RT and stirred at RT for 2 h. Volatiles were removed in vacuo and the residue was partitioned between EtOAc and H$_2$O (5 mL each). The aqueous phase was extracted with EtOAc (2x). The combined organic extracts were dried (Na$_2$SO$_4$) and concentrated in vacuo to give an oil (the phenol-acid). This material was re-esterified by stirring in a saturated solution of HCl in MeOH (2 mL) for 2 h at RT. Volatiles were removed in vacuo and the residue was chromatographed (SiO$_2$; hexane:EtOAc 3:1) to provide Part D compound (50 mg; 62%) as a clear oil.

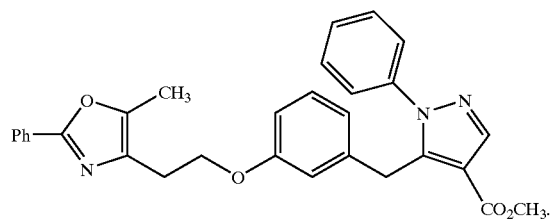
E

The same alkylation procedure was followed as in Example 1 using Part D compound (50 mg; 0.16 mmol in place of Example 1 Part F compound), the mesylate (68 mg; 0.24 mmol)

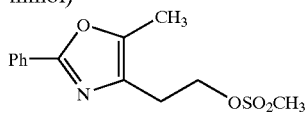

and K$_2$CO$_3$ (224 mg; 1.6 mmol) in MeCN (5 mL) to provide Product E (20 mg; 25%) as a crude product which was used in the next step without further purification.

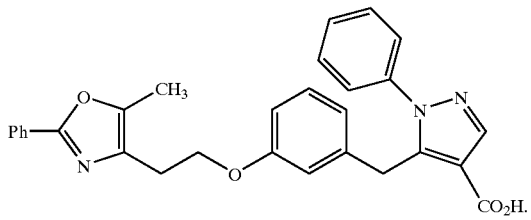
F

A solution of crude Product E in THF and aqueous LiOH (2 mL of a 1 M solution) was stirred at RT overnight. The reaction was acidified with excess 1 M aqueous HCl to pH~2; the aqueous layer was extracted with EtOAc (3x). The combined organic extracts were dried (Na$_2$SO$_4$) and concentrated in vacuo. The residue was purified by preparative HPLC (as described for the purification of Example 13 compound) to give the title compound (9 mg; 12%) as a white solid.

EXAMPLE 19

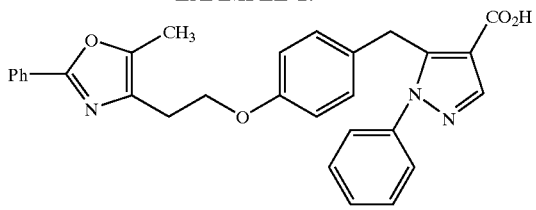

The method of Example 18 was used to synthesize the regioisomeric analog Example 19 except that 4-methoxyphenyl-acetyl chloride was used in place of 3-methoxyphenylacetyl chloride in Part A. [M+H]$^+$=480.2

EXAMPLE 20

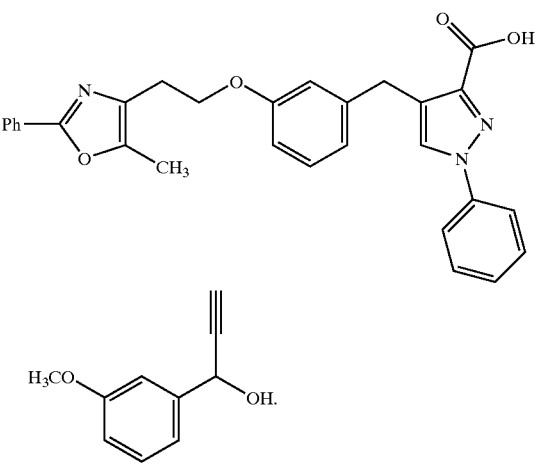
A

To a 0° C. solution of propargyl magnesium bromide in THF (50 mL of a 0.5 M solution; 25 mmol) under an atmosphere of N$_2$ was added dropwise a solution of 3-anisaldehyde (1.36 g; 10 mmol) in THF (10 mL). The reaction mixture was stirred at 0° C. for 3 h, then was allowed to warm to RT overnight, after which all starting material had been consumed (TLC). The reaction mixture was quenched by pouring cautiously into saturated aqueous NH₄Cl (30 mL) and ice (30 mL). The aqueous mixture was extracted with EtOAc (2×150 mL). The combined organic extracts were washed with H₂O (3×150 mL), dried (Na₂SO₄), and concentrated in vacuo to give Part A compound (1.2 g; 79%) as an oil. This material was used in the next step without further purification.

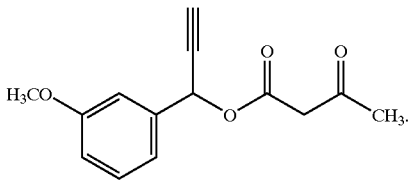

To a refluxing mixture of Part A compound (500 mg; 3.08 mmol), Et₃N (several drops) and CH₂Cl₂ (4 mL) was added a solution of diketene (ketene dimer; 336 mg; 4.0 mmol) in CH₂Cl₂ (1 mL) over 30 min. After addition was complete, heating under reflux was continued for another 3 h, after which the reaction mixture was cooled to RT. Volatiles were removed in vacuo, and the crude product was purified by vacuum distillation to give Part B compound (450 mg; 59%) as a colorless oil (b.p.=112° C. @ 0.05 mm Hg).

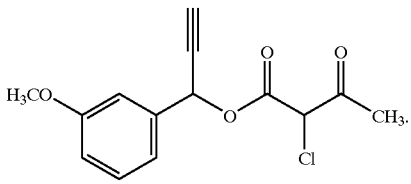

To a 0° C. solution of Part B compound (450 mg; 1.83 mmol) in anhydrous CH₂Cl₂ (3 mL) was added dropwise a solution of SO₂Cl₂ (161 μL; 2.0 mmol) in anhydrous CH₂Cl₂ (1 mL) over 2 h. Nitrogen was being continuously bubbled into the reaction mixture during this time. The reaction was allowed to warm to RT and stirred at RT for 2 h. Additional CH₂Cl₂ (10 mL) was added and the reaction was quenched by addition of excess saturated aqueous NaHCO₃. The organic phase was separated, washed with H₂O (2×), dried (Na₂SO₄) and concentrated in vacuo. The residue was chromatographed (SiO₂; hexane:EtOAc 5:1) to give Part C compound (380 mg; 68%) as a clear oil.

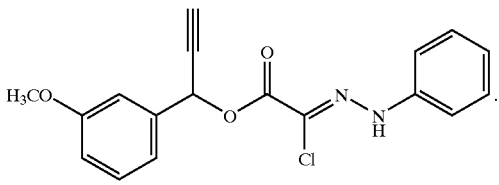

To a 0° C. solution of Part C compound (150 mg; 0.53 mmol) and sodium acetate (82 mg; 1.0 mmol) in 70% aqueous MeOH (15 mL) was added a 0° C. solution of benzenediazonium chloride (generated from 50 μL aniline and 69 mg of NaNO₂) slowly dropwise. The reaction was then allowed to warm slowly to RT and stirred at RT overnight. The reaction mixture was partitioned between EtOAc and H₂O (50 mL each). The organic phase was washed with H₂O (2×), dried (Na₂SO₄), and concentrated in vacuo. The residue was chromatographed (SiO₂; hexane:E-tOAc 3:1) to give Part D compound (192 mg; 94%) as a clear oil.

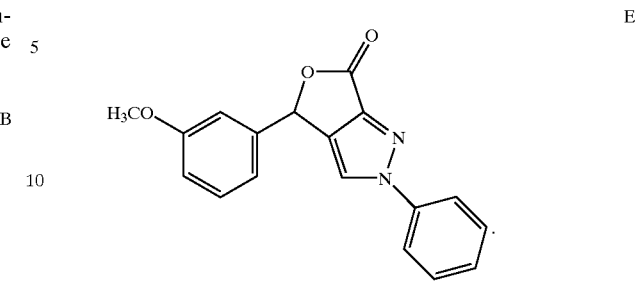

A solution of Part D compound (192 mg; 0.56 mmol) and Et₃N (1 mmol) in anhydrous toluene (20 mL) was heated under reflux until all starting material had been consumed (2 h; TLC). After cooling to RT, the mixture was washed with aqueous 1N HCl (30 mL) and H₂O (3×20 mL), dried (Na₂SO₄), and concentrated in vacuo. The resulting oil was chromatographed (SiO₂; hexane:EtOAc 3:1) to give Part E compound (120 mg; 69%) as an oil.

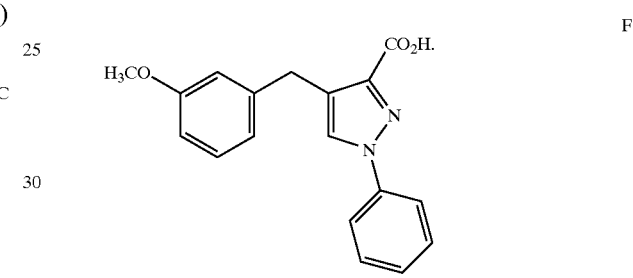

TMSCl (25 mg; 0.23 mmol) was added to a mixture of Part E compound (20 mg; 0.06 mmol) and sodium iodide (34 mg; 0.23 mmol) in anhydrous acetonitrile (5 mL). The reaction mixture was heated to reflux for 2 h under an N₂ atmosphere. After cooling to RT, water (2 mL) was added and the mixture was stirred at RT for 10 min. EtOAc (10 mL) was added and the organic phase was washed with aqueous 70% Na₂S₂O₃ (10 mL) and water, dried (Na₂SO₄) and concentrated in vacuo. The residue was purified by preparative HPLC (as described for Example 13 compound) to give Part F compound (15 mg; 81%) as a white solid.

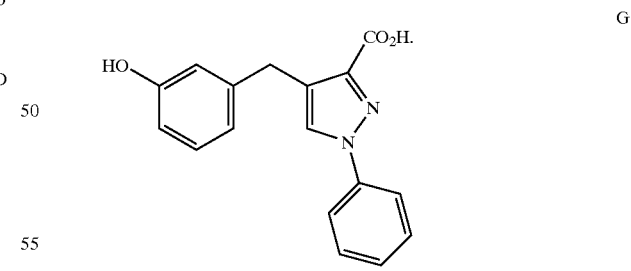

To a −78° C. solution of Part F compound (15 mg; 0.049 mmol) in CH₂Cl₂ (3 mL) was added dropwise neat BBr₃ (200 μL; 2.1 mmol). The reaction mixture was allowed to warm slowly to RT and stirred at RT for 1 h. The reaction was then cooled to −65° C. and MeOH (0.5 mL) was cautiously added. The solution was allowed to warm to RT and stirred at RT for 30 min. Volatiles were removed in vacuo and the residue was partitioned between EtOAc and water (10 mL each). The organic phase was dried (Na₂SO₄) and concentrated in vacuo to give Part G compound (15 mg; 99%) as an oil.

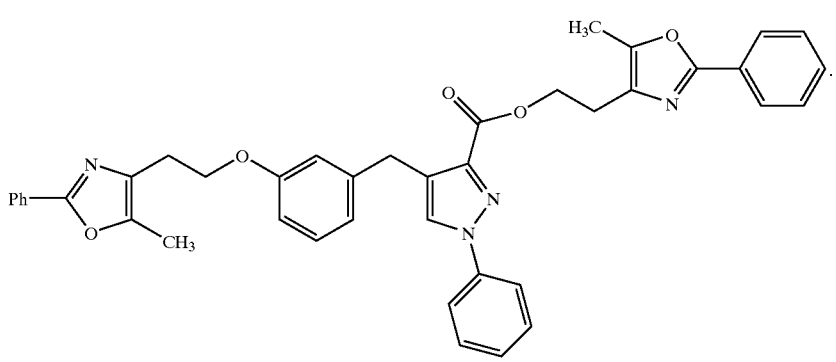

A mixture of Part G compound (15 mg; 0.051 mmol), K$_2$CO$_3$ (28 mg; 0.20 mmol) and the mesylate (34 mg; 0.12 mmol)

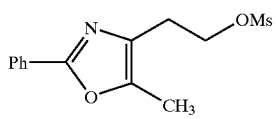

in MeCN (20 mL) was heated at 100° C. for 18 h. HPLC/MS at this point indicated that the reaction was complete at this point. The reaction was cooled to RT, then partitioned between EtOAc (150 mL) and H$_2$O (100 mL). The organic phase was washed with H$_2$O (2×100 mL), dried (Na$_2$SO$_4$), and concentrated in vacuo to give the crude product. This material was chromatographed (SiO$_2$; 3:1 hexane:EtOAc) to give Part H compound (20 mg; 59%) as an oil.

I

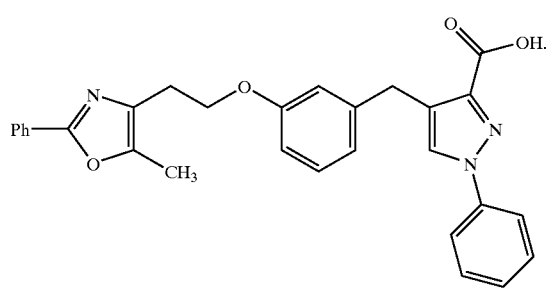

A solution of Part G compound (20 mg; 0.03 mmol) in aqueous LiOH (1.0 mL of a 1.0 M solution) and THF (5 mL) was stirred at 50° C. for 4 h. HPLC/MS at this point showed that the reaction was complete. The reaction was partitioned between EtOAc (10 mL) and aqueous HCl (10 mL of a 1N solution). The organic phase was washed with H$_2$O (3×20 mL), then was concentrated in vacuo. The residue was purified by preparative HPLC (as described for the purification of BMS-460193) to give the title compound (12 mg; 83%) as a solid. [M+H]+=480.5

EXAMPLE 21

A

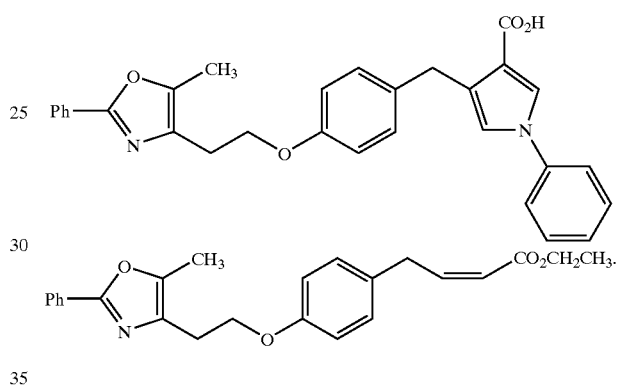

A solution of the Example 11 Part C acetylenic ester (100 mg; 0.26 mmol)

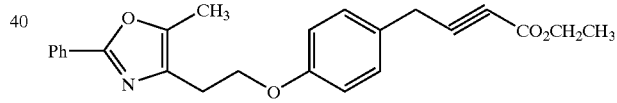

and quinoline (2 μL; 0.014 mmol) in the presence of Lindlar's catalyst (10% Pd/C) in toluene (5 mL) was stirred under an atmosphere of H$_2$ (balloon) for 1.5 h. HPLC/MS at this point showed that reaction was complete. The catalyst was removed by filtration through Celite® and the filtrate was concentrated in vacuo to give the crude α,β unsaturated ester as an oil. This material was chromatographed (SiO$_2$; hex:EtOAc 3:1) to give Part A compound (50 mg; 49%) as an oil.

B

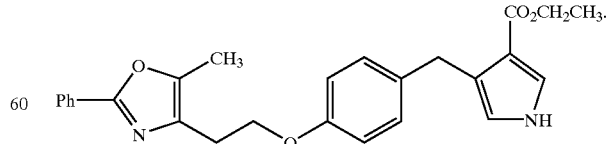

A solution of Part A compound (430 mg; 1.09 mmol) and tosylmethyl isocyanide (216 mg; 1.09 mmol) in DMSO (3 mL) was added dropwise to a 0° C. suspension of NaH (65 mg of a 60% suspension in oil) in Et$_2$O (2 mL). The reaction was then allowed to warm to RT and stirred at RT for 15 min, at which point the reaction was complete by analytical HPLC. The reaction mixture was partitioned between EtOAc and saturated aqueous $NH_4Cl$. The aqueous phase was extracted with EtOAc (2×). The combined organic extracts were dried ($Na_2SO_4$) and concentrated in vacuo. The crude product was chromatographed ($SiO_2$; hex:EtOAc 3:1) to give Part B compound (300 mg; 69%) as an oil.

C

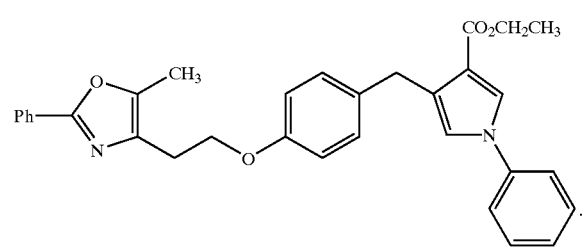

A mixture of Part B compound (20 mg; 0.047 mmol), phenylboronic acid (7 mg; 0.057 mmol), Cu(OAc)$_2$ (5 mg; 0.028 mmol) and 4A molecular sieves (200 mg) in Et$_3$N:pyridine:CH$_2$Cl$_2$ (2 mL of a 1:1:2 mixture) was heated in a sealed tube at 70° C. for 3 days. Analytical HPLC showed that the reaction was 60% complete. The reaction was cooled to RT and partitioned between EtOAc and 1 M aqueous HCl. The aqueous phase was extracted with EtOAc (2×); the combined organic extracts were dried (Na$_2$SO$_4$) and concentrated in vacuo to give Part C compound as an oil, which was used in the next step without further purification.

D

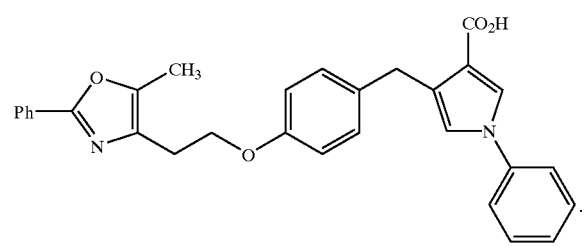

A solution of crude Part C compound and aqueous LiOH (2 mL of a 1M solution) in THF:H$_2$O was stirred at 100° C. for 24 h. The reaction was cooled to RT, then acidified to pH 2 with aqueous 1 M HCl. The aqueous phase was extracted with EtOAc (2×); the combined organic extracts were dried (Na$_2$SO$_4$) and concentrated in vacuo to give the crude product. This material was purified by preparative HPLC (as described for the purification of Example 13 compound) to give the title compound (8 gm; 35%) as a white solid. [M+H]$^+$=479.2

EXAMPLE 22

A

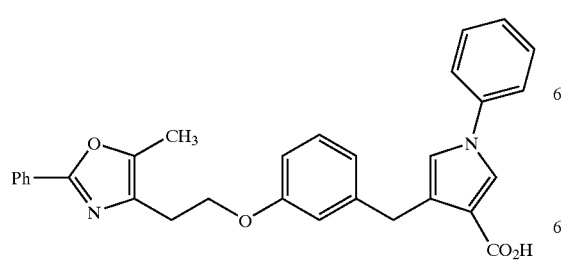

-continued

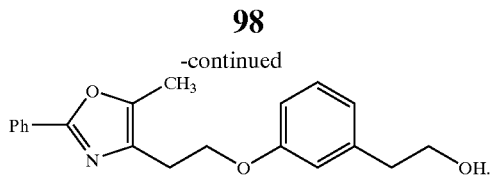

A mixture of 3-hydroxy phenylethanol (500 mg; 3.61 mmol), the mesylate (990 mg; 3.52 mmol)

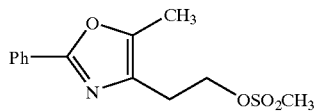

and K$_2$CO$_3$ (2.0 g; 14 mmol) in MeCN (5 mL) was stirred at 90° C. for 5 h. At this point LC/MS showed that the reaction was complete. The reaction was cooled to RT, solids were filtered off, and the filtrate was diluted with EtOAc (100 mL). The solution was successively washed with aqueous 1 M HCl (10 mL), 1 M NaOH (10 mL) and H$_2$O (50 mL), dried (Na$_2$SO$_4$) and concentrated in vacuo. The residue was chromatographed (SiO$_2$; 2:1 hex:EtOAc) to give Part A compound (1.0 g; 87%) as an oil.

B

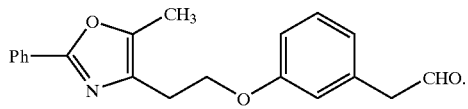

To a solution of Part A compound (1.0 g; 3.10 mmol) in CH$_2$Cl$_2$ (20 mL) was added Dess-Martin periodinane (3.0 g; 7.1 mmol) and the mixture was stirred at RT for 3 h. Volatiles were removed in vacuo and the residue was partitioned between EtOAc (25 mL) and H$_2$O (25 mL). The organic phase was dried (Na$_2$SO$_4$) and concentrated in vacuo. The residue was chromatographed (SiO$_2$; hex:EtOAc 3:1) to give Part B compound (227 mg; 23%) as an oil.

C

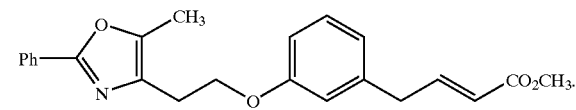

A mixture of Part B compound (86 mg; 0.27 mmol) and methyl (triphenylphosphoranylidene) acetate (110 mg; 0.33 mmol) in toluene (2 mL) was heated at 100° C. for 2 h. Analytical HPLC showed that the reaction was complete. Volatiles were removed in vacuo and the residue was chromatographed (SiO$_2$; hex:EtOAc 3:1) to give Part C compound (110 mg; 98%) as an oil.

D

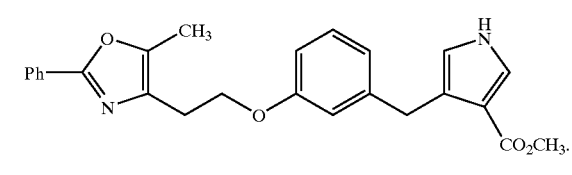

A solution of Part C compound (101 mg; 0.27 mmol) and tosylmethyl isocyanide (TosMIC; 53 mg; 0.27 mmol) in DMSO (1 mL) was added dropwise to a 0° C. suspension of NaH (15 mg of a 60% suspension in oil) in Et$_2$O (1 mL). The reaction was then allowed to warm to RT and stirred at RT for 15 min, at which point the reaction was complete by analytical HPLC. The reaction mixture was partitioned between EtOAc and saturated aqueous NH$_4$Cl. The aqueous phase was extracted with EtOAc (2×). The combined organic extracts were dried (Na$_2$SO$_4$) and concentrated in vacuo. The crude product was chromatographed (SiO$_2$; hex:EtOAc 3:1) to give Part D compound (20 mg; 18%) as an oil.

E

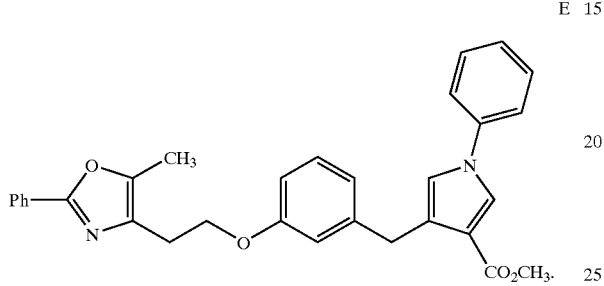

A mixture of Part D compound (20 mg; 0.048 mmol), phenylboronic acid (7 mg; 0.057 mmol), Cu(OAc)$_2$ (5 mg; 0.028 mmol) and 4A molecular sieves (200 mg) in Et$_3$N: pyridine:CH$_2$Cl$_2$ (2 mL of a 1:1:2 mixture) was heated in a sealed tube at 70° C. for 3 days. Analytical HPLC showed that the reaction was 60% complete. The reaction was cooled to RT and partitioned between EtOAc and 1 M aqueous HCl. The aqueous phase was extracted with EtOAc (2×); the combined organic extracts were dried (Na$_2$SO$_4$) and concentrated in vacuo to give Part E compound as an oil, which was used in the next step without further purification.

F

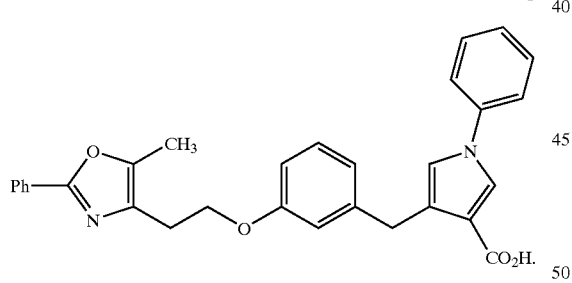

A solution of crude Part E compound and aqueous LiOH (2 mL of a 1M solution) in THF:H$_2$O was stirred at 100° C. for 24 h. The reaction was cooled to RT, then acidified to pH~2 with aqueous 1 M HCl. The aqueous phase was extracted with EtOAc (2×); the combined organic extracts were dried (Na$_2$SO$_4$) and concentrated in vacuo to give the crude product. This material was purified by preparative HPLC (conditions used as described for the purification of Example 13 compound) to give the title compound (7 gm; 30% over 2 steps) as a white solid. [M+H]$^+$=479.2

EXAMPLES 23 TO 50

The following N-aryl pyrrole acids were synthesized according to one of the above methods:

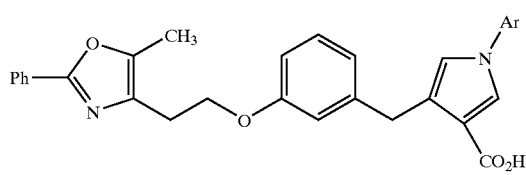

| Example No. | Ar | [M + H]$^+$ |
|---|---|---|
| 23 | H | 403.3 |
| 24 | 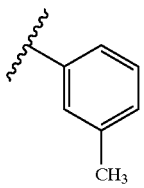 | 493.0 |
| 25 | 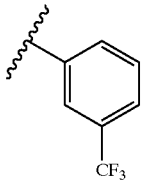 | 547.0 |
| 26 | 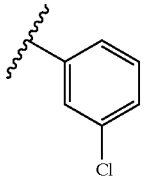 | 514.0 |
| 27 | 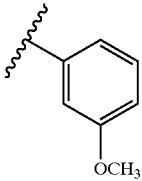 | 509.0 |
| 28 | 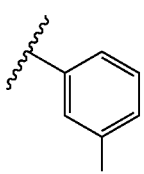 | 497.0 |
| 29 | 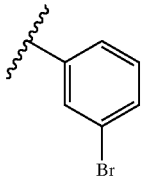 | 556.9 & 558.9 |

-continued

Structure for Examples 30-36: 2-phenyl-5-methyl-oxazole-4-yl-ethoxy group on meta-substituted benzene, linked via CH2 to pyrrole bearing N-Ar and CO2H.

| Example No. | Ar | [M + H]+ |
|---|---|---|
| 30 | 3-thienyl | 485.0 |
| 31 | 4-fluorophenyl | 497.0 |
| 32 | 4-chlorophenyl | 514.0 |
| 33 | 4-bromophenyl | 557.0 & 559.1 |
| 34 | 4-methylphenyl | 493.3 |
| 35 | 4-methoxyphenyl | 509.3 |
| 36 | 4-(trifluoromethyl)phenyl | 547.3 |

Structure for Examples 37-44: 2-phenyl-5-methyl-oxazole-4-yl-ethoxy group on para-substituted benzene, linked via CH2 to pyrrole bearing CO2H and N-Ar.

| Example No. | Ar | [M + H] |
|---|---|---|
| 37 | H | 403.2 |
| 38 | 3-methylphenyl | 493.1 |
| 39 | 3-(trifluoromethyl)phenyl | 547.1 |
| 40 | 3-chlorophenyl | 513.0 |
| 41 | 3-methoxyphenyl | 509.1 |
| 42 | 3-fluorophenyl | 497.1 |
| 43 | 3-bromophenyl | 557.0 & 559.0 |
| 44 | 3-thienyl | 485.0 |

-continued

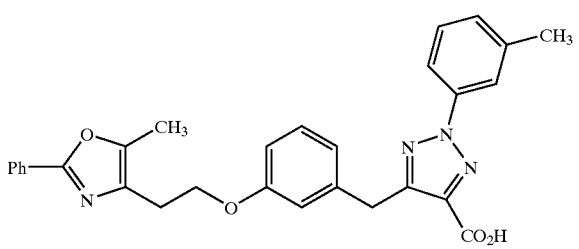

| Example No. | Ar | [M + H] |
|---|---|---|
| 45 | 4-F-C6H4- | 597.1 |
| 46 | 4-Cl-C6H4- | 513.0 |
| 47 | 4-Br-C6H4- | 557.2 and 559.1 |
| 48 | 4-CH3-C6H4- | 493.3 |
| 49 | 4-OCH3-C6H4- | 509.3 |
| 50 | 4-CF3-C6H4- | 547.3 |

EXAMPLE 51

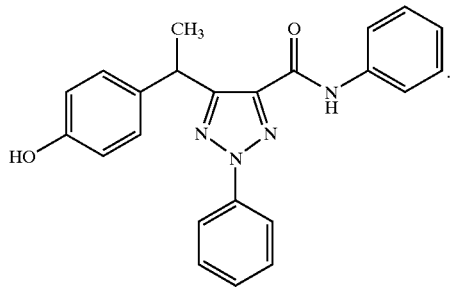

The identical synthetic sequence described in Example 1 was used (except that 3-methylphenylhydrazine replaced phenylhydrazine) to prepare the title compound (1.2 mg; 24% overall yield for last 3 steps). [M+H]⁺=495.1

EXAMPLE 52

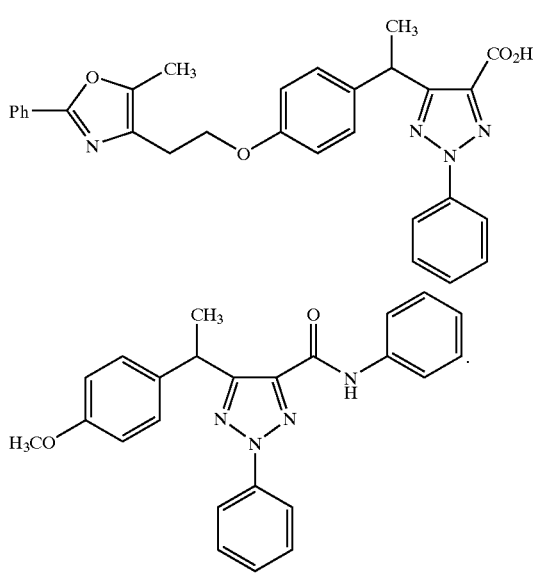

A

To a −74° C. solution of Example 3 Part E compound (50 mg; 0.13 mmol) in anhydrous THF (2 mL) was added lithium diisopropylamide(LDA) (200 μL of a 2 M solution in heptane/THF). The blue reaction solution was stirred at −74° C. for 1 h, then was warmed to RT and stirred at RT for 1 h, then cooled to −78° C. A solution of iodomethane (85 mg; 0.6 mmol) in THF (0.5 mL) was added dropwise and the reaction was stirred at −78° C. for 2 h, then was allowed to warm to RT. The reaction was partitioned between saturated aqueous $NH_4Cl$ (0.5 mL), $H_2O$ and EtOAc (5 mL each). The organic phase was dried ($Na_2SO_4$) and concentrated in vacuo; the residue was chromatographed ($SiO_2$; continuous gradient from 100% hex to 3:7 hex:EtOAc) to give Part A compound (20 mg; 38%) as white crystals.

B

To a RT solution of Part A compound (20 mg; 0.05 mmol) in $CH_2Cl_2$ (2.0 mL) was added dropwise $BBr_3$ (0.2 mL of a 1 M solution in $CH_2Cl_2$). The mixture was stirred at RT for 30 min, then concentrated in vacuo. The residue was stripped from MeOH (1 mL) and chromatographed ($SiO_2$; 3:1 hex:EtOAc) to give Part B compound (13 mg; 68%) as white crystals.

C

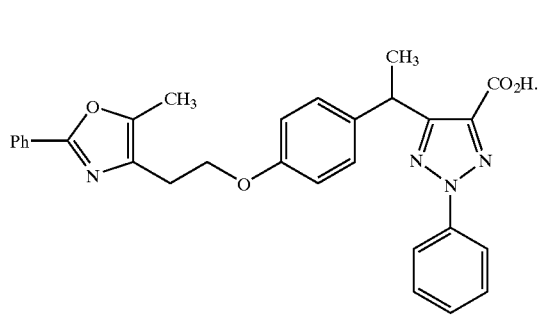

A mixture of Part B compound (13 mg; 0.032 mmol), 5-methyl 2-phenyl oxazole 4-ethanol mesylate (15 mg; 0.053 mmol; prepared as described in Example 11) and $K_2CO_3$ (500 mg; 3.6 mmol) in MeCN (2 mL) was heated at reflux in a sealed tube for 18 h, then cooled to RT and filtered. The filtrate was concentrated in vacuo; the residue was dissolved in EtOH (2 mL) and KOH (200 mg; 3.6 mmol) was added. The mixture was stirred at 80° C. in a sealed tube, then cooled to RT and partitioned between EtOAc (20 mL) and aqueous 1 N HCl (5 mL). The organic phase was washed with $H_2O$ (2×10 mL) and concentrated in vacuo. The residue was purified by preparative HPLC (YMC reverse-phase ODS 20×100 mm column; flow rate=20 mL/min; 10 min continuous gradient from 25:75 B:A to 100% B+5 min hold-time at 100% B, where solvent A=90:10:0.1 $H_2O$:MeOH:TFA and solvent B=90:10:0.1 MeOH:$H_2O$:TFA) to give the title compound (14.8 mg; 88%) as a white solid. $[M+H]^+=495.3$

EXAMPLE 53

A

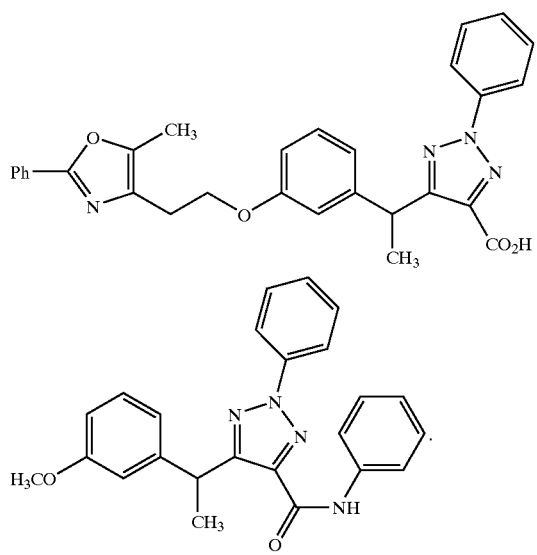

The procedure described for the synthesis of Example 52 Part A compound was used (except that Example 1 Part E compound [50 mg; 0.13 mmol] was used in place of Example 3 Part E compound) to prepare Part A compound (35 mg; 68%) as an oil.

B

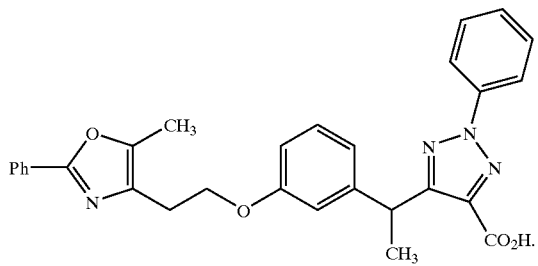

The synthetic sequence described for the synthesis of Example 52 (except that Part A compound was used instead of Example 52 Part A compound) was used to prepare the title compound (24 mg; 55% overall for 3 steps) as a solid. $[M+H]^+=495.3$

EXAMPLE 54

A

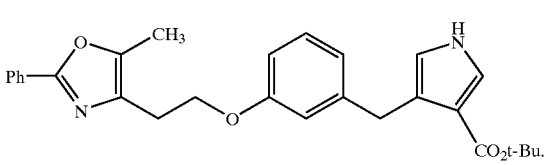

A solution of Example 22 Part B compound (150 mg; 0.47 mmol) and tert-butyl (triphenylphosphoranylidene)-acetate (200 mg; 0.53 mmol) in toluene (10 mL) was stirred at 90° C. for 1 h. After cooling, volatiles were removed in vacuo and the residue was chromatographed ($SiO_2$; 3:1 hex:EtOAc) to give Part A compound (200 mg; 99%) as an oil.

B

A solution of Part A compound (200 mg; 0.477 mmol) and tosylmethyl isocyanide (100 mg; 0.512 mmol) in DMSO was added dropwise into a slurry of NaH (26 mg of a 60% mixture in oil; 0.65 mmol) in $Et_2O$ over 30 min at RT. The reaction was stirred at RT for 30 min, then was partitioned between $H_2O$ and EtOAc. The organic phase was dried ($Na_2SO_4$) and concentrated in vacuo. The residue was chromatographed ($SiO_2$; hex:EtOAc 3:1) to give Part B compound (60 mg; 27%) as an oil.

A mixture of Part B compound (23 mg; 0.05 mmol), K$_2$CO$_3$ (200 mg; 1.45 mmol) and methyl iodide (10 mg; 0.07 mmol) in DMF (2 mL) was stirred at 80° C. for 2 h in a sealed tube. The reaction was cooled to RT and partitioned between H$_2$O and EtOAc (10 mL each). The organic phase was washed with H$_2$O (2×10 mL), dried (Na$_2$SO$_4$) and concentrated in vacuo. A solution of the crude N-methylpyrrole ester in TFA/CH$_2$Cl$_2$ (2 mL of a 1:1 solution) was stirred at RT for 30 min, then was concentrated in vacuo. The residue was purified by preparative HPLC (according to the conditions for Example 52 compound, except that a continuous gradient of 70:30 A:B to 100% B was used rather than 75:25 A:B to 100% B) to furnish the title compound (7.2 mg; 34%) as a white solid.

Part A compound was prepared as described for the synthesis of Example 22 Part B compound from the mesylate and 4-hydroxyphenylethanol (which was used instead of 3-hydroxyphenylethanol).

Part A compound (150 mg; 0.47 mmol) was used to prepare (as described for the synthesis of Example 54 Part A compound) Part B compound (200 mg; 99%) as an oil.

Part B compound (200 mg; 0.477 mmol) was used to prepare (as described for the synthesis of Example 54 Part B compound) Part C compound (100 mg; 46%) as an oil.

Part C compound (23 mg; 0.05 mmol) was used to prepare (as described for the synthesis of Example 54) the title compound (7.7 mg; 37%) as a white solid. [M+H]$^+$=417.2

EXAMPLE 56

A mixture of Example 54 Part B compound (20 mg; 0.044 mmol), 2-bromothiophene (8 mg; 0.05 mmol), CuI (30 mg; 0.157 mmol), ZnO (10 mg; 0.122 mmol) and K$_2$CO$_3$ (50 mg; 0.36 mmol) in 1-methyl-2-pyrrolidinone (NMP; 2 mL) was heated in a sealed tube at 166° C. for 18 h. The reaction was cooled to RT and partitioned between EtOAc and aqueous HCl (10 mL of a 1 M solution). The organic phase was washed with brine (2×10 mL), dried (Na$_2$SO$_4$) and concentrated in vacuo. The residue was chromatographed (SiO$_2$; 1:1 hexane:EtOAc) to give Part A compound as a solid.

B

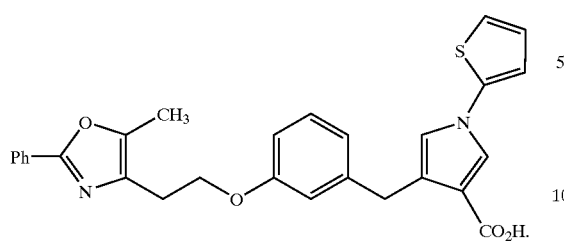

A solution of Part A compound in TFA/CH₂Cl₂ (1 mL of a 1:1 solution) was stirred at RT for 1 h, then was concentrated in vacuo. The residue was purified by preparative HPLC (according to the conditions described for Example 54 compound) to furnish the title compound (7 mg; 32% for 2 steps) as a white solid. [M+H]⁺=485.2

EXAMPLE 57

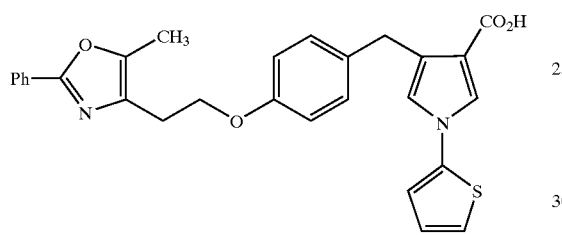

Example 55 Part C compound (20 mg; 0.044 mmol; using the same synthetic sequence as described for Example 56) was used to prepare the title compound (5 mg; 23%) as a solid.

A

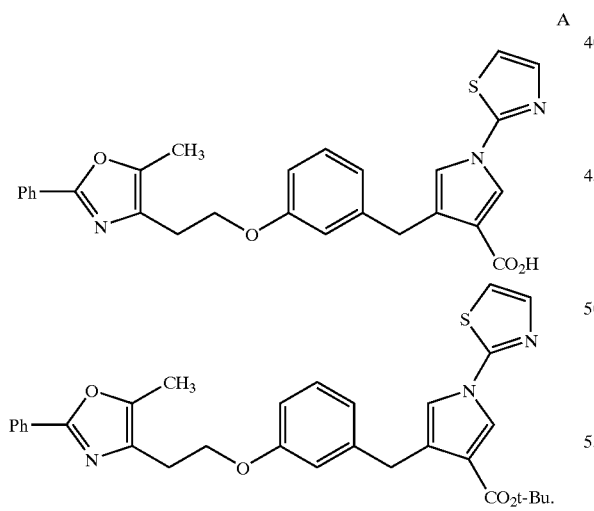

A mixture of Example 54 Part B compound (20 mg; 0.044 mmol), 2-bromothiazole (10 mg; 0.061 mmol), CuI (30 mg; 0.157 mmol), ZnO (10 mg; 0.122 mmol) and K₂CO₃ (50 mg; 0.36 mmol) in 1-methyl-2-pyrrolidinone (2 mL) was heated in a sealed tube at 166° C. for 18 h. The reaction was cooled to RT and partitioned between EtOAc and aqueous HCl (10 mL of a 1 M solution). The organic phase was washed with brine (2×10 mL), dried (Na₂SO₄) and concentrated in vacuo. The residue was chromatographed (SiO₂; 1:1 hexane:EtOAc) to give Part A compound as a solid.

B

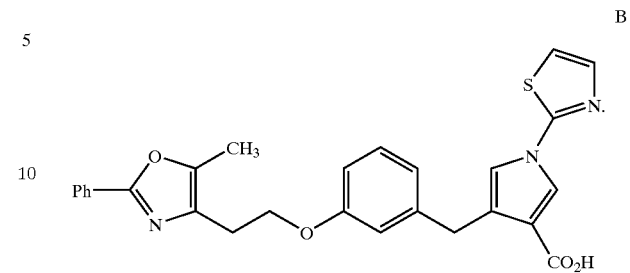

A solution of Part A compound in TFA/CH₂Cl₂ (1 mL of a 1:1 solution) was stirred at RT for 1 h, then was concentrated in vacuo. The residue was purified by preparative HPLC (according to the conditions described for Example 54) to furnish the title compound (9 mg; 42% for 2 steps) as a brown solid. [M+H]+=486.3

EXAMPLE 59

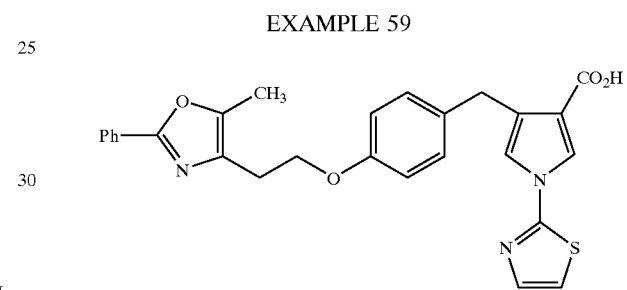

Example 55 Part C compound (20 mg; 0.044 mmol; using the same synthetic sequence as described for Example 56) was used to prepare the title compound (5 mg; 23%) as a brown solid. [M+H]+=486.3

EXAMPLE 60

A

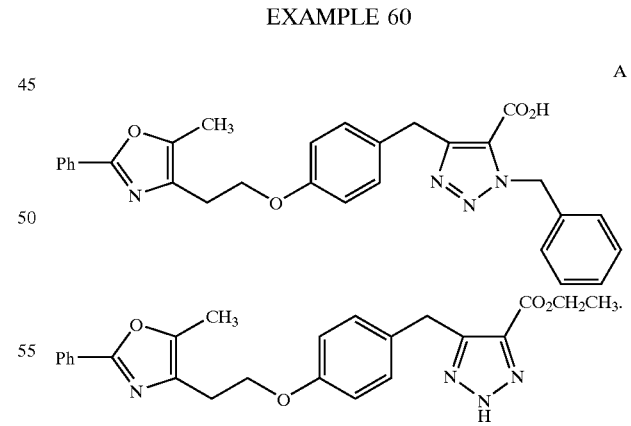

A solution of Example 11 Part C compound (176 mg; 0.45 mmol) and sodium azide (32 mg; 0.49 mmol) in anhydrous DMF (1 mL) was stirred at RT under an atmosphere of N₂ for 15 min, after which H₂O (10 mL) was added. The solids were filtered off and dried in vacuo, then chromatographed (SiO₂; 3:1 hex:EtOAc) to give Part A compound (138 mg; 71%) as a yellow solid.

111

B

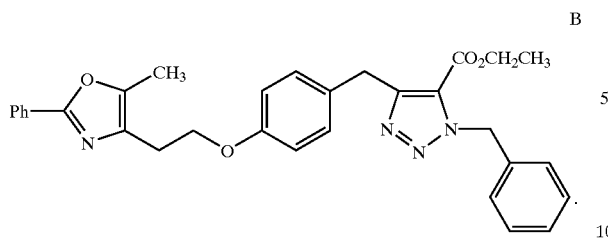

A solution of Part A compound (138 mg; 0.319 mmol), benzyl bromide (118 mg; 0.69 mmol) and $K_2CO_3$ (238 mg; 2.05 mmol) in DMF (1 mL) was stirred at RT for 18 h. The reaction was partitioned between $H_2O$ and EtOAc (5 mL each); the organic phase was dried ($Na_2SO_4$) and concentrated in vacuo. The residue was chromatographed ($SiO_2$; hex:EtOAc 3:1) to give Part B compound (25 mg; 15%) as an oil. In addition, the other two regioisomers were also obtained: Part C compound (40 mg; 23%)

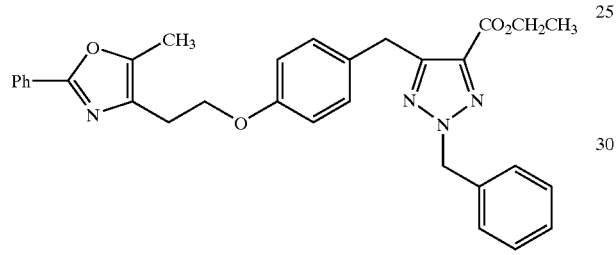

and Part D compound (12 mg; 7%)

E

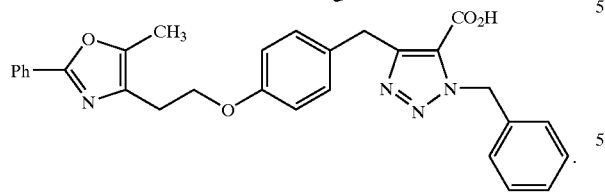

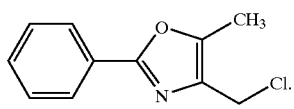

A solution of Part B compound in THF (2 mL) and aqueous LiOH (1 ML of a 1 M solution) was stirred at RT for 18 h, then partitioned between aqueous HCl (2 mL of a 1 M solution) and EtOAc (5 mL). The organic phase was washed with $H_2O$ (2×5 mL), dried ($Na_2SO_4$) and concentrated in vacuo to give the title compound (19 mg; 80%) as a white solid. [M+H]⁺=495.2

112

EXAMPLE 61

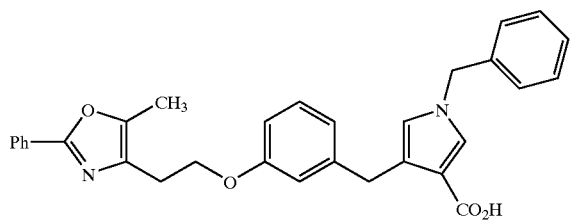

Example 54 Part B compound was used to prepare (as described for the synthesis of Example 54, but using benzyl bromide instead of methyl iodide) the title compound (7 mg) as a yellow solid after preparative HPLC purification (as for Example 54). [M+H]+=493.1

EXAMPLE 62

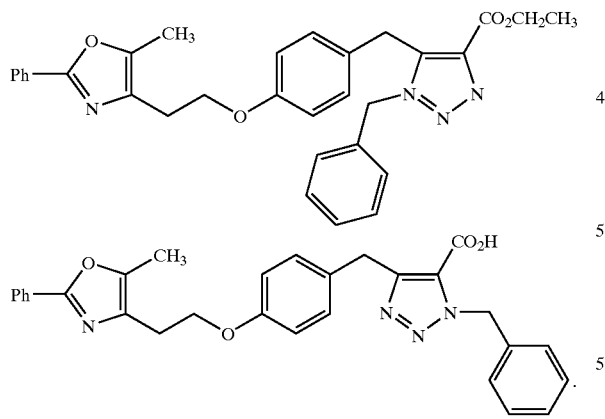

A

To a solution of benzaldehyde (23.8 g, 234 mmol) in EtOAc (150 mL; pre-saturated with HCl gas) was added 2,3-butanedione mono-oxime (25.0 g, 234 mmol) in one portion and the resulting solution was stirred at RT for 12 h. Analytical HPLC indicated that all starting materials had been consumed. The reaction mixture was concentrated in vacuo to yield Part A compound as a white solid, which was used in the next step without further purification.

B

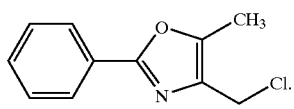

To a solution of Part A compound in $CHCl_3$ (200 mL) was added dropwise $POCl_3$ (30 mL, 320 mmol). The reaction was stirred for 12 h at 50° C., then was concentrated in vacuo. The brown residue was partitioned between EtOAc (300 mL) and 1N aqeuous NaOH. The organic phase was washed with brine, dried, ($MgSO_4$) and concentrated in vacuo. The residue was chromatographed ($SiO_2$; $Et_2O$) to give Part B compound (41.5 g; 86%) as a light brown solid (>95% pure by analytical HPLC and ¹H-NMR analysis).

C

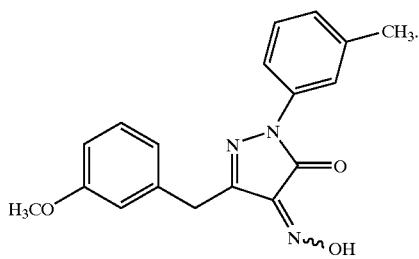

A mixture of Example 1 Part C compound (592 mg; 1.9 mmol) and 3-methylphenylhydrazine (330 mg; 2.08 mmol) in EtOH (30 mL) and anhydrous $MgSO_4$ (1 g) was heated to reflux overnight. The reaction was filtered, and the filtrate was concentrated in vacuo. The residue was chromatographed ($SiO_2$; continuous gradient from 100% hex to 100% EtOAc) to give Part C compound (478 mg; 76%) as a mixture of S-cis and S-trans oximes.

D

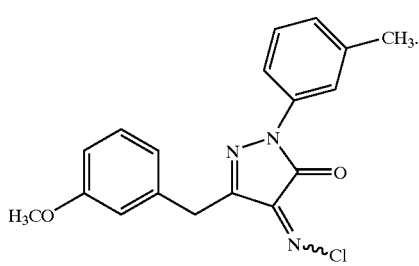

To a RT solution of Part C compound (103 mg; 0.31 mmol) in toluene (5 mL) was added $PCl_5$ (70 mg; 0.34 mmol) and the reaction was stirred at RT for 2 h, then concentrated in vacuo. The residue was partitioned between EtOAc and $H_2O$; the organic phase was washed with brine, dried ($Na_2SO_4$), and concentrated in vacuo to give crude Part D compound, which was used in the next step without further purification.

E

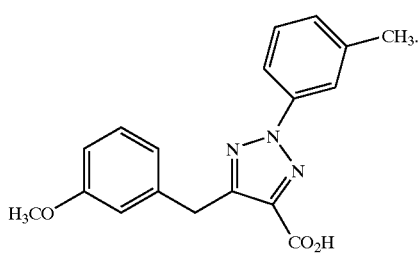

To a RT solution of crude Part D compound in absolute EtOH (3 mL) was added dropwise aqueous NaOH (0.25 mL of a 2 M solution). The mixture turned from orange to dark brown and was stirred at RT for 1 h, then was partitioned between excess aqueous 1 N HCl and EtOAc. The aqueous phase was extracted with EtOAc, and the combined organic extracts were washed with brine, dried ($Na_2SO_4$) and concentrated in vacuo. The residue was purified by preparative HPLC (as described for Example 5) to give Part E compound (10.5 mg; 11% for 2 steps) as a brown solid.

F

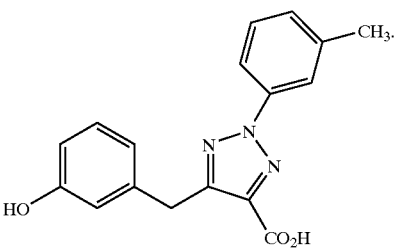

To a −78° C. solution of Part E compound (11 mg; 0.033 mmol) was added $BBr_3$ (0.02 mL; 0.21 mmol) dropwise. The reaction was stirred at −78° C. for 15 min, then was warmed to RT and stirred at RT for 5 h. After cooling to 0° C., the reaction was cautiously quenched with a large excess of saturated aqueous $NH_4Cl$. The aqueous phase was extracted with EtOAc; the combined organic extracts were washed with brine, dried ($Na_2SO_4$) and concentrated in vacuo to give crude Part F compound, which was used in the next step without further purification.

G

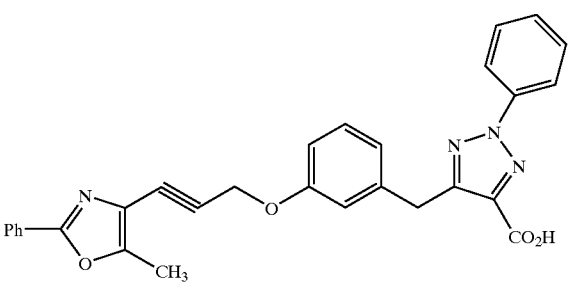

A mixture of Part F compound (10 mg; 0.033 mmol), $K_2CO_3$ (15 mg; 0.11 mmol) and Part B compound (20 mg; 0.096 mmol) in MeCN (2 mL) was heated at 90° C. overnight, then cooled to RT and partitioned between $H_2O$ and EtOAc. The aqueous phase was extracted with EtOAc; the combined organic extracts were washed with brine, dried ($Na_2SO_4$), and concentrated in vacuo. The residue was chromatographed ($SiO_2$; continuous gradient from 100% hexane to 100% EtOAc) and then further purified by preparative HPLC (conditions as for purification of Example 52, except that a continuous gradient from 30:70 A:B to 100% B was used) to provide the title compound (5.2 mg; 26% for 2 steps) as a colorless oil. [M+H]+=481.1

Following the procedures set out in the above Examples and in the reaction schemes, the following exemplary compounds may be prepared:

-continued

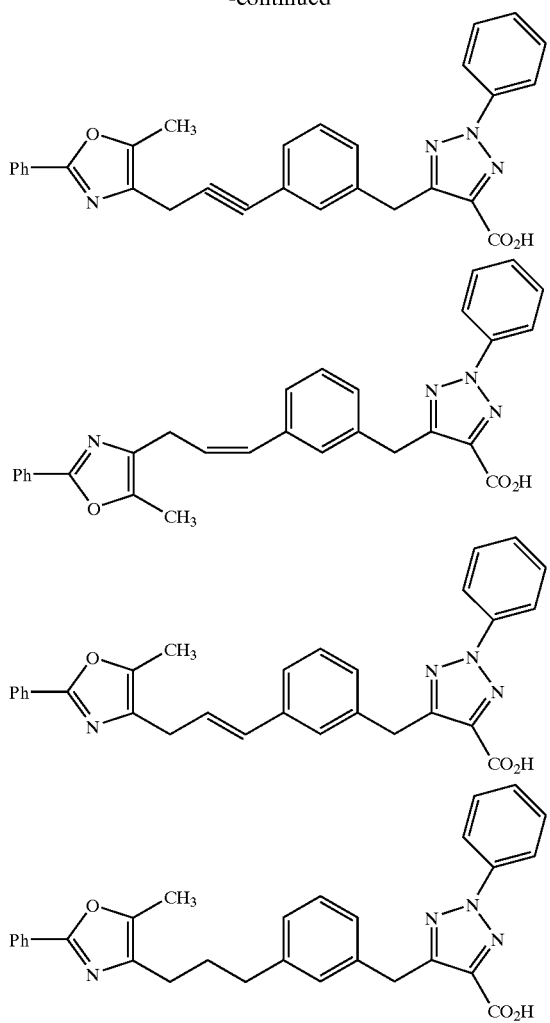

EXAMPLE 63

In vitro Screening Assays for Dual PPARγ Antagonist/PPARα Agonist

A. Screen for PPARγ Antagonist in Mouse 3T3-L1 Pre-adipocyte Cells

Compounds which show potent binding to PPARγ were assayed for their ability to inhibit 50 nM rosiglitazone (an authentic PPARγ agonist) induced differentiation of mouse 3T3-L1 pre-adipocytes to mature adipocytes. 5×10⁵ 3T3-L1 cells per plate were added to 96 well plates and cultured in DMEM-high glucose and 10% FBS medium for two days, before induction. Cells were induced for 48 hr with 1 μm dexamethasone, 5 μg/ml insulin, and 0.6 μm isobutylmethylxanthine (IBMX) in the same medium. At this time, test compounds in a serial dilution were added into 50 nM rosiglitazone and 0.1% DMSO containing medium in each well. Cells were re-fed with the same concentration of testing compound, rosiglitazone (a PPARγ agonist) and DMSO containing medium (without insulin, dexamethasone and IBMX) for an additional 72 hr. After a total of 5 days incubation, 4 μl of media from each well were collected and diluted into 40 μl of H$_2$O in 96 well ELISA plate, 300 μl of Triglycerides Blank Reagent (Bayer Diagnostics) was added into each well and incubated for 5 min at room temperature. The % inhibition of each compound to rosiglitazone induced free glycerol release from the cell was determined using Spectremax 250 ELISA reader at wavelength 500 nM. Data were normalized to DMSO only control and % maximum inhibition of transactivation was calculated relative to 50 nM rosiglitazone positive control. The ED$_{50}$ values were calculated using standard equations for mid-point of the activity inhibition curves.

B. Screen for PPARγ Antagonist in CV-1 Primate Kidney Cells

Compounds which show potent binding to PPARγ were assayed for their ability to inhibit 1 μM rosiglitazone (an authentic PPARγ agonist) induced transactivation of SEAP reporter gene activity in CV-1 cells. CV-1 cells (these cell express endogenous PPARγ gene) were transfected with a 3×PPRE-SEAP reporter gene DNA construct and stable colonies were selected, expanded and tested for responsiveness to compounds using standard protocols. SEAP reporter gene constructs were made by inserting 3 repeats of the rat fatty acid binding protein PPRE including the 7 nucleotides immediately 5' to the SV40 early minimal promoter of pSEAP2 (Clontech). 1.2×10⁶ CV-1/PPRE-SEAP cells were plated in a 96 well plate one day before compound addition. Dilution series of test compounds were made in DMEM 10% FBS, 0.5% (v/v final) DMSO and 1 uM rosiglitazone (a PPARγ agonist). 150 μl aliquots of each concentration were delivered to two non-adjacent wells. Also included on each plate were 6 wells of 1 μM rosiglitazone (a PPARγ agonist) in 0.5% DMSO media. Media was collected in fresh 96 well plates 40 hrs following incubation with compounds and assayed for SEAP activity. SEAP is resistant to heat, so the endogenous phosphatases in the collected media were inactivated by sealing the plates with pressure sensitive adhesive sealing film (Corning), and heating at 65° C. for 30' to 1 hour. After allowing to come to room temperature (RT), 25 μl of aliquots of heat inactivated media were added to clear bottom 96 well black plates, 100 μl of the fluorescent substrate Attophos reagent (Promega) was added per well. The plate was incubated for 5' in the dark, and then the fluorescence measured in a CytoFluor series 4000 plate reader (Perseptive Biosystems): excitation filter, 450/50 nm; emission filter, 580/50 nm; 8 cycles, 1 minute/cycle, 3 reads/well/cycle. Data were normalized to DMSO only control and % maximum inhibition of transactivation was calculated relative to 1 μM rosiglitazone positive control. The ED$_{50}$ values were calculated using standard equations for mid-point of the activity inhibition curves.

C. Screen for PPARα Agonist in HepG2 Human Liver Cells

Compound which show potent binding to PPARα were tested for their ability to stimulate PPARα dependent stimulation of reporter gene activity in HepG2, human liver derived, cells which express endogenous PPARα gene, or HepG2 cells stably expressing a Gal-4 DNA binding domain-PPARα ligand binding domain chimeric receptor (described below). Reporter gene constructs were made by inserting either 3 repeats of the rat fatty acid binding protein PPRE including the 7 nucleotides immediately 5', or 4 repeats of the gal4 response element upstream of the SV40 early minimal promoter of pSEAP2 (Clontech), 3×PPRE-SEAP and gal4-SEAP respectively. The chimeric receptor was made by cloning the cDNA encoding the ligand binding domain of human PPAR α in frame and 3' to the gal4 DNA binding domain (amino acids 1–47) in the mammalian bicistronic expression vector pIRESlneo (Clontech), gal4-PPAR α. Stable cell lines were generated by transfection with both gal4-SEAP and gal4-PPARα or with 3×PPRE-SEAP, using Lipofectamine Plus (Gibco) following the manufacturer's directions. Cells were plated onto 96 well plates and allowed to adhere overnight. The next day, serial dilutions of the compounds in growth media (DMEM plus 10% charcoal/dextran stripped FBS) containing 0.5% (v/v) DMSO, were added in duplicate to non-adjacent wells, and allowed to incubate for 24–40 hours at 37° C., 5% $CO_2$. Each plate had at least 6 wells of 1 μM standard, GW-2331 (an authentic PPARα selective agonist) as positive control, rosiglitazone (an authentic PPARγ agonist) as negative control and 3 wells of DMSO alone media as control. Following the incubation, media was removed, and endogenous phosphatases were inactivated as indicated above and SEAP activity in 25 μl aliquots of processed media was assayed in clear bottom, black 96 well plate (Falcon) by the addition of 100 μl Attophos reagent (Promega), incubation for 5 minutes in the dark at room temperature, and measuring the increase in fluorescence (excitation 450 nm, emission 580 nm) in a CytoFluor series 4000 plate reader (Perseptive Biosystems) 8 cycles, 1 minute/cycle. The relative rates of fluorescence emission were calculated as fold increase over DMSO control. Intrinsic activity was defined as the activity of the test compound at 1 μM as % of activity of the 1 μM standard. The $ED_{50}$ values were calculated using standard equations for mid-point of the activity curves.

EXAMPLE 64

In vivo Obese Animal Model

C57BL/6 mice were fed a diet rich in fat (40%) and sucrose (40%) (see, York {Genetic models of obesity} and Sclafani {Dietary models of obesity}, both in *Obesity*, Bjorntorp and Brodoff eds. JB Lippincott Company, 1992; McIntosh and Pederson; McNeill. eds. *CRC press LLC*, 337–398, 1999; Farrelly et al., *Proc. Natl. Acad. Sci.* 96: 14511–14516, 1999). Under these dietary conditions, C57BL/6 mice gain considerable body weight and become obese. These mice were treated with a dual PPARγ antagonist/PPARα agonist (dose 0.01 to 100 mg/kg/day), administered in a pharmacologically acceptable vehicle (such as but not limited to, 5% CM-cellulose) through orally, intravenous, subcutaneous or intraportal injection, or mixed with food or water, acutely or over an extended period of time. During the course of the study, various parameters such as water and food consumption, body weight gain, body composition by dual emission X-ray analyzer (DEXA, this instrument accurately measures body fat mass, body lean muscle mass and body bone mineral content), body temperature was measured by standard methods. Through tail vein bleeding, blood was collected in heparin-EDTA coated tubes to prevent clotting and blood plasma was separated and analyzed for glucose, free fatty acids, triglycerides and cholesterol using reagent kits available from Roche Diagnostics in a COBAS-MIRA instrument. Insulin and leptin are measured by commercially available ELISA kits. Compounds that act to reduce body weight and or decrease glucose were selected. At the end of the treatment period animals were euthanized by brief exposure to $CO_2$ and internal organs such as liver and white adipose tissue were harvested for additional analysis. These analyses may include, but not limited to, determination of lipid content, and effect on various PPARγ and PPARα target gene expression.

Test compounds that reduce body fat mass, body lean mass, prevent or ameliorate obesity, insulin resistance, are also tested in the disease models described above, in combination with an anti diabetic agent such as but not limited to metformin and sulfonylurea and/or a lipid lowering agent such as PPARα agonists (such as, but not limited to fenofibrate and gemfibrozil) and/or HMG CoA reductase inhibitors (such as, but not limited to, pravastatin, lovastatin, simvastatin and atorvastatin). During the course of the study various parameters such as water and food consumption, body weight gain, body temperature and plasma glucose, insulin, free fatty acids, triglycerides and cholesterol levels were measured. Compounds that act to reduce body fat mass increase body lean skeletal mass, body weight and or decrease glucose, and lipids were selected for further characterization.

EXAMPLE 65

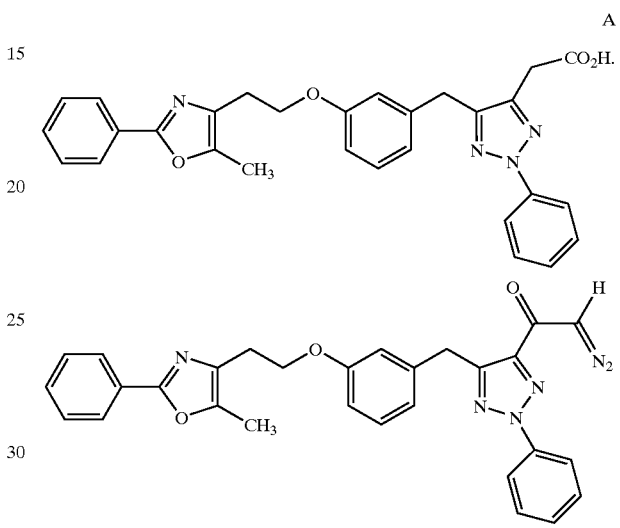

A solution of Example 1 compound (31 mg; 0.065 mmol), oxalyl chloride (0.50 mL of a 2.0 M solution in $CH_2Cl_2$; 1.0 mmol) and DMF (1 drop) was heated at 60° C. in a sealed tube overnight, then was cooled to RT and concentrated in vacuo to give the crude acid chloride. A solution of diazomethane was prepared by portionwise addition of 1-methyl-3-nitro-1-nitrosoguanidine (440 mg; 3 mmol) to a 0° C. solution of $Et_2O$ (2 mL) and 40% aqueous KOH (1.3 mL); after standing for 30 min, the organic phase (containing diazomethane) was dried (solid KOH) and used immediately. The crude acid chloride was dissolved in the 0° C. solution of ethereal diazomethane and was allowed to stand for 30 min at 0° C., then at RT for 2 h. Excess diazomethane in the reaction was quenched with acetic acid; volatiles were then removed in vacuo. The residue was chromatographed ($SiO_2$; hex:EtOAc 3:1) to give Part A compound (22 mg; 67%) as a yellow oil.

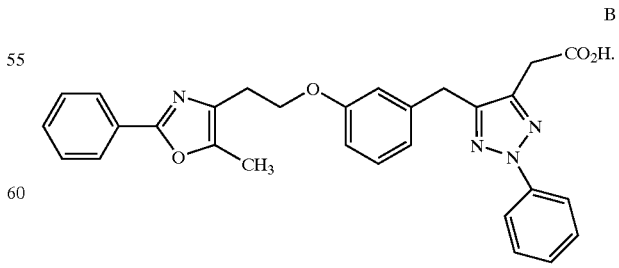

To a solution of Part A compound (22 mg; 0.044 mmol) in anhydrous MeOH (1 mL) were successively added silver benzoate (9 mg; 0.04 mmol) and anhydrous $Et_3N$ (35 μL;

0.25 mmol). The reaction was stirred at RT for 45 min (color became dark), then was partitioned between EtOAc and H₂O (10 mL each). The organic phase was successively washed with H₂O, 1 N aqueous HCl and 1 N aqueous NaOH (each 10 mL), then was concentrated in vacuo. The residual crude methyl ester was dissolved in THF (2 mL) and aqueous LiOH (2 mL of a 1 N solution) and the reaction was stirred at RT overnight. The reaction mixture was partitioned between EtOAc and aqueous 1 N HCl (10 mL each); the organic phase was washed with H₂O (2×10 mL), then was concentrated in vacuo. The residue was purified by preparative HPLC (YMC ODS 30×250 mm reverse phase column; flow rate 25 mL/min; 30 min continuous gradient from 70:30 A:B to 100% B; A=90:10:0.1H₂O:MeOH:TFA; B=90:10:0.1 MeOH:H₂O:TFA; detection at 220 nm) to give the title compound (8 mg; 36%) as white crystals.

[M+H]⁺=495.3

¹H NMR(CDCl₃): δ 2.38 (3H, s), 2.94 (2H, t, J=7.9 Hz), 3.68 (2H, s), 4.12 (2H, s), 4.26 (2H, t, J=7.9 Hz), 6.75 (1H, m), 6.90 (1H, s), 6.98 (1H, d, J=8 Hz), 7.22 (1H, t, J=7.9 Hz), 7.28 (1H, t, J=7.5 Hz), 7.41–7.48 (5H, m), 7.96–8.02 (4H, m)

EXAMPLE 66

A

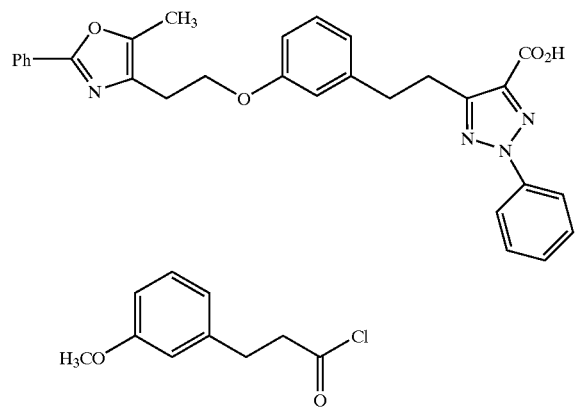

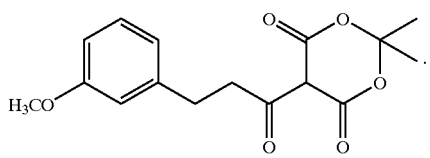

A mixture of 3-(3-methoxyphenyl) propionic acid (1.0 g; 5.55 mmol) and oxalyl chloride (3.0 mL of a 2 M solution in CH₂Cl₂; 6.0 mmol) in CH₂Cl₂ (5 mL) was heated in a sealed tube at 60° C. for 2 h, then cooled to RT and concentrated in vacuo to give Part A compound as an oil which was used without further purification in the next step.

B

To a 0° C. solution of Meldrum's acid (960 mg; 6.7 mmol) and pyridine (1.6 mL; 20 mmol) in CH₂Cl₂ (5 mL) was added dropwise Part A compound (1.20 g; 6.0 mmol) in CH₂Cl₂ (3 mL) over 30 min. The resultant mixture was stirred at RT for 2 h, then partitioned between aqueous 2 N HCl and CH₂Cl₂. The organic layer was dried (Na₂SO₄) and concentrated in vacuo to give crude Part B compound as an oil. This material was used in the next step without further purification.

C

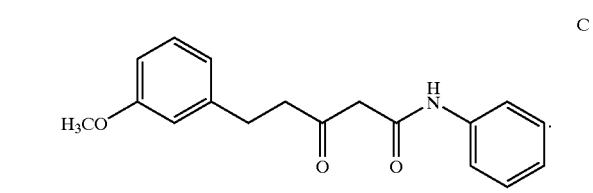

A solution of the crude Part B compound and aniline (910 μL; 10 mmol) in anhydrous toluene (10 mL) was heated to reflux for 3 h. The reaction solution was then washed with aqueous 1 M HCl, then concentrated in vacuo to give Part C compound (1.29 g; 78%) as a yellow oil.

D

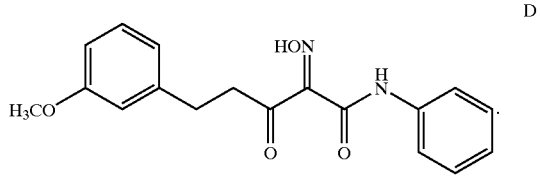

To a 0° C. aqueous solution of H₂SO₄ (640 μL of a 1.84 M solution; 12 mmol), H₂O (2 mL) and THF (7 mL) was added dropwise over 20 min a solution of Part C compound (1.29 g; 4.34 mmol), NaNO₂ (450 mg; 6.5 mmol) and aqueous 1 M NaOH (4.34 mL; 4.34 mmol). The reaction mixture was stirred at 0° C. for 2 h, then was partitioned between EtOAc and H₂O (20 mL each). The organic phase was washed with H₂O (2×20 mL), dried (Na₂SO₄) and concentrated in vacuo. The residue was chromatographed (SiO₂; 3:1 hex:EtOAc) to give Part D compound (780 mg; 55%) as yellow crystals.

E

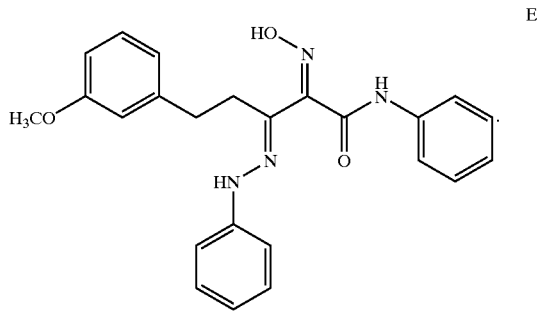

A solution of Part D compound (729 mg; 2.23 mmol), phenylhydrazine (0.30 mL; 3.0 mmol) and MgSO₄ (2 g) was refluxed in EtOH (5 mL) for 18 h, then was cooled to RT and partitioned between EtOAc and H₂O (20 mL each). The organic phase was washed with H₂O (2×20 mL), dried (Na₂SO₄) and concentrated in vacuo. The residue was crystallized from hexane/CH₂Cl₂ (1:1) to provide Part E compound (676 mg; 73%) as yellow crystals.

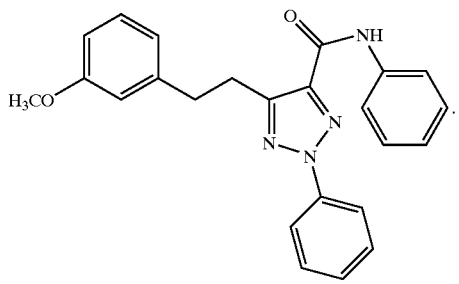

F

A solution of Part E compound (300 mg; 0.720 mmol) and TFAA (141 μL; 1.0 mmol) in CH$_2$Cl$_2$ was heated in a sealed tube at 45° C. for 2 h. At this point starting material had been consumed by analytical HPLC. Volatiles were removed in vacuo. The residue was chromatographed (SiO$_2$; 3:1 hex:EtOAc) to give Part F compound (280 mg; 98%) as a yellow oil.

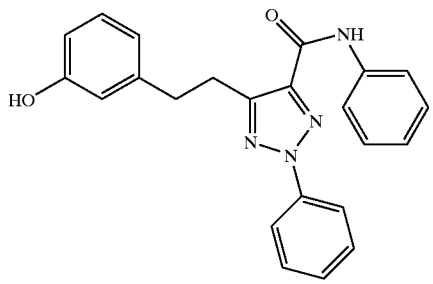

G

To a −70° C. solution of Part F compound (260 mg; 0.652 mmol) in CH$_2$Cl$_2$ (1 mL) was added dropwise BBr$_3$ (1.0 mL of a 1 M solution in CH$_2$Cl$_2$). The mixture was allowed to warm to RT and stirred at RT for 2 h, then was concentrated in vacuo. The residue was partitioned between EtOAc and H$_2$O (10 mL each). The organic phase was washed with H$_2$O (2×10 mL), dried (Na$_2$SO$_4$) and concentrated in vacuo. The residue was chromatographed (SiO$_2$; 3:1 hex:EtOAc) to give Part G compound (98 mg; 39%) as yellow crystals.

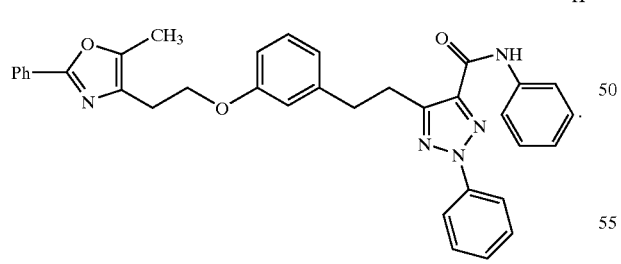

H

A mixture of Part G compound (28 mg; 0.073 mmol), 5-methyl 2-phenyl oxazole 4-ethanol mesylate (70 mg; 0.25 mmol; prepared as described in Example 11) and K$_2$CO$_3$ (138 mg; 1.0 mmol) in MeCN (5 mL) was stirred at 80° C. for 18 h, then was cooled to RT and partitioned between EtOAc and H$_2$O (20 mL each). The organic phase was washed with H$_2$O (2×20 mL), dried (Na$_2$SO$_4$) and concentrated in vacuo to give crude Part H compound, which was used in the next reaction without further purification.

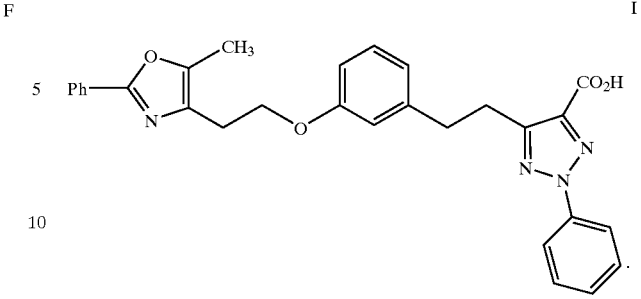

I

A solution of crude Part H compound and KOH (400 mg; 7.12 mmol) in EtOH (5 mL) was heated at 150° C. in a sealed tube for 3 h, then was cooled to RT and concentrated in vacuo. The residue was partitioned between EtOAc and 1 M aqueous HCl (20 mL each). The organic phase was washed with H$_2$O (20 mL), dried (Na$_2$SO$_4$) and concentrated in vacuo. The residue was purified by preparative HPLC (Phenomenex LUNA 5μ C18 21.2×100 mm reverse phase column; flow rate 25 mL/min; 8 min continuous gradient from 70:30 A:B to 100% B; A=90:10:0.1H$_2$O:MeOH:TFA; B=90:10:0.1 MeOH:H$_2$O:TFA; detection at 220 nm) to give the title compound (12 mg; 33% over 2 steps) as a solid.

[M+H]$^+$=495.3

$^1$H NMR (CDCl$_3$): δ 2.45 (3H, s), 3.05–3.10(4H, m), 3.39 (2H, t, J=7.9 Hz), 4.26 (2H, t, J=7.9 Hz), 6.69–6.75 (2H, m), 6.91 (1H, S), 7.11 (1H, t, J=7.9 Hz), 7.37 (1H, t, J=1.8 Hz), 7.45–7.55 (5H, m), 7.96–8.02 (4H, m) $^{13}$C NMR (CDCl$_3$): δ 163.4, 160.2, 158.4, 152.2, 146.9, 142.35, 139.2, 137.7, 132.2, 130.1, 129.3, 129.2, 128.4, 126.9, 124.2, 121.6, 119.4, 114.1, 113.4, 66.1, 35.2, 26.7, 24.8, 10.2.

EXAMPLE 67

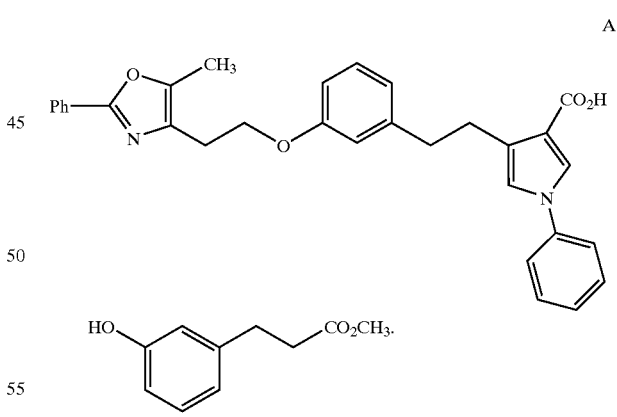

A

A solution of 3-(3-hydroxyphenyl)propanoic acid (3.01 g; 18.1 mmol) and concentrated sulfuric acid (0.5 mL) in MeOH (25 mL) was heated in an oil bath at 55° C. for 1 h. Volatiles were removed in vacuo and the mixture was neutralized with excess aqueous NaHCO$_3$, then was partitioned between EtOAc and H$_2$O. The organic phase was washed with brine, dried (MgSO$_4$) and concentrated in vacuo to give Part A compound (3.12 g; 96%) as a yellow oil.

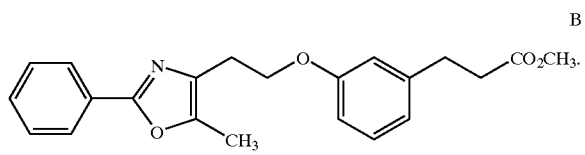

B

A mixture of Part A compound (3.12 g; 17.3 mmol), 5-methyl 2-phenyl oxazole 4-ethanol mesylate (4.86 g; 17.3 mmol; prepared as shown in Example 11) and $K_2CO_3$ (4.9 g; 36 mmol) in MeCN (100 mL) was heated overnight at 90° C. in an oil bath. Volatiles were removed in vacuo, and the residue was partitioned between $H_2O$ and EtOAc. The aqueous phase was extracted with EtOAc (2×) and the combined organic extracts were dried ($MgSO_4$) and concentrated in vacuo. The residue was chromatographed ($SiO_2$; continuous gradient from 100% hex to 100% EtOAc) to give the product, which still contained some unreacted phenol starting material. The product was washed repeatedly with aqueous 2N NaOH to furnish purified Part B compound (4.0 g; 63%) as an oil.

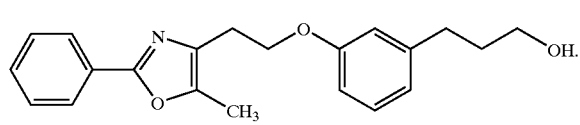

C

To a 0° C. solution of Part B compound (2.02 g; 5.55 mmol) in anhydrous THF (30 mL) was cautiously added portionwise solid $LiAlH_4$ (290 mg; 7.63 mmol). The reaction mixture was allowed to warm to RT, stirred at RT overnight, then was cautiously quenched with excess aqueous 1 N HCl. The mixture was extracted with EtOAc (2×). The combined organic extracts were washed with brine, dried ($Na_2SO_4$) and concentrated in vacuo to give Part C compound (1.90 g; 100% crude), which was used in the next reaction without further purification.

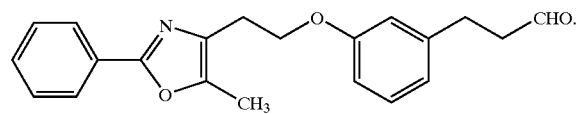

D

To a RT suspension of Dess-Martin periodinane (3.6 g; 8.5 mmol) in $CH_2Cl_2$ (50 mL) was added dropwise a solution of Part C compound (1.90 g; 5.64 mmol) in $CH_2Cl_2$ (10 mL) over 5 min. The reaction was stirred at RT for 4.5 h, then was concentrated in vacuo. The residue was chromatographed ($SiO_2$; continuous gradient from 100% hex to 100% EtOAc) to give Part D compound (1.70 g; 90%) as a colorless oil.

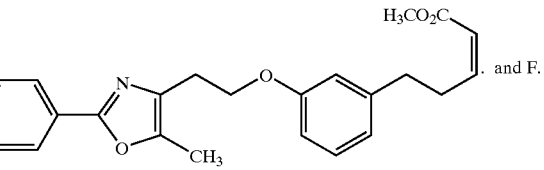

E and F.

Part E compound = cis-isomer; Part F compound = trans-isomer

To a −78° C. suspension of NaH (65 mg of a 60% mixture; 8.13 mmol) in anhydrous THF (10 mL) under $N_2$ was added $(CF_3CH_2O)_2P(O)CH_2CO_2CH_3$ (380 μL; 1.79 mmol) dropwise. The solution was stirred at −78° C. for 10 min, after which a solution of Part D compound (343 mg; 1.02 mmol) in THF (5 mL) was added dropwise over 5 min. The reaction mixture was stirred for 6 h at −78° C. (a significant amount of starting material remained at this point) then was allowed to warm slowly to RT and stirred overnight at RT. Excess saturated aqueous $NH_4Cl$ was added and the mixture was extracted with EtOAc (3×). The combined organic extracts were washed with brine, dried ($Na_2SO_4$) concentrated in vacuo. The residue was chromatographed ($SiO_2$; continuous gradient from 100% hex to 100% EtOAc) to give the cis-isomer Part E compound (199 mg; 50%) as a colorless oil as well as the trans-isomer Part F compound (86 mg; 22%) as a colorless oil.

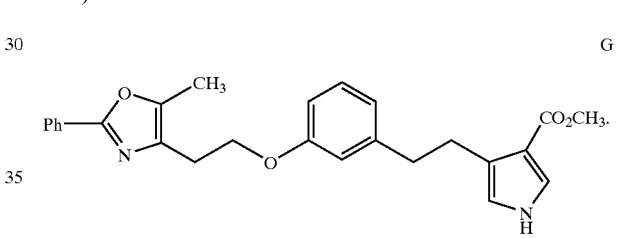

G

A solution of Part F compound (200 mg; 0.51 mmol) and tosylmethyl isocyanide (100 mg; 0.54 mmol) in anhydrous DMSO (1 mL) was added in one portion to a 0° C. suspension of NaH (30 mg of a 60% suspension in oil; 0.75 mmol) in anhydrous $Et_2O$ (1 mL). The mixture was allowed to warm to RT and stirred at RT for 30 min, then was partitioned between EtOAc (10 mL) and $H_2O$ (20 mL). The organic phase was washed with $H_2O$ (2×20 mL), dried ($Na_2SO_4$) and concentrated in vacuo. The residue was chromatographed ($SiO_2$; 3:1 hex:EtOAc) to give Part G compound (48 mg; 22%) as an oil.

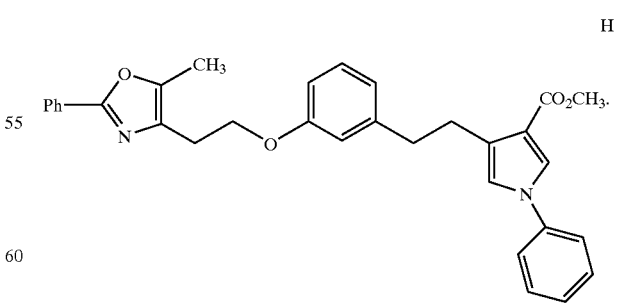

H

A mixture of Part G compound (48 mg; 0.11 mmol), phenyl boronic acid (20 mg; 0.17 mmol), $Cu(OAc)_2$ (9 mg; 0.05 mmol), anhydrous pyridine (0.5 mL), 2,6-lutidine (0.5 mL) and 4A molecular sieves (200 mg) in anhydrous toluene (1 mL) was heated at 70° C. (under a constant flow of air) for 5 h, then was cooled to RT and filtered. This solution was partitioned between EtOAc and aqueous 1 N HCl (10 mL each). The organic phase was washed with H₂O (2×10 mL), dried (Na₂SO₄) and concentrated in vacuo to give crude Part H compound as an oil, which was used in the next reaction without further purification.

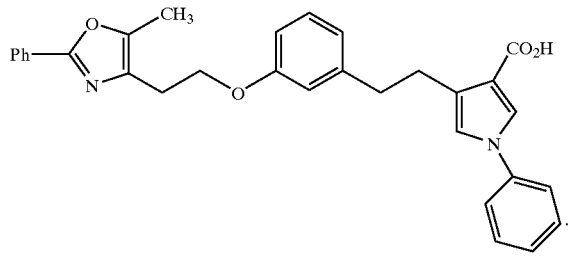

A solution of crude Part H compound in THF/1 M aqueous LiOH (2 mL of a 1:1 solution) was stirred for 18 h at 100° C., then was cooled to RT and partitioned between aqueous 1 N HCl and EtOAc (10 mL each). The organic phase was concentrated in vacuo and the residue was purified by preparative HPLC (as for Example 66 except that the continuous gradient used was 50:50 A:B to 100% B) to give the title compound (21 mg; 38%) as a white solid.

[M+H]⁺=493.2

¹H NMR (CDCl₃): δ 2.39 (3H, s), 2.89–2.93(2H, m), 3.00–3.09 (4H, m), 4.23 (2H, t, J=7.9 Hz), 6.72 (1H, m), 6.77–6.83 (3H, m), 7.17 (1H, t, J=7.9 Hz), 7.27–7.47 (8H, m), 7.76 (1H, d, J=2.6 Hz), 7.96–8.02 (2H, m)

¹³C NMR (CDCl₃) δ 116.6, 159.9, 158.5, 146.2, 144.0, 139.6, 131.5, 130.9, 129.7, 129.2, 128,9, 127.8, 126.7, 126.5, 126.4, 125.8, 121.2 120.7, 119.1, 114.8, 114.7, 111.9, 66.1, 36.8, 28.1, 25.5, 10.2

EXAMPLE 68

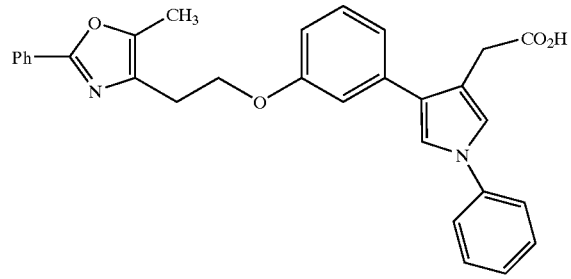

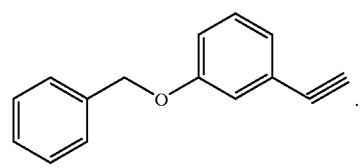

A mixture of 3-hydroxyphenylacetylene (5.0 g; 42 mmol), benzyl bromide (8.7 g; 51 mmol) and K₂CO₃ (15 g; 110 mmol) in MeCN (20 mL) was heated at 80° C. for 3 h, at which point analytical HPLC indicated that reaction was complete. The reaction was cooled to RT and filtered. The filtrate was concentrated in vacuo cautiously and the residue was chromatographed (SiO₂; 5:1 hex:EtOAc) to give Part A compound (6.82 g; 78%) as a clear oil.

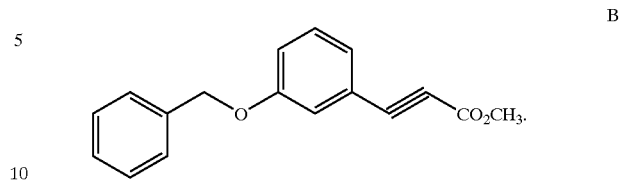

To a −78° C. solution of Part A compound (6.82 g; 32.7 mmol) in anhydrous THF (100 mL) was added methyllithium (40 mL of a 1.4 M solution in Et₂O; 56 mmol) dropwise. The reaction was stirred at −78° C. for 2 h, after which anhydrous dimethyl carbonate (4.7 mL; 56 mmol) was added in one portion. The reaction was allowed to warm to RT and stirred at RT for 30 min, after which saturated aqueous NH₄Cl (25 mL) was added. The mixture was partitioned between EtOAc and H₂O (200 mL each). The organic phase was washed with H₂O (2×100 mL), dried (Na₂SO₄) and concentrated in vacuo. The residue was chromatographed (SiO₂; 3:1 hexane:EtOAc) to give Part B compound (5.50 g; 63%) as yellow crystals.

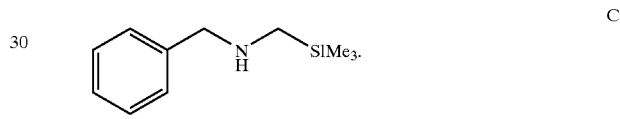

A solution of benzylamine (8.9 mL; 82 mmol) and chloromethyltrimethylsilane (5.0 g; 41 mmol) in MeCN (100 mL) was heated to reflux for 16 h. The reaction was cooled to RT, filtered, and the filtrate was concentrated in vacuo to a volume of ~30 mL. H₂O (100 mL) was added and the mixture was extracted with hexane (2×20 mL). The combined organic extracts were washed with H₂O (3×20 mL), dried (MgSO₄) and concentrated in vacuo to give Part C compound (7.70 g; 49%) as an oil.

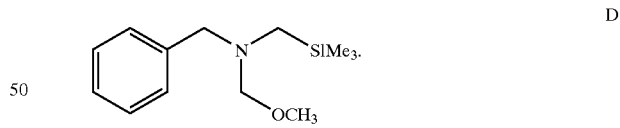

To a 0° C. solution of formaldehyde (4.6 g of a 37% aqueous solution; 55.7 mmol) and 1N aqueous NaOH (5 drops) was added dropwise Part C compound (7.70 g; 39.8 mmol). After the mixture had been stirred at 0° C. for 10 min, MeOH (4 mL) was added, followed by K₂CO₃ (4.0 g). The mixture was allowed to warm to RT and stirred at RT for 1 h. The organic phase was separated, more K₂CO₃ (2.0 g) was added, and the reaction was stirred at RT for 12 h. Et₂O (20 mL) was then added to the mixture, which was filtered and the filtrate was concentrated in vacuo. The residual oil was distilled at reduced pressure (0.5 mm Hg; 80° C.) to give Part D compound (4.67 g; 49%) as an oil.

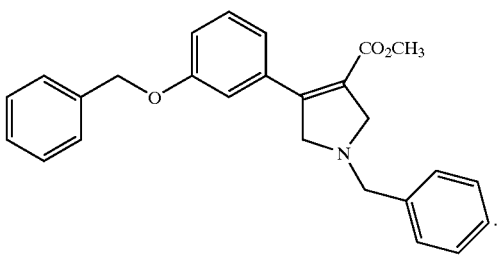

E

A mixture of Part B compound (5.50 g; 21 mmol), Part D compound (4.90 g; 21 mmol) and TFA (1 drop) in CH$_2$Cl$_2$ (20 mL) was stirred at RT for 3 h, then was concentrated in vacuo. The residue was chromatographed (SiO$_2$; hex:EtOAc 1:1) to give Part E compound (5.20 g; 63%) as a yellow oil.

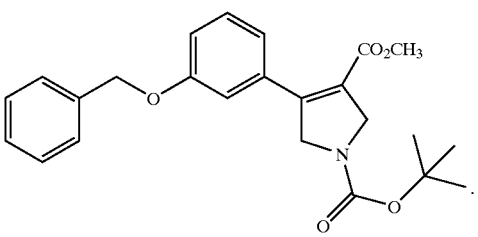

F

To a −78° C. solution of Part E compound (t.20 g; 13 mmol) in anhydrous CH$_2$Cl$_2$ (10 mL) was added CH$_3$CHClOCOCl (1.80 mL; 16 mmol). The reaction mixture was stirred at −70° C. for 10 min, then was allowed to warm to −15° C. and stirred at −15° C. for 3 h. At this point, HPLC indicated that all starting material had been consumed. Volatiles were removed in vacuo and MeOH (20 mL) was added; the solution was then stirred at RT for 18 h, then concentrated in vacuo. A solution of the residue and di-tert butyl dicarbonate (5 g; 23 mmol) in saturated aqueous NaHCO$_3$ and THF (10 mL each) was stirred at RT for 2 h, then was partitioned between EtOAc and H$_2$O (50 mL each). The organic phase was washed with H$_2$O (50 mL), dried (Na$_2$SO$_4$) and concentrated in vacuo. The residue was chromatographed (SiO$_2$; 2:1 hex:EtOAc) to give Part F compound (4.77 g; 90%) as an oil.

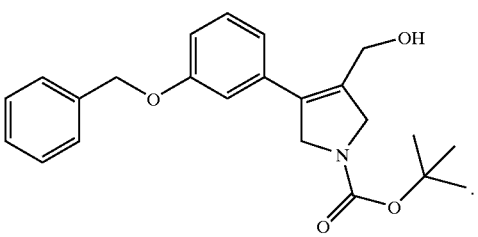

G

To a −70° C. solution of Part F compound (4.40 g; 10.9 mmol) in anhydrous THF (100 mL) was added dropwise DIBALH (16 mL of a 1 M solution in hexane; 16 mmol). The reaction was stirred at −70° C. for 20 min, then was warmed to RT and stirred at RT for 2 h, re-cooled to −70° C. and finally quenched by dropwise addition of MeOH (10 mL). The mixture was allowed to warm to RT, then aqueous Rochelle salt (100 mL of a 1 M solution) was added and stirring was continued for 1 h. The mixture was partitioned between H$_2$O and Et$_2$O (200 mL each). The aqueous phase was extracted with additional Et$_2$O (200 mL); the combined organic extracts were dried (Na$_2$SO$_4$) and concentrated in vacuo. The residue was chromatographed (SiO$_2$; EtOAc:hex:Et$_3$N 3:1:0.08) to give Part G compound (2.57 g; 67%) as an oil.

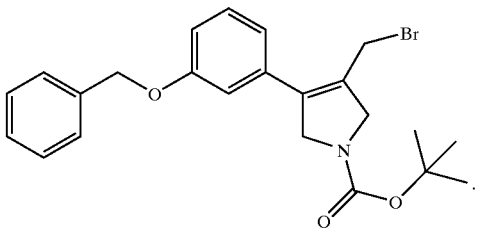

H

To a 0° C. mixture of Part G compound (2.57 g; 6.73 mmol) and triphenylphosphine (2.80 g; 10.7 mol) in CH$_2$Cl$_2$ (20 mL) was added a solution of carbon tetrabromide (3.0 g; 9.7 mmol) in CH$_2$Cl$_2$ (10 mL) dropwise-over 15 min. The reaction was allowed to warm to RT and stirred at RT for 4 h, then was filtered and concentrated in vacuo. The residue was chromatographed (SiO$_2$; hex:EtOAc 3:1) to give Part H compound (2.35 g; 48%) as an oil.

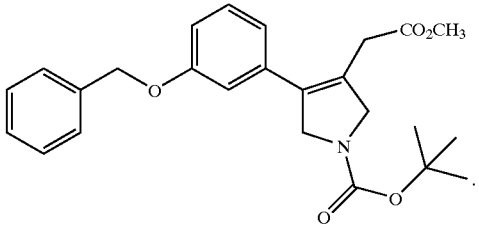

I

A mixture of Part H compound (600 mg; 1.37 mmol), (Ph$_3$P)$_4$Pd$^o$ (50 mg; 0.045 mmol) and KHCO$_3$ (1.75 mg; 1.75 mmol) in anhydrous MeOH (5 mL) in an autoclave was pressurized to 100 psi with carbon monoxide (flushed 3× with CO). The reaction mixture was stirred at RT for 3 days, after which the CO gas was released and the mixture was filtered. The filtrate was concentrated in vacuo and the residue was chromatographed (SiO$_2$; 3:1 hex:EtOAc) to give Part I compound (588 mg; 89%) as an oil.

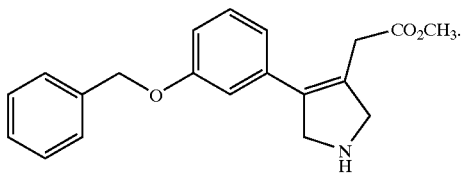

J

A solution of Part I compound (66 mg, 0.155 mmol) and TFA (1 mL) in CH$_2$Cl$_2$ (1 mL) was stirred at RT for 1 h, then was concentrated in vacuo to give crude Part J compound, which was used in the next step without further purification.

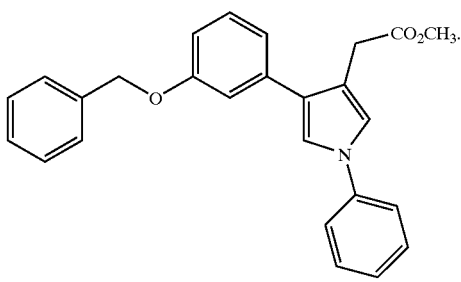

K

A mixture of crude Part J compound, phenyl boronic acid (200 mg; 1.64 mmol), Cu(OAc)$_2$ (10 mg; 0.06 mmol), anhydrous pyridine (0.5 mL), Et$_3$N (0.5 mL) and 4A molecular sieves (1 g) in anhydrous toluene (3 mL) was heated at 80° C. (under a constant flow of air) for 24 h, then was cooled to RT and filtered through a silica gel cartridge using 1:1 Hex:EtOAc as eluent. The filtrates were concentrated in vacuo to give Part K compound (15 mg; 24%) as an oil.

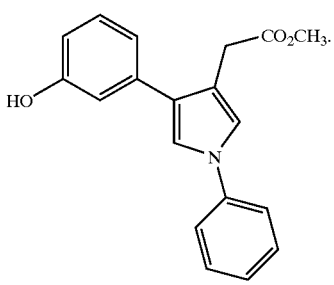

L

A mixture of Part K compound (15 mg; 0.038 mmol) and 10% Pd/C (10 mg) in MeOH (5 mL) was stirred under a hydrogen atmosphere (balloon) for 1 h, then was filtered. The filtrate was concentrated in vacuo to give crude Part L compound, which was used in the next step without further purification.

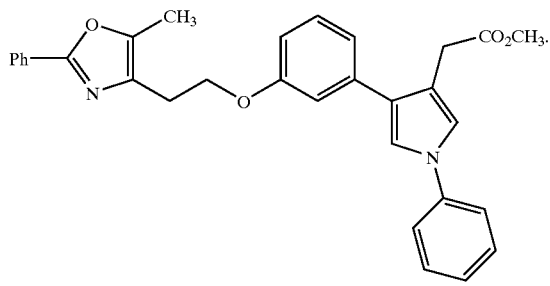

M

A mixture of crude Part L compound, 5-methyl 2-phenyl oxazole 4-ethanol mesylate (100 mg; 0.36 mmol; prepared as described in Example 11) and K$_2$CO$_3$ (500 mg; 3.0 mmol) in MeCN (6 mL) was stirred at 80° C. for 18 h, then was cooled to RT and partitioned between EtOAc and H$_2$O (15 mL each). The organic phase was washed with H$_2$O (2×20 mL), dried (Na$_2$SO$_4$) and concentrated in vacuo. The residue was chromatographed (SiO$_2$; 3:1 Hex:EtOAc) to give Part M compound.

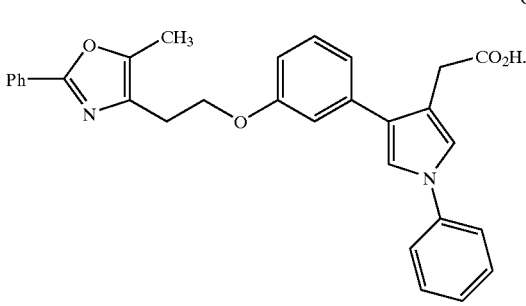

O

A solution of Part H compound in THF/1 M aqueous LiOH (2 mL of a 1:1 solution) was stirred for 2 h at 45° C., then was cooled to RT and partitioned between aqueous 1 N HCl (5 mL) and EtOAc (10 mL). The organic phase was washed with H$_2$O (5 mL) and was concentrated in vacuo. The residue was purified by preparative HPLC (same conditions as for Example 67) to give the title compound (10 mg; 55% overall) as a white solid.

[M+H]$^+$=479.3

$^1$H NMR (CDCl$_3$): δ 2.38 (3H, s), 3.04 (2H, t, J=7.9 Hz), 3.67 (2H, s), 4.32 (2H, t, J=7.9 Hz), 6.82 (1H, m) 7.01 (1H, d, J=8 Hz), 7.05–7.17 (2H, dd, J=4, 12 Hz) 7.20–7.30 (3H, m), 7.39–7.48 (7H, m), 7.96–8.02 (2H, m)

EXAMPLE 69

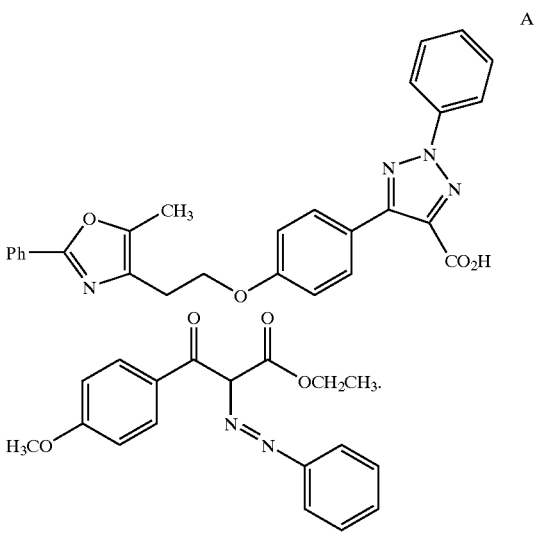

A

To a −20° C. solution of aniline (911 μL; 0.01 mmol) in aqueous HCl (3.5 mL of a 12 N solution +15 mL H$_2$O) was added dropwise a solution of NaNO$_2$ (828 mg; 0.012 mmol) in H$_2$O (5 mL). The diazonium ion solution was stirred at −20° C. for 15 min, then was added dropwise to a −2° C. mixture of ethyl 4-methoxybenzoyl acetate (2.22 g; 0.01 mmol) and sodium acetate (6.0 g; 73 mmol) in EtOH (12 mL). The reaction was stirred at −2° C. for 20 min, after which mixture was partitioned between EtOAc and H$_2$O (30 mL each). The organic phase was washed with H$_2$O (2×30 mL) and dried (Na$_2$SO$_4$). The residue was chromatographed (SiO$_2$; 5:1 Hex:EtOAc) to afford Part A compound (1.17 g; 35%) as a yellow oil (which still contained a small amount of ethyl 4-methoxybenzoyl acetate).

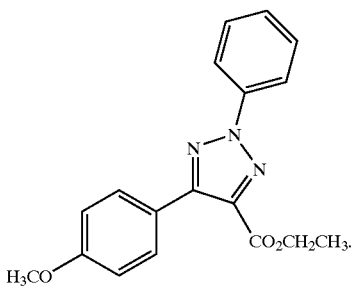

B

A mixture of Part A compound (1.17 g; 3.59 mmol), Cu(II)Cl$_2$.2H$_2$O (1.83 g; 10.7 mmol) and NH$_4$OAc (2.76 g; 35.9 mmol) in EtOH (20 mL) was heated in a sealed tube at 100° C. for 18 h. The reaction was cooled to RT and partitioned between EtOAc (50 mL) and H$_2$O (20 mL). The organic phase was washed with H$_2$O (2×20 mL), dried (Na$_2$SO$_4$) and concentrated in vacuo. The residue was recrystallized from hex:EtOAc:EtOH (1:1:1) to give Part B compound (528 mg; 45%) as yellow crystals.

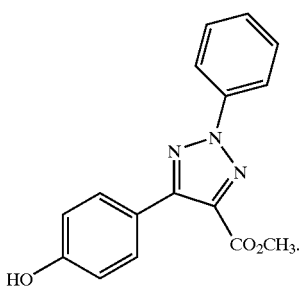

C

To a −70° C. solution of Part B compound (250 mg; 0.773 mmol) in CH$_2$Cl$_2$ (1 mL) was added dropwise BBr$_3$ (2.0 mL of a 1M solution in CH$_2$Cl$_2$). The mixture was allowed to warm to RT and stirred at RT for 4 h, after which MeOH (2 mL) was cautiously added and stirring was continued at RT overnight. Volatiles were removed in vacuo, and the residue was chromatographed (SiO$_2$; 3:1 hex:EtOAc) to give Part C compound (210 mg; 92%) as an oil.

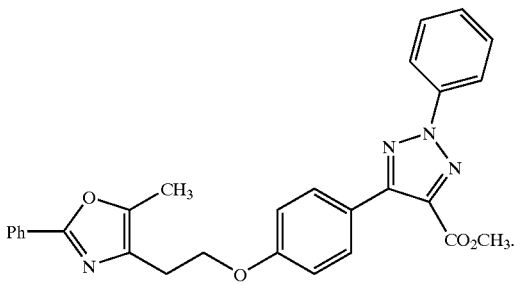

D

A mixture of Part C compound, 5-methyl 2-phenyl oxazole 4-ethanol mesylate (281 mg; 1.0 mmol; prepared as described in Example 11) and K$_2$CO$_3$ (829 mg; 6.0 mmol) in MeCN (10 mL) was stirred at 80° C. for 18 h, then was cooled to RT and partitioned between EtOAc (10 mL) and H$_2$O (20 mL). The organic phase was washed with H$_2$O (2×20 mL), dried (Na$_2$SO$_4$) and concentrated in vacuo to give crude Part D compound, which was used in the next step without further purification.

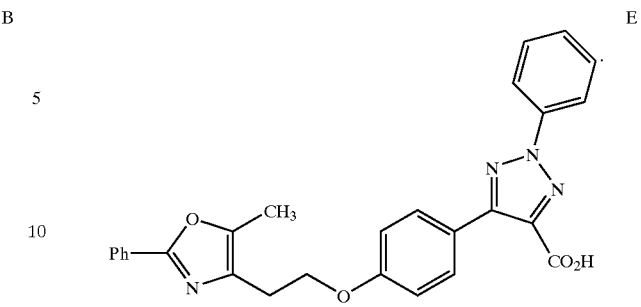

E

A solution of crude Part D compound in THF/1 M aqueous LiOH (10 mL of a 1:1 solution) was stirred for 3 h at 50° C., then was cooled to RT and partitioned between aqueous 1 N HCl and EtOAc (10 mL each). The organic phase was washed with H$_2$O (2×10 mL), dried (Na$_2$SO$_4$) and concentrated in vacuo to give the title compound (300 mg; 83%) as yellow crystals. [M+H]$^+$: 467.13

$^1$H NMR (CDCl$_3$) δ 2.32 (3H, s) 2.98 (2H, t, J=6.6 Hz), 4.25 (2H, t, J=6.6 Hz), 6.86–6.91 (2H, d, J=8.8 Hz), 7.30–7.38 (4H, m), 7.40–7.48 (2H, t, J=8.4 Hz), 7.87–7.7.93 (4H, m), 8.0–8.12 (2H, d, J=7.5 Hz).

EXAMPLE 70

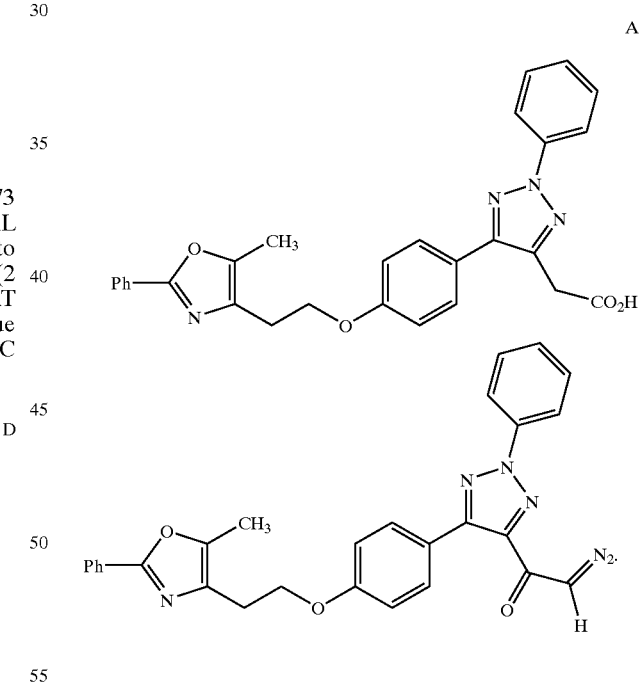

A

A solution of Example 69 (120 mg; 0.26 mmol) and oxalyl chloride (6 mL of a 2 N solution in CH$_2$Cl$_2$; 12.0 mmol) was heated at 50° C. in a sealed tube for 5 h, then was cooled to RT and concentrated in vacuo. A 0° C. solution of diazomethane [generated as in Example 65 from 1-methyl-3-nitro-1-nitrosoguanidine (441 mg; 3.0 mmol), Et$_2$O (10 mL) and 40% aqueous KOH (5 mL)] was cautiously added to the crude acid chloride and the reaction was stirred at 0° C. for 1 h. Volatiles were removed in vacuo and the residue was chromatographed (SiO2; 3:1 hex:EtOAc) to give Part A compound (82 mg; 64%) as a yellow solid.

B

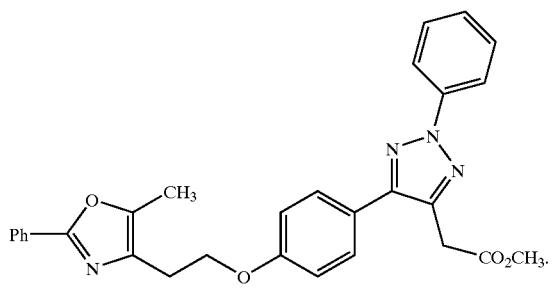

A mixture of Part A compound (82 mg; 0.167 mmol), silver benzoate (46 mg; 0.20 mmol) and anhydrous Et₃N (1 mL; 7.2 mmol) in anhydrous MeOH (5 mL) was stirred at RT for 1 h (dark solution), after which volatiles were removed in vacuo to give crude Part B compound, which was used in the next step without further purification.

C

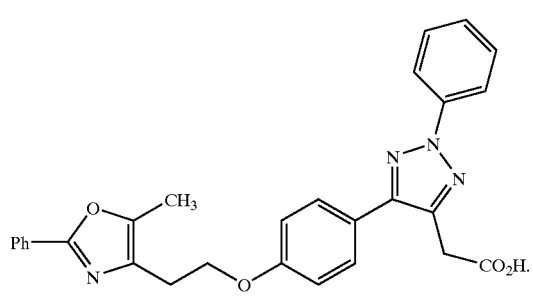

A solution of crude Part B compound in THF/1 M aqueous LiOH (10 mL of a 1:1 solution) was stirred for 1 h at 50° C., then was cooled to RT and partitioned between aqueous 1 N HCl and EtOAc (10 mL each). The organic phase was washed with H₂O (2×10 mL), dried (Na₂SO₄) and concentrated in vacuo. The residue was purified by preparative HPLC (same conditions as for Example 67) to give the title compound (13.8 mg; 17%) as a white solid.

[M+H]⁺: 481.1

¹H NMR (CDCl₃): δ 2.45 (3H, s), 3.11 (2H, t, J=5.72 Hz), 3.98 (2H, s), 4.27 (2H, t, J=5.7 Hz), 6.95–6.96 (2H, d, J=8.8 Hz), 7.33 (1H, t, J=7.0 Hz), 7.44–7.55 (5H, m), 7.63 (2H, d, J=8.8 Hz), 8.01 (2H, d, J=7.7 Hz), 8.07 (2H, d, J=7.9 Hz)

EXAMPLE 71

A

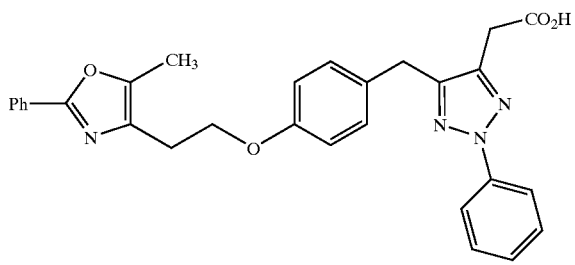

-continued

A mixture of Example 3 Part E compound (483 mg; 1.26 mmol) and KOH (1.0 g; 17.8 mmol) in EtOH (10 mL) was heated at 160° C. in a sealed tube for 2 h, then was cooled to RT and partitioned between EtOAc (20 mL) and aqueous 1N HCl (30 mL). The organic phase was washed with H₂O (2×30 mL), dried (Na₂SO₄) and concentrated in vacuo to give Part A compound as an oil, which was used in the next step without further purification.

B

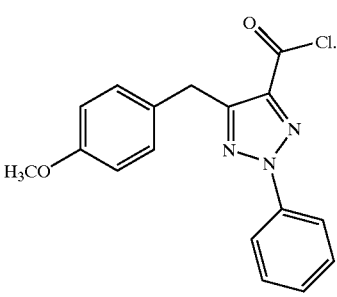

A solution of crude Part A compound and oxalyl chloride (1 mL; 11.5 mmol) in CH₂Cl₂ (10 mL) was stirred at RT for 2 h, after which volatiles were removed in vacuo to give Part B compound (410 mg; 99%) as a brown solid, which was used in the next step without further purification.

C

To a solution of crude Part B compound (41 mg; 0.125 mmol) in CH₂Cl₂ (5 mL) was added a solution of ethereal diazomethane [generated from 1-methyl-3-nitro-1-nitrosoguanidine (440 mg; 3 mmol) and 40% aqueous KOH (1.3 mL) as described for Example 65 Part A compound] was allowed to stand for 1 h at 0° C. Excess diazomethane in the reaction was quenched with acetic acid; volatiles were then removed in vacuo. The residue was chromatographed (SiO₂; hex:EtOAc 3:1) to give Part C compound (21 mg; 51%) as a yellow oil.

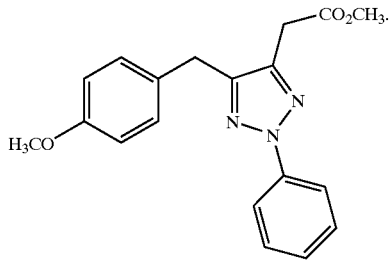

D

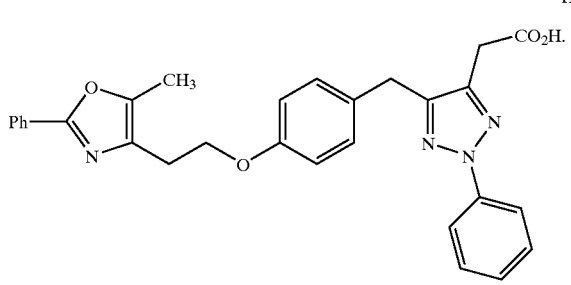

H

To a solution of Part C compound (21 mg; 0.063 mmol) in anhydrous MeOH (4 mL) was added silver benzoate (18 mg; 0.08 mmol) followed by $Et_3N$ (28 μL; 0.2 mmol) dropwise. The reaction mixture was stirred at RT for 2 h, then was concentrated in vacuo. The residue was chromatographed ($SiO_2$; hexane:EtOAc 1:1) to give Part D compound (21 mg; 90%) as an oil.

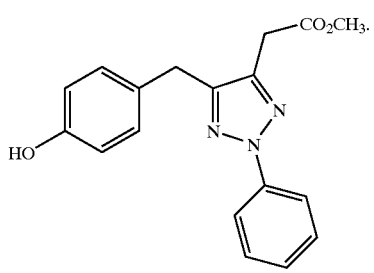

E

To a −70° C. solution of Part D compound (23 mg; 0.068 mmol) in $CH_2Cl_2$ (1 mL) was added dropwise $BBr_3$ (0.8 mL of a 1 M solution in $CH_2Cl_2$; 0.80 mmol). The mixture was allowed to warm to RT and stirred at RT for 2 h, after which MeOH (1 mL) was cautiously added and stirring was continued at RT for 3 h. Volatiles were removed in vacuo, and the residue was chromatographed ($SiO_2$; 3:1 hex:EtOAc) to give Part F compound (21 mg; 95%) as a oil.

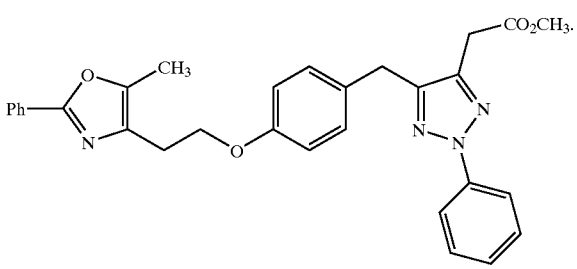

G

A mixture of Part F compound (21 mg; 0.065 mmol), 5-methyl 2-phenyl oxazole 4-ethanol mesylate (28 mg; 0.10 mmol; prepared as described in Example 11) and $K_2CO_3$ (690 mg; 5.0 mmol) in DMF (2 mL) was stirred at 80° C. for 18 h, then was cooled to RT and partitioned between EtOAc (10 mL) and $H_2O$ (10 mL). The organic phase was washed with $H_2O$ (2×10 mL), dried ($Na_2SO_4$) and concentrated in vacuo to give crude Part G compound as an oil, which was used in the next step without further purification.

A solution of crude Part H compound in THF/1 M aqueous LiOH (2 mL of a 1:1 solution) was stirred for 3 h at 50° C., then was cooled to RT and partitioned between aqueous 1 N HCl (5 mL) and EtOAc (10 mL). The organic phase was washed with $H_2O$ (10 mL), dried ($Na_2SO_4$) and concentrated in vacuo. The residue was purified by preparative HPLC (same conditions as Example 66) to afford the title compound (8 mg; 25% over 2 steps) as a white solid.

$[M+H]^+$: 495.3

$^1H$ NMR (DMSO-$d_6$) δ 2.35 (3H, s), 2.92 (2H, t, J=6.6 Hz), 3.68 (2H, s), 4.01 (2H, s), 4.18 (2H, t, J=6.6 Hz), 6.87 (2H, d, J=6.6 Hz), 7.17 (2H, d, J=6.6 Hz), 7.38 (1H, t, J=7.5 Hz), 7.48–7.55 (5H, m), 7.90–7.94 (4H, m), 12.64 (1H, s)

What is claimed is:

1. A compound which has the structure

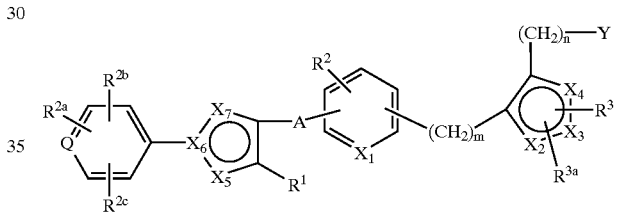

wherein m is 0, 1 or 2; n=0, 1 or 2;

Q is C or N;

A is $(CH_2)_x$ where x is 1 to 5; or A is $(CH_2)_x^1$, where $x^1$ is 2 to 5, with an alkenyl bond or an alkynyl bond embedded in the chain; or A is —$(CH_2)_x^2$—O—$(CH_2)_x^3$— where $x^2$ is 0 to 5 and $x^3$ is 0 to 5, provided that at least one of $x^2$ and $x^3$ is other than 0;

$X_1$ is CH or N;

$X_2$ is C, N, O or S;

$X_3$ is C, N, O or S;

$X_4$ is C, N, O or S, provided that at least one of $X_2$, $X_3$ and $X_4$ is N;

$X_5$ is C, N, O or S;

$X_6$ is C or N;

$X_7$ is C, N, O or S, provided that at least one of $X_5$, $X_6$ or $X_7$ is N; and where in each of $X_1$ through $X_7$, as defined above, C may include CH;

$R^1$ is H or alkyl;

$R^2$ is H, alkyl, alkoxy, halogen, amino or substituted amino;

$R^{2a}$, $R^{2b}$ and $R^{2c}$ are the same or different and are selected from H, alkyl, alkoxy, halogen, amino or substituted amino;

$R^3$ and $R^{3a}$ are the same or different and are independently selected from H, alkyl, arylalkyl, aryloxycarbonyl, alkyloxycarbonyl, alkynyloxycarbonyl, alkenyloxycarbonyl, arylcarbonyl, alkylcarbonyl, aryl, heteroaryl, alkyl(halo)aryloxycarbonyl, alkyloxy(halo)aryloxycarbonyl cycloalkylaryloxycarbonyl, cycloalkyloxyaryloxycarbonyl, cycloheteroalkyl, heteroarylcarbonyl, heteroaryl-heteroarylalkyl, alkylcarbonylamino, arylcarbonylamino, heteroarylcarbonylamino, alkoxycarbonylamino, aryloxycarbonylamino, heteroaryloxycarbonylamino, heteroaryl-heteroarylcarbonyl, alkylsulfonyl, alkenylsulfonyl, heteroaryloxycarbonyl, cycloheteroalkyloxycarbonyl, heteroarylalkyl, aminocarbonyl, substituted aminocarbonyl, alkylaminocarbonyl, arylaminocarbonyl, heteroarylalkenyl, cycloheteroalkylheteroarylalkyl, hydroxyalkyl, alkoxy, alkoxyaryloxycarbonyl, arylalkyloxycarbonyl, alkylaryloxycarbonyl, arylheteroarylalkyl, arylalkylarylalkyl, aryloxyarylalkyl, alkynyloxycarbonyl, haloalkoxyaryloxycarbonyl, alkoxycarbonylaryloxycarbonyl, aryloxyaryloxycarbonyl, arylsulfinylarylcarbonyl, arylthioarylcarbonyl, alkoxycarbonylaryloxycarbonyl, arylalkenyloxycarbonyl, heteroaryloxyarylalkyl, aryloxyarylcarbonyl, aryloxyarylalkyloxycarbonyl, arylalkylcarbonyl, aryloxyalkyloxycarbonyl arylalkylsulfonyl, arylthiocarbonyl, arylalkenylsulfonyl, heteroarylsulfonyl, arylsulfonyl, alkoxyarylalkyl, heteroarylalkoxycarbonyl, arylheteroarylalkyl, alkoxyarylcarbonyl, aryloxyheteroarylalkyl, heteroarylalkyloxyarylalkyl, arylarylalkyl, arylalkenylarylalkyl, arylalkoxyarylalkyl, arylcarbonylarylalkyl, alkylaryloxyarylalkyl, arylalkoxycarbonylheteroarylalkyl, heteroarylarylalkyl, arylcarbonylheteroarylalkyl, heteroaryloxyarylalkyl, arylalkenylheteroarylalkyl, arylaminoarylalkyl or aminocarbonylarylarylalkyl;

Y is $CO_2R^4$ (where $R^4$ is H or alkyl, or a prodrug ester) or Y is a C-linked 1-tetrazole, a phosphinic acid of the structure $P(O)(OR^{4a})R^5$, (where $R^{4a}$ is H or a prodrug ester, $R^5$ is alkyl or aryl) or a phosphonic acid of the structure $P(O)(OR^{4a})_2$;

$(CH_2)_x$, $(CH_2)_x^1$, $(CH_2)_x^2$, $(CH_2)_x^3$, $(CH_2)_m$, and $(CH_2)_n$ may be optionally substituted with 1, 2 or 3 substituents;

including all stereoisomers thereof, a prodrug ester thereof, and a pharmaceutically acceptable salt thereof.

2. A compound having the structure $x^2$ is 0 to 5 and $x^3$ is 0 to 5, provided that at least one of $x^2$ and $x^3$ is other than 0;

$X_2$ is C, N, O or S;

$X_3$ is C, N, O or S;

$X_4$ is C, N, O or S, provided that at least one of $X_2$, $X_3$ and $X_4$ is N;

and where in each of $X_2$ through $X_4$, as defined above, C may include CH;

$R^1$ is H or alkyl;

$R^2$ is H, alkyl, alkoxy, halogen, amino or substituted amino;

$R^{2a}$, $R^{2b}$ and $R^{2c}$ are the same or different and are selected from H, alkyl, alkoxy, halogen, amino or substituted amino;

$R^3$ and $R^{3a}$ are the same or different and are independently selected from H, alkyl, arylalkyl, aryloxycarbonyl, alkyloxycarbonyl, alkynyloxycarbonyl, alkenyloxycarbonyl, arylcarbonyl, alkylcarbonyl, aryl, heteroaryl, alkyl(halo)aryloxycarbonyl, alkyloxy(halo)aryloxycarbonyl cycloalkylaryloxycarbonyl, cycloalkyloxyaryloxycarbonyl, cycloheteroalkyl, heteroarylcarbonyl, heteroaryl-heteroarylalkyl, alkylcarbonylamino, arylcarbonylamino, heteroarylcarbonylamino, alkoxycarbonylamino, aryloxycarbonylamino, heteroaryloxycarbonylamino, heteroaryl-heteroarylcarbonyl, alkylsulfonyl, alkenylsulfonyl, heteroaryloxycarbonyl, cycloheteroalkyloxycarbonyl, heteroarylalkyl, aminocarbonyl, substituted aminocarbonyl, alkylaminocarbonyl, arylaminocarbonyl, heteroarylalkenyl, cycloheteroalkylheteroarylalkyl, hydroxyalkyl, alkoxy, alkoxyaryloxycarbonyl, arylalkyloxycarbonyl, alkylaryloxycarbonyl, arylheteroarylalkyl, arylalkylarylalkyl, aryloxyarylalkyl, alkynyloxycarbonyl, haloalkoxyaryloxycarbonyl, alkoxycarbonylaryloxycarbonyl, aryloxyaryloxycarbonyl, arylsulfinylarylcarbonyl, arylthioarylcarbonyl, alkoxycarbonylaryloxycarbonyl, arylalkenyloxycarbonyl, heteroaryloxyarylalkyl, aryloxyarylcarbonyl, aryloxyarylalkyloxycarbonyl, arylalkylcarbonyl, aryloxyalkyloxycarbonyl arylalkylsulfonyl, arylthiocarbonyl, arylalkenylsulfonyl, heteroarylsulfonyl, arylsulfonyl, alkoxyarylalkyl, heteroarylalkoxycarbonyl, arylheteroarylalkyl, alkoxyarylcarbonyl, aryloxyheteroarylalkyl, heteroarylalkyloxyarylalkyl, arylarylalkyl, arylalkenylarylalkyl,

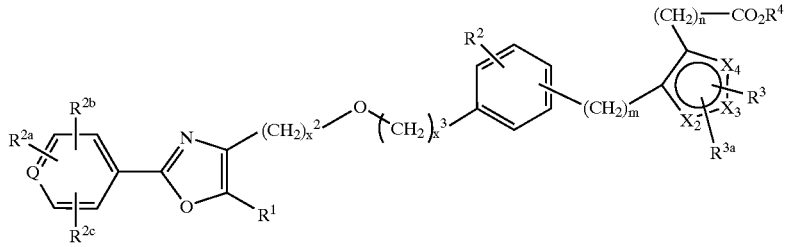

wherein m is 0, 1 or 2; n=0, 1 or 2;

Q is C or N;

arylalkoxyarylalkyl, arylcarbonylarylalkyl, alkylaryloxyarylalkyl, arylalkoxycarbonylheteroarylalkyl, heteroarylarylalkyl, arylcarbonylheteroarylalkyl, heteroaryloxyarylalkyl, arylalkenylheteroarylalkyl, arylaminoarylalkyl or aminocarbonylarylarylalkyl;

$(CH_2)_x^2$, $(CH_2)_x^3$, $(CH_2)_m$, and $(CH_2)_n$ may be optionally substituted with 1, 2 or 3 substituents;

including all stereoisomers thereof, a prodrug ester thereof, and a pharmaceutically acceptable salt thereof.

3. The compound as defined in claim 1 having the structure

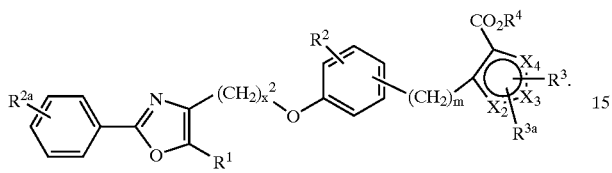

4. The compound as defined in claim 1 having the structure

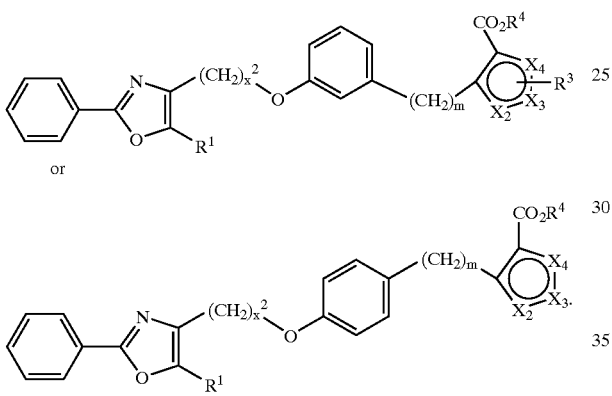

5. The compound as defined in claim 1 wherein $(CH_2)_x$, $(CH_2)_x^1$, $(CH_2)_x^2$, $(CH_2)_x^3$ are alkylene, alkenylene, allenyl, or alkynylene.

6. The compound as defined in claim 1 wherein $X_1$ is CH.

7. The compound as defined in claim 1 wherein $X_1$ is N.

8. The compound as defined in claim 1 having the structure

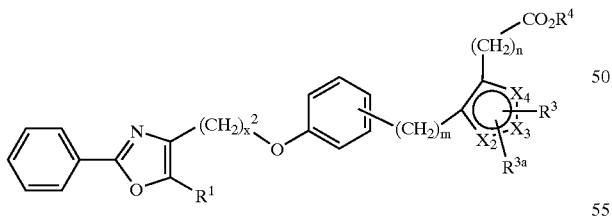

wherein $R^1$ is alkyl, $x^2$ is 1, 2 or 3, m is 0 or 1, or $(CH_2)_m$ is CHOH or CH-alkyl, n is 1, $(CH_2)_n$ is a bond or $CH_2$, $X_2$, $X_3$, and $X_4$ represent a total of 1, 2 or 3 nitrogens, $R^3$ is aryl, arylalkyl or heteroaryl and $R^{3a}$ is H or alkyl.

9. The compound as defined in claim 8 wherein $R^1$ is $CH_3$, and $R^3$ is phenyl or phenyl substituted with alkyl, polyhaloalkyl, halo or alkoxy.

10. The compound as defined in claim 1 having the structure

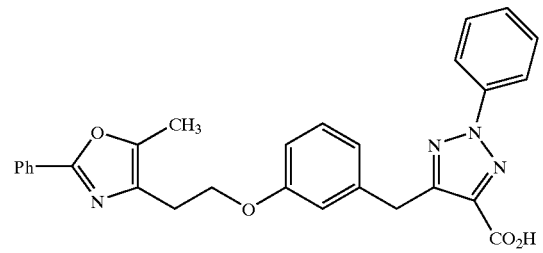

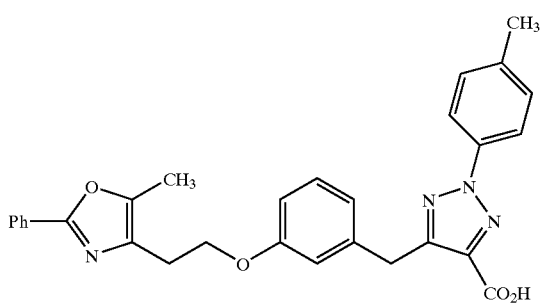

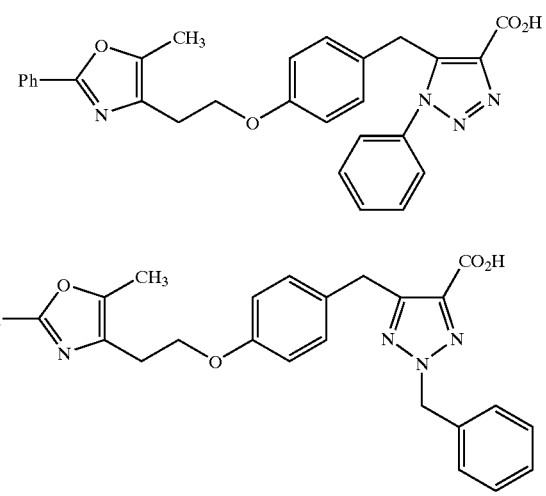

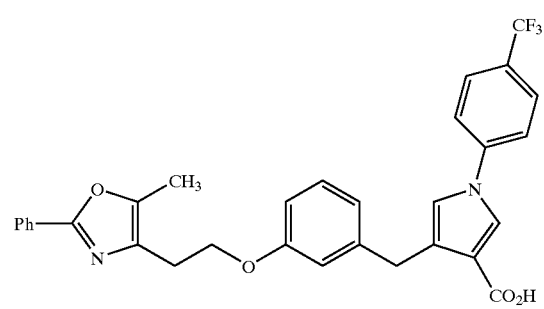

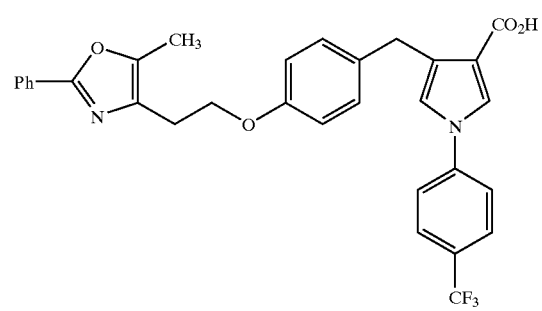

-continued
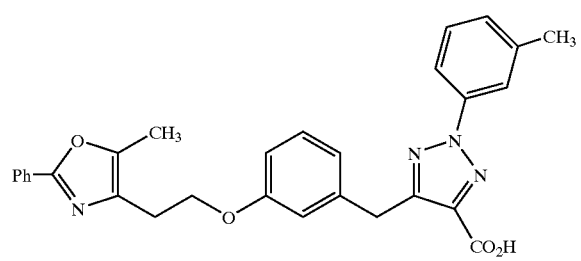
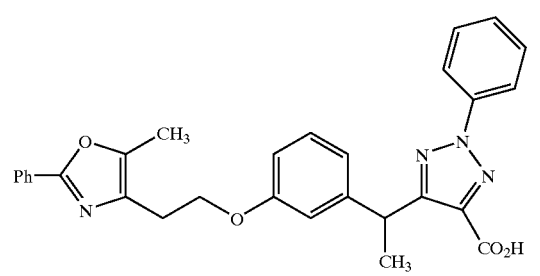
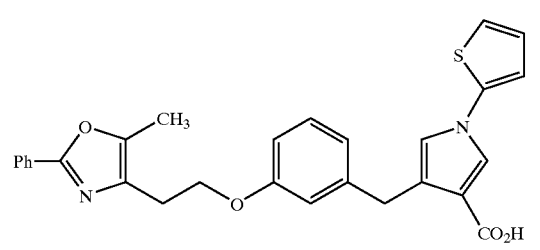
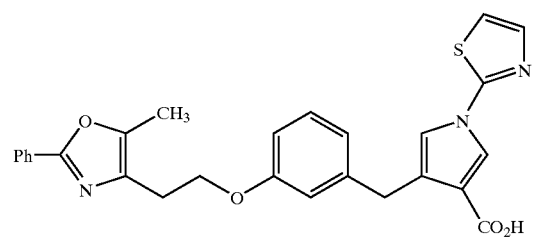
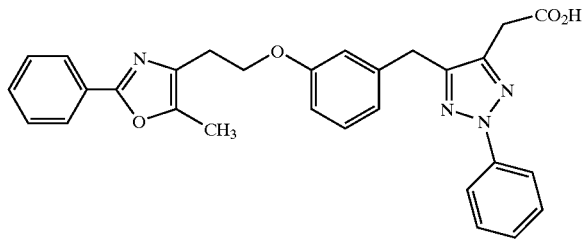
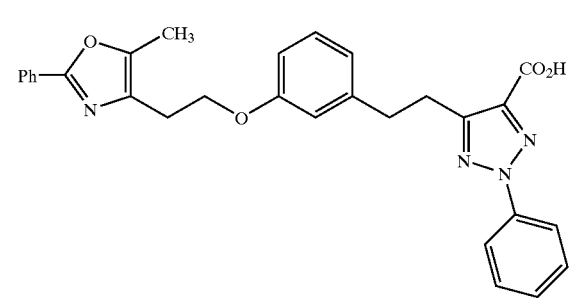
-continued
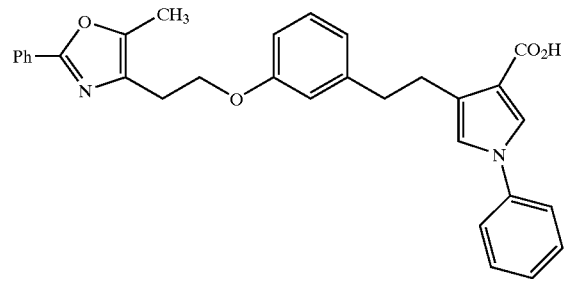
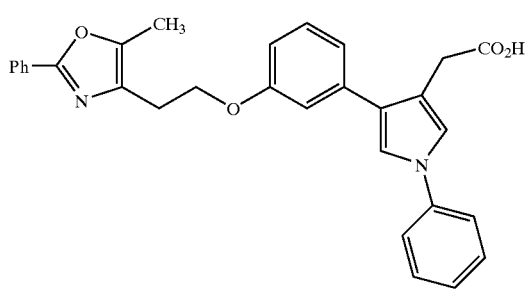
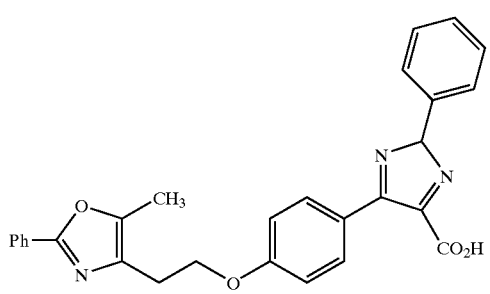
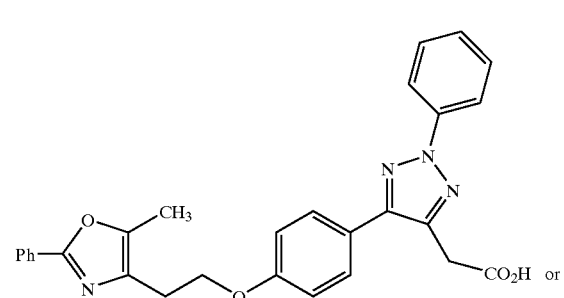
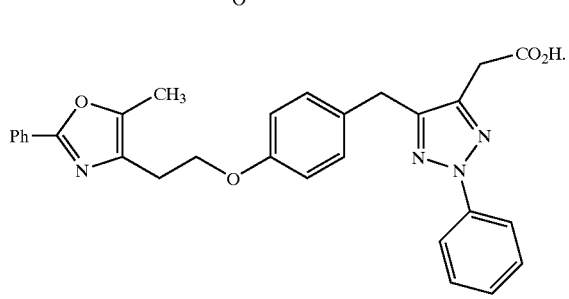
11. A pharmaceutical composition comprising a compound as defined in claim 1 and a pharmaceutically acceptable carrier therefor.
12. A method for lowering blood glucose levels, or for treating diabetes which comprises administering to a patient in need of treatment a therapeutically effective amount of a compound as defined in claim 1.

13. A method for treating a liposarcoma or epithelial tumor which comprises administering to a patient in need of treatment a therapeutically effective amount of a compound as defined in claim 1.

14. A pharmaceutical combination comprising a compound as defined in claim 1 and a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguamide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-I (GLP-I), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

15. The combination as defined in claim 12 wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, NN-2344, L895645, YM-440, R-119702, AJ9677, repaglinide, nateglinide, KAD1129, AR-HO39242, GW-409544, KRP297, AC2993, LY315902, P32/98 and/or NVP-DPP-728A, wherein the anti-obesity agent is orlistat, ATL-962, AJ9677, L750355, CP331648, sibutramine, topiramate, axokine, dexamphetamine, phentermine, phenylpropanolamine, and/or mazindol, wherein the lipid lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427, wherein the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl)amino]-2,2-dimethyl-7-oxo-1H-azepine-1-acetic acid (gemopatrilat) or CGS 30440;

an angiotensin II receptor antagonist which is irbesartan, losartan or valsartan;

amlodipine besylate, prazosin HCl, verapamil, nifedipine, nadolol, propranolol, carvedilol, or clonidine HCl, wherein the platelet aggregation inhibitor is aspirin, clopidogrel, ticlopidine, dipyridamole or ifetroban.

16. A method for treating insulin resistance, hyperglycemia, hyperinsulinemia, or elevated blood levels of free fatty acids or glycerol, hyperlipidemia, obesity, Syndrome X, dysmetabolic syndrome, inflammation, diabetic complications, impaired glucose homeostasis, impaired glucose tolerance, hypertriglyceridemia or atherosclerosis which comprises administering to a mammalian species in need of treatment a therapeutically effective amount of a pharmaceutical combination as defined in claim 14.

17. The method as defined in claim 13 wherein the disease is an epithelial tumor.

18. The method as defined in claim 17 wherein the epithelial tumor is a tumor of the breast, prostate, colon, ovaries, stomach or lung.

19. A method for treating irritable bowel syndrome, Crohn's disease, gastric ulceritis or osteroporosis, or psoriasis, or for treating obesity, insulin resistance, dyslipidemia, cardiovascular diseases and liver abnormalities, which comprises administering to a mammalian species in need of treatment a therapeutically effective amount of a compound as defined in claim 1.

* * * * *

UNITED STATES PATENT AND TRADEMARK OFFICE
CERTIFICATE OF CORRECTION

PATENT NO. : 6,967,212 B2
DATED : November 22, 2005
INVENTOR(S) : Peter T. Cheng et al.

It is certified that error appears in the above-identified patent and that said Letters Patent is hereby corrected as shown below:

Column 26,
Lines 30 to 50, delete " 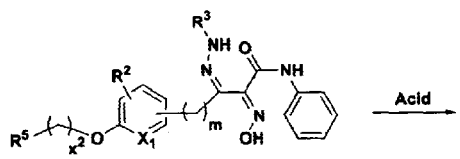 ".

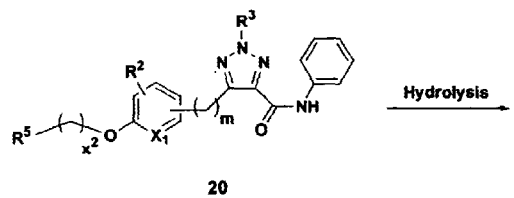

Column 61,
Line 44, change "biguamides" to -- biguanides --.
Lines 50, 52 and 54, each occurrence change "biguamide" to -- biguanide --.

Column 90,
Line 44, after "mixture" and before "was", delete the period ".".

UNITED STATES PATENT AND TRADEMARK OFFICE
CERTIFICATE OF CORRECTION

PATENT NO.    : 6,967,212 B2
DATED         : November 22, 2005
INVENTOR(S)   : Peter T. Cheng et al.

It is certified that error appears in the above-identified patent and that said Letters Patent is hereby corrected as shown below:

Column 117,
Line 22, change "$ED_{50}$" to -- $EC_{50}$ --.

Column 143,
Line 10, change "biguamide" to -- biguanide --.

Signed and Sealed this

Thirteenth Day of June, 2006

JON W. DUDAS
*Director of the United States Patent and Trademark Office*